US011340223B2

(12) United States Patent
Eden et al.

(10) Patent No.: US 11,340,223 B2
(45) Date of Patent: *May 24, 2022

(54) EARLY DIAGNOSIS OF INFECTIONS

(71) Applicant: MeMed Diagnostics Ltd., Tirat HaCarmel (IL)

(72) Inventors: Eran Eden, Haifa (IL); Kfir Oved, Hof HaCarmel (IL); Assaf Cohen-Dotan, Natania (IL); Roy Navon, Tel-Aviv (IL); Olga Boico, Haifa (IL); Meital Paz, Haifa (IL)

(73) Assignee: MeMed Diagnostics Ltd., Tirat HaCarmel (IL)

( * ) Notice: Subject to any disclaimer, the term of this patent is extended or adjusted under 35 U.S.C. 154(b) by 30 days.

This patent is subject to a terminal disclaimer.

(21) Appl. No.: 16/316,631

(22) PCT Filed: Jul. 10, 2017

(86) PCT No.: PCT/IL2017/050781
§ 371 (c)(1),
(2) Date: Jan. 10, 2019

(87) PCT Pub. No.: WO2018/011796
PCT Pub. Date: Jan. 18, 2018

(65) Prior Publication Data
US 2019/0242895 A1   Aug. 8, 2019

Related U.S. Application Data

(60) Provisional application No. 62/360,420, filed on Jul. 10, 2016.

(51) Int. Cl.
| | | |
|---|---|---|
| *A61P 31/04* | (2006.01) | |
| *G01N 33/535* | (2006.01) | |
| *G01N 33/547* | (2006.01) | |
| *G01N 33/569* | (2006.01) | |
| *G01N 33/68* | (2006.01) | |
| *C07K 14/525* | (2006.01) | |
| *C07K 14/54* | (2006.01) | |
| *C07K 14/57* | (2006.01) | |

(52) U.S. Cl.
CPC ........ *G01N 33/56944* (2013.01); *A61P 31/04* (2018.01); *G01N 33/535* (2013.01); *G01N 33/547* (2013.01); *G01N 33/56911* (2013.01); *G01N 33/56983* (2013.01); *G01N 33/6863* (2013.01); *G01N 33/6869* (2013.01); *G01N 33/6893* (2013.01); *G01N 2333/525* (2013.01); *G01N 2333/5412* (2013.01); *G01N 2333/5753* (2013.01); *G01N 2333/70578* (2013.01); *G01N 2333/70596* (2013.01); *G01N 2333/7155* (2013.01); *G01N 2800/26* (2013.01)

(58) Field of Classification Search
CPC .............. C07K 14/525; C07K 14/5412; C07K 14/57527; G01N 33/53; G01N 2333/525; G01N 2333/5753; G01N 2333/70578; G01N 2333/5412; G01N 2333/70596; G01N 2333/7155; G01N 33/52; G01N 33/535; G01N 33/68; G01N 22/56911; G01N 33/6863; G01N 33/547; G01N 33/6869

See application file for complete search history.

(56) References Cited

U.S. PATENT DOCUMENTS

| | | |
|---|---|---|
| 5,639,617 A | 6/1997 | Bohuon |
| 5,910,421 A | 6/1999 | Small, Jr. et al. |
| 6,077,665 A | 6/2000 | Welrich et al. |
| 6,136,526 A | 10/2000 | Venge |
| 6,210,661 B1 | 4/2001 | Enssle et al. |
| 6,709,855 B1 | 3/2004 | Stanton et al. |
| 6,756,483 B1 | 6/2004 | Bergmann et al. |
| 6,953,435 B2 | 10/2005 | Kondo et al. |
| 7,115,717 B2 | 10/2006 | Mori et al. |
| 7,132,246 B2 | 11/2006 | Bergmann et al. |
| 7,153,662 B2 | 12/2006 | Bergmann et al. |
| 7,157,081 B2 | 1/2007 | Bergmann et al. |
| 7,598,031 B2 | 10/2009 | Lew |
| 7,629,116 B2 | 12/2009 | Ott |
| 7,892,539 B2 | 2/2011 | Winoto et al. |
| 8,021,836 B2 | 9/2011 | Kolopp-Sarda et al. |
| 8,465,951 B2 | 6/2013 | Rao et al. |
| 8,507,210 B2 | 8/2013 | Bergmann et al. |
| 8,563,476 B2 | 10/2013 | Lillard, Jr. |
| 8,697,370 B2 | 4/2014 | Kas et al. |
| 8,821,876 B2 | 9/2014 | Ginsburg et al. |
| 9,034,328 B2 | 5/2015 | Takahashi |
| 9,709,565 B2 | 7/2017 | Eden et al. |
| 9,726,668 B2 | 8/2017 | Oved et al. |
| 9,850,539 B2 | 12/2017 | Tsalik et al. |
| 10,209,260 B2 | 2/2019 | Oved et al. |
| 10,303,846 B2 | 5/2019 | Eden et al. |
| 10,502,739 B2 | 12/2019 | Oved et al. |
| 10,859,574 B2 * | 12/2020 | Oved ............... G01N 33/56983 |

(Continued)

FOREIGN PATENT DOCUMENTS

| | | |
|---|---|---|
| CN | 1656378 | 8/2005 |
| CN | 101208602 | 6/2008 |
| CN | 101479389 | 7/2009 |
| CN | 101523217 | 9/2009 |
| CN | 101541976 | 9/2009 |

(Continued)

OTHER PUBLICATIONS

Hearing Notice Dated Jul. 16, 2019 From the Government of India, Patent Office, Intellectual Property Building Re. Application No. 1780/MUMNP/2014. (3 Pages).

(Continued)

*Primary Examiner* — Bridget E Bunner

(57) ABSTRACT

Methods of determining infection type are disclosed. In one embodiment, the method comprises measuring the amount of TRAIL and/or IP10 no more than two days from symptom onset.

Figure 1:
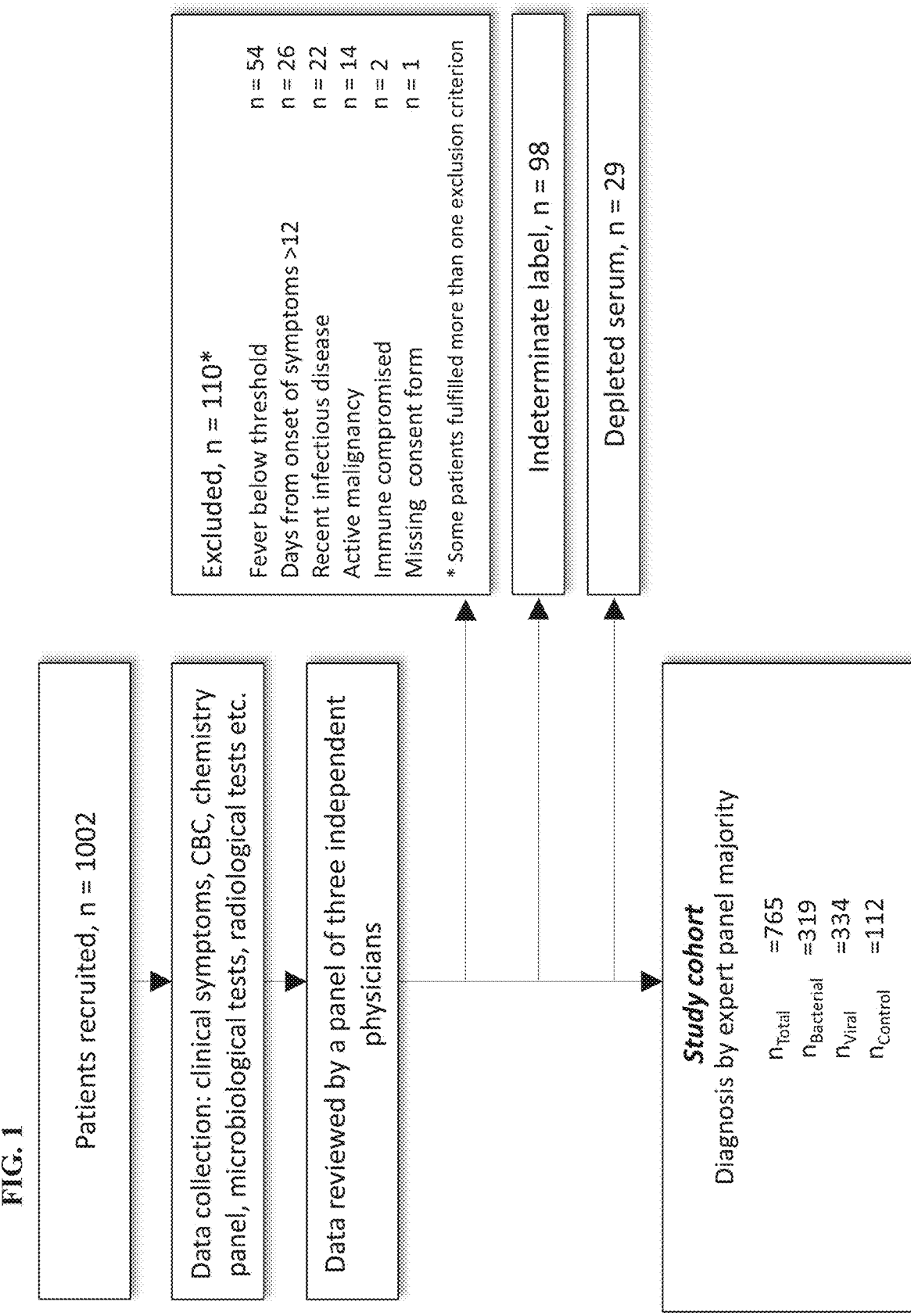

10 Claims, 13 Drawing Sheets
(12 of 13 Drawing Sheet(s) Filed in Color)
Specification includes a Sequence Listing.

(56) References Cited

U.S. PATENT DOCUMENTS

| | | | |
|---|---|---|---|
| 2004/0038201 | A1 | 2/2004 | Nau et al. |
| 2004/0043379 | A1 | 3/2004 | Hashimoto et al. |
| 2004/0171013 | A1 | 9/2004 | Lilius et al. |
| 2005/0227223 | A1 | 10/2005 | Miyawaki |
| 2005/0233395 | A1 | 10/2005 | Weiser et al. |
| 2006/0052278 | A1 | 3/2006 | Powell |
| 2006/0099628 | A1 | 5/2006 | Ching et al. |
| 2006/0246495 | A1 | 11/2006 | Garrett et al. |
| 2007/0015172 | A1 | 1/2007 | Zhang et al. |
| 2007/0184460 | A1 | 8/2007 | Ching et al. |
| 2007/0231816 | A1 | 10/2007 | Chaussabel et al. |
| 2007/0281319 | A1 | 12/2007 | Kolopp-Sarda et al. |
| 2008/0020379 | A1 | 1/2008 | Agan et al. |
| 2008/0064113 | A1 | 3/2008 | Goix et al. |
| 2008/0171323 | A1 | 7/2008 | Banchereau et al. |
| 2009/0155180 | A1 | 6/2009 | Jump et al. |
| 2009/0203534 | A1 | 8/2009 | Hossain et al. |
| 2010/0028874 | A1 | 2/2010 | Ramachandran et al. |
| 2010/0068147 | A1 | 3/2010 | Hibberd et al. |
| 2010/0143372 | A1 | 6/2010 | Yao et al. |
| 2010/0297611 | A1 | 11/2010 | Sambursky et al. |
| 2011/0059858 | A1 | 3/2011 | Kas et al. |
| 2011/0117563 | A1 | 5/2011 | Filipowicz et al. |
| 2011/0166166 | A1 | 7/2011 | Henkin |
| 2011/0183856 | A1 | 7/2011 | Agan et al. |
| 2011/0275542 | A1 | 11/2011 | Eden et al. |
| 2011/0312534 | A1 | 12/2011 | Kayser et al. |
| 2013/0309168 | A1 | 11/2013 | Ho |
| 2014/0127827 | A1 | 5/2014 | Kim et al. |
| 2014/0206016 | A1 | 7/2014 | Lozano Sanchez et al. |
| 2014/0227324 | A1 | 8/2014 | Robinson et al. |
| 2015/0017630 | A1 | 1/2015 | Oved et al. |
| 2016/0153993 | A1 | 6/2016 | Eden et al. |
| 2017/0030909 | A1 | 2/2017 | Oved et al. |
| 2017/0234873 | A1 | 8/2017 | Oved et al. |
| 2017/0235871 | A1 | 8/2017 | Eden et al. |
| 2017/0269081 | A1 | 9/2017 | Oved et al. |
| 2018/0074057 | A1 | 3/2018 | Eden et al. |
| 2019/0011456 | A1 | 1/2019 | Oved et al. |
| 2019/0041388 | A1 | 2/2019 | Oved et al. |
| 2019/0085378 | A1 | 3/2019 | Eden et al. |
| 2019/0120837 | A1 | 4/2019 | Eden et al. |
| 2019/0161813 | A1 | 5/2019 | Oved et al. |
| 2019/0237156 | A1 | 8/2019 | Eden et al. |
| 2019/0242894 | A1 | 8/2019 | Oved et al. |
| 2019/0271709 | A1 | 9/2019 | Eden et al. |
| 2020/0088728 | A1 | 3/2020 | Oved et al. |
| 2020/0388347 | A1 | 12/2020 | Eden et al. |
| 2020/0393463 | A1 | 12/2020 | Oved et al. |
| 2020/0400668 | A1 | 12/2020 | Eden et al. |

FOREIGN PATENT DOCUMENTS

| | | |
|---|---|---|
| CN | 101611314 | 12/2009 |
| CN | 101617056 | 12/2009 |
| CN | 101617230 | 12/2009 |
| CN | 101622364 | 1/2010 |
| CN | 101790687 | 7/2010 |
| CN | 102301002 | 12/2011 |
| CN | 103119444 | 5/2013 |
| CN | 104204803 | 12/2014 |
| CN | 105556308 | 5/2016 |
| EP | 1489416 | 12/2004 |
| JP | 2005-106694 | 4/2005 |
| JP | 2007-518062 | 7/2007 |
| JP | 2008-502908 | 1/2008 |
| JP | 2011-069696 | 4/2011 |
| KR | 10-2016-0072626 | 6/2016 |
| WO | WO 95/29404 | 11/1995 |
| WO | WO 99/33965 | 7/1999 |
| WO | WO 99/60171 | 11/1999 |
| WO | WO 01/14535 | 3/2001 |
| WO | WO 2004/108899 | 12/2004 |
| WO | WO2005/033327 | 4/2005 |
| WO | WO 2006/009702 | 1/2006 |
| WO | WO 2007/011412 | 1/2007 |
| WO | WO 2007/088355 | 8/2007 |
| WO | WO 2007/127801 | 11/2007 |
| WO | WO 2008/024642 | 2/2008 |
| WO | WO 2009/015821 | 2/2009 |
| WO | WO 2009/021521 | 2/2009 |
| WO | WO 2009/025743 | 2/2009 |
| WO | WO 2009/077864 | 6/2009 |
| WO | WO 2009/100907 | 8/2009 |
| WO | WO 2009/130176 | 10/2009 |
| WO | WO 2009/158521 | 12/2009 |
| WO | WO 2010/056637 | 5/2010 |
| WO | WO 2011/008349 | 1/2011 |
| WO | WO 2011/017682 | 2/2011 |
| WO | WO 2011/132086 | 10/2011 |
| WO | WO 2013/117746 | 8/2013 |
| WO | WO 2014/006408 | 1/2014 |
| WO | WO 2014/049255 | 4/2014 |
| WO | WO 2014/117873 | 8/2014 |
| WO | WO 2015/048098 | 4/2015 |
| WO | WO 2016/024278 | 2/2016 |
| WO | WO 2016/059636 | 4/2016 |
| WO | WO 2016/079219 | 5/2016 |
| WO | WO 2016/092554 | 6/2016 |
| WO | WO 2017/149547 | 9/2017 |
| WO | WO 2017/149548 | 9/2017 |
| WO | WO 2017/221255 | 12/2017 |
| WO | WO 2018/011795 | 1/2018 |
| WO | WO 2018/011796 | 1/2018 |
| WO | WO 2018/060998 | 4/2018 |
| WO | WO 2018/060999 | 4/2018 |

OTHER PUBLICATIONS

Notice Of Allowance dated Jul. 29, 2019 From the US Patent and Trademark Office Re. U.S. Appl. No. 15/237,728. (21 pages).
Partial European Search Report and Provisional Opinion dated Jun. 25, 2020 From the European Search Report Re. Application No. 20164056.2. (11 Pages).
Pepe et al. "Combining Diagnostic Test Results to Increase Accuracy", Biostatistics, XP055033234, 1(2): 123-140, Jun. 2000.
Official Action dated Apr. 23, 2019 From the US Patent and Trademark Office Re. U.S. Appl. No. 16/157,193. (47 pages).
Dirke et al. "TRAIL and DcR1 Expressions Are Differentially Regulated in the Pancreatic Islets of STZ- Versus CY-AppHed NOD Mice", Experimental Diabetes Research, Article ID 625813, pp. 1-11, 2011.
Kichev et al. "Tumor Necrosis Factor-Related Apoptosis-Inducing Ligand (TRAiL) Signaling and Cell Death in the Immature Central Nervous System after Hypoxia-Ischemia and Inflammation", Journal of Biological Chemistry 289(13): 9430-9439, 2014.
Notification of Office Action dated Aug. 22, 2019 From the State Intellectual Property Office of the People's Republic of China Re. Application No. 201580055946.0. (3 Pages).
Official Action dated Feb. 3, 2020 From the US Patent and Trademark Office Re. U.S. Appl. No. 16/355,984. (24 pages).
Search Report and Opinion dated Dec. 10, 2019 From the Servico Publico Federal, Ministerio da Economia, Instituto National da Propriedade Industrial do Brasil Re. Application No. BR112017002884-0 and Its Translation Into English. (7 Pages).
Supplementary European Search Report and the European Search Opinion dated Jan. 21, 2020 From the European Patent Office Re. Application No. 17827122.7.
Supplementary European Search Report and the European Search Opinion dated Jan. 28, 2020 From the European Patent Office Re. Application No. 17759389.4. (11 Pages).
Notification of Office Action dated Jul. 2, 2019 From the State Intellectual Property Office of the People's Republic of China Re. Application No. 201580075265.0. (3 Pages).
Request for Examination dated Jun. 18, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (11 Pages).

(56) References Cited

OTHER PUBLICATIONS

Translation Dated Jul. 10, 2019 of Notification of Office Action dated Jul. 2, 2019 From the State Intellectual Property Office of the People's Republic of China Re. Application No. 201580075265.0. (1 Page).
Communication Pursuant to Article 94(3) EPC dated Sep. 25, 2020 From the European Patent Office Re. Application No. 17827122.7. (5 Pages).
European Search Report and the European Search Opinion dated Sep. 28, 2020 From the European Patent Office Re. Application No. 20164056.2. (10 Pages).
Interview Summary dated Oct. 14, 2020 from the US Patent and Trademark Office Re. U.S. Appl. No. 16/081,906. (3 pages).
Applicant-Initiated Interview Summary dated Jul. 6, 2016 From the US Patent and Trademark Office Re. U.S. Appl. No. 14/377,887.
Applicant-Initiated Interview Summary dated Jul. 17, 2015 From the US Patent and Trademark Office Re. U.S. Appl. No. 13/090,893.
Applicant-Initiated Interview Summary dated Feb. 22, 2017 From the US Patent and Trademark Office Re. U.S. Appl. No. 14/377,887. (3 Pages).
Applicant-Initiated Interview Summary dated Oct. 26, 2017 From the US Patent and Trademark Office Re. U.S. Appl. No. 15/237,728. (3 pages).
Applicant-Initiated Interview Summary dated Jul. 30, 2018 From the US Patent and Trademark Office Re. U.S. Appl. No. 15/641,400. (3 pages).
Communication Pursuant to Article 94(3) EPC dated Dec. 9, 2016 From the European Patent Office Re. Application No. 13703112.6. (4 Pages).
Communication Pursuant to Article 94(3) EPC dated Oct. 9, 2018 From the European Patent Office Re. Application No. 11748712.4. (8 Pages).
Communication Pursuant to Article 94(3) EPC dated Jun. 17, 2016 From the European Patent Office Re. Application No. 11748712.4.
European Search Report and the European Search Opinion dated May 16, 2018 From the European Patent Office Re. Application No. 18162713.4. (7 Pages).
Examination Report dated Oct. 6, 2017 From the Australian Government, IP Australia Re. Application No. 2013217935. (2 Pages).
Examination Report Under Sections 12 & 13 of the Patents Act, 1970 and the Patents Rules, 2003 dated Mar. 26, 2018 From the Government of India, Intellectual Property India, Patents, Designs, Trade Marks, Geographical Indications Re. Application No. 9122/DELNP/2012. (7 Pages).
Examination Report Under Sections 12 & 13 of the Patents Act, 1970 and the Patents Rules, 2003 dated Nov. 30, 2018 From the Government of India, Intellectual Property India, Patents, Designs, Trade Marks, Geographical Indications Re. Application No. 1780/MUMNP/2014. (7 Pages).
Examiner-Initiated Interview Summary dated Nov. 27, 2017 From the US Patent and Trademark Office Re. U.S. Appl. No. 15/518,491. (2 pages).
International Preliminary Report on Patentability dated Apr. 11, 2019 From the International Bureau of WIPO Re. Application No. PCT/IL2017/051088. (6 Pages).
International Preliminary Report on Patentability dated Apr. 11, 2019 From the International Bureau of WIPO Re. Application No. PCT/IL2017/051089. (7 Pages).
International Preliminary Report on Patentability dated Sep. 13, 2018 From the International Bureau of WIPO Re. Application No. PCT/IL2017/050270. (7 Pages).
International Preliminary Report on Patentability dated Sep. 13, 2018 From the International Bureau of WIPO Re. Application No. PCT/IL2017/050271. (9 Pages).
International Preliminary Report on Patentability dated Jun. 22, 2017 From the International Bureau of WIPO Re. Application No. PCT/IL2015/051201. (7 Pages).
International Preliminary Report on Patentability dated Feb. 23, 2017 From the International Bureau of WIPO Re. Application No. PCT/IL2015/050823. (7 Pages).

International Preliminary Report on Patentability dated Jan. 24, 2019 From the International Bureau of WIPO Re. Application No. PCT/IL2017/050780. (9 Pages).
International Preliminary Report on Patentability dated Jan. 24, 2019 From the International Bureau of WIPO Re. Application No. PCT/IL2017/050781. (7 Pages).
International Preliminary Report on Patentability dated Apr. 27, 2017 From the International Bureau of WIPO Re. Application No. PCT/IL2015/051024. (7 Pages).
International Search Report and the Written Opinion dated Mar. 12, 2012 From the International Searching Authority Re. Application No. PCT/IB2011/001299.
International Search Report and the Written Opinion dated Sep. 14, 2017 From the International Searching Authority Re. Application No. PCT/1L2017/050781. (12 Pages).
International Search Report and the Written Opinion dated Jun. 15, 2017 From the International Searching Authority Re. Application No. PCT/IL2017/050270. (13 Pages).
International Search Report and the Written Opinion dated Jun. 15, 2017 From the International Searching Authority Re. Application No. PCT/IL2017/050271. (16 Pages).
International Search Report and the Written Opinion dated Sep. 18, 2017 From the International Searching Authority Re. Application No. PCT/IL2017/050780. (15 Pages).
International Search Report and the Written Opinion dated Jan. 20, 2016 From the International Searching Authority Re. Application No. PCT/TL2015/051024.
International Search Report and the Written Opinion dated Feb. 22, 2016 From the International Searching Authority Re. Application No. PCT/IL2015/051201.
International Search Report and the Written Opinion dated Dec. 25, 2017 From the International Searching Authority Re. Application No. PCT/IL2017/051088. (9 Pages).
International Search Report and the Written Opinion dated Dec. 28, 2017 From the International Searching Authority Re. Application No. PCT/IL2017/051089. (10 Pages).
International Search Report and the Written Opinion dated Nov. 29, 2015 From the International Searching Authority Re. Application No. PCT/IL2015/050823.
International Search Report dated Apr. 5, 2013 From the International Searching Authority Re. Application No. PCT/EP2013/052619.
Notice of Non-Compliant Amendment dated Aug. 4, 2015 From the US Patent and Trademark Office Re. U.S. Appl. No. 13/090,893.
Notice of Reasons for Rejection dated Nov. 1, 2016 From the Japan Patent Office Re. Application No. 2014-556086 and Its Translation Into English. (12 Pages).
Notice of Reasons for Rejection dated Apr. 2, 2019 From the Japan Patent Office Re. Application No. 2017-126712 and Its Translation Into English. (8 Pages).
Notice of Reasons for Rejection dated Jun. 19, 2018 From the Japan Patent Office Re. Application No. 2017-126712 and Its Translation Into English. (9 Pages).
Notice on Office Action and the Search Report dated Feb. 25, 2015 From The State Intellectual Property Office of the People's Republic of China Re. Application No. 201180030792.1 and Its Translation Into English.
Notification of Lack of Unity and Search Report dated Jan. 21, 2019 From the Federal Government Institution, Federal Institute of Industrial Property of the Federal Service for Intellectual Property, Patents and Trade Marks of the Russian Federation Re. Application No. 2017107750 and Its Translation of Office Action Into English. (12 Pages).
Notification of Office Action and Search Report dated Mar. 4, 2016 From the State Intellectual Property Office of the People's Republic of China Re. Application No. 201380019055.0.
Notification of Office Action and Search Report dated Jan. 11, 2019 From the State Intellectual Property Office of the People's Republic of China Re. Application No. 201580055946.0. (5 Pages).
Notification of Office Action and Search Report dated Feb. 13, 2017 From the State Intellectual Property Office of the People's Republic of China Re. Application No. 201380019055.0 and Its Translation of Office Action Into English. (10 Pages).

(56) References Cited

OTHER PUBLICATIONS

Notification of Office Action and Search Report dated Feb. 19, 2019 From the State Intellectual Property Office of the People's Republic of China Re. Application No. 201580075265.0 and A Summary of the Notification of Office Action Into English.(7 Pages).
Notification of Office Action and Search Report dated Jun. 19, 2018 From the State Intellectual Property Office of the People's Republic of China Re. Application No. 201580075265.0 and its English Summary. (14 Pages).
Notification of Office Action and Search Report dated Oct. 30, 2017 From the State Intellectual Property Office of the People's Republic of China Re. Application No. 201610817276.8. (10 Pages).
Notification of Office Action dated Jul. 3, 2015 From the State Intellectual Property Office of the People's Republic of China Re. Application No. 201380019055.0.
Notification of Office Action dated Aug. 4, 2016 From the State Intellectual Property Office of the People's Republic of China Re. Application No. 201380019055.0 and Its Translation Into English.
Notification of Office Action dated May 6, 2014 From The State Intellectual Property Office of the People's Republic of China Re. Application No. 201180030792.1 and Its Translation Into English.
Notification of Office Action dated Jan. 21, 2016 From The State Intellectual Property Office of the People's Republic of China Re. Application No. 201180030792.1 and Its Translation Into English.
Notification of Office Action dated Aug. 25, 2017 from the State Intellectual Property Office of the People's Republic of China Re. Application No. 201380019055.0. (6 Pages).
Notification of Office Action dated Aug. 28, 2015 From The State Intellectual Property Office of the People's Republic of China Re. Application No. 201180030792.1 and Its Translation Into English.
Notification of Office Action dated Aug. 30, 2018 From the State Intellectual Property Office of the People's Republic of China Re. Application No. 201610817276.8 and Its Translation Into English. (22 Pages).
Notification of Reexamination dated Jan. 12, 2018 From the State Intellectual Property Office of the People's Republic of China Re. Application No. 2013800190and Its Machine Translation into English.
Office Action dated Feb. 18, 2019 From the Israel Patent Office Re. Application No. 250585 and Its Translation Into English. (6 Pages).
Office Action dated Jun. 20, 2018 From the State Intellectual Property Office of the People's Republic of China Re. Application No. 201580055946.0 and Its Summary of the Notification of Office Action Into English.).(5 Pages).
Office Action dated Feb. 29, 2016 From the Israel Patent Office Re. Application No. 233998 and Its Translation Into English.
Official Action dated Sep. 1, 2015 From the US Patent and Trademark Office Re. U.S. Appl. No. 13/090,893.
Official Action dated Apr. 4, 2016 From the US Patent and Trademark Office Re. U.S. Appl. No. 13/090,893.
Official Action dated Jan. 4, 2019 From the US Patent and Trademark Office Re. Application No. 151713,722. (72 pages).
Official Action dated Feb. 6, 2018 From the US Patent and Trademark Office Re. U.S. Appl. No. 15/503,439. (63 pages).
Official Action dated Nov. 7, 2016 From the US Patent and Trademark Office Re. U.S. Appl. No. 13/090,893. (26 pages).
Official Action dated Jun. 10, 2013 From the US Patent and Trademark Office Re. U.S. Appl. No. 13/090,893.
Official Action dated Apr. 12, 2018 From the US Patent and Trademark Office Re. U.S. Appl. No. 15/518,491. (59 pages).
Official Action dated Aug. 12, 2015 From the US Patent and Trademark Office Re. U.S. Appl. No. 14/377,887.
Official Action dated May 12, 2017 From the US Patent and Trademark Office Re. U.S. Appl. No. 15/237,728. (27 pages).
Official Action dated Apr. 13, 2016 From the US Patent and Trademark Office Re. U.S. Appl. No. 14/377,887.
Official Action dated Mar. 13, 2014 From the US Patent and Trademark Office Re. U.S. Appl. No. 13/090,893.
Official Action dated Apr. 15, 2019 From the US Patent and Trademark Office Re. U.S. Appl. No. 15/237,728. (16 Pages).
Official Action dated Dec. 15, 2016 From the US Patent and Trademark Office Re. U.S. Appl. No. 14/377,887. (22 pages).
Official Action dated May 15, 2018 From the US Patent and Trademark Office Re. U.S. Appl. No. 15/237,728. (55 pages).
Official Action dated Nov. 16, 2018 From the US Patent and Trademark Office Re. U.S. Appl. No. 15/503,439. (41 pages).
Official Action dated Dec. 17, 2018 From the US Patent and Trademark Office Re. U.S. Appl. No. 15/237,728. (39 pages).
Official Action dated Nov. 18, 2016 From the US Patent and Trademark Office Re. U.S. Appl. No. 15/237,728. (33 pages).
Official Action dated Jan. 26, 2017 From the US Patent and Trademark Office Re. U.S. Appl. No. 15/015,309. (45 pages).
Official Action dated Mar. 26, 2015 From the US Patent and Trademark Office Re. U.S. Appl. No. 13/090,893.
Official Action dated Apr. 30, 2018 From the US Patent and Trademark Office Re. U.S. Appl. No. 15/641,400. (62 pages).
Official Action dated Mar. 30, 2018 From the US Patent and Trademark Office Re. U.S. Appl. No. 15/531,747. (67 pages).
Requisition by the Examiner dated Nov. 9, 2018 From the Innovation, Science and Economic Development Canada, Canadian Intellectual Property Office Re. Application No. 2,796,666. (3 Pages).
Requisition by the Examiner dated Jan. 18, 2018 From the Innovation, Science and Economic Development Canada, Canadian Intellectual Property Office Re. Application No. 2,796,666. (5 Pages).
Requisition by the Examiner dated Feb. 21, 2019 From the Innovation, Science and Economic Development Canada, Canadian Intellectual Property Office Re. Application No. 2,863,819. (8 Pages).
Restriction Official Action dated Nov. 2, 2017 From the US Patent and Trademark Office Re. U.S. Appl. No. 15/531,747. (9 pages).
Restriction Official Action dated Nov. 8, 2018 From the US Patent and Trademark Office Re. U.S. Appl. No. 16/157,193. (5 pages).
Restriction Official Action dated May 10, 2018 From the US Patent and Trademark Office Re. U.S. Appl. No. 15/713,722. (6 Pages).
Restriction Official Action dated Feb. 13, 2013 From the US Patent and Trademark Office Re. U.S. Appl. No. 13/090,893.
Restriction Official Action dated May 15, 2015 From the US Patent and Trademark Office Re. U.S. Appl. No. 14/377,887.
Restriction Official Action dated Aug. 31, 2017 From the US Patent and Trademark Office Re. U.S. Appl. No. 15/518,491. (6 pages).
Search Report dated May 6, 2014 From The State Intellectual Property Office of the People's Republic of China Re. Application No. 201180030792.1 and Its Translation Into English.
Second Notice Of Allowance dated Dec. 12, 2018 From the US Patent and Trademark Office Re. U.S. Appl. No. 15/641,400. (7 pages).
Supplementary European Search Report and the European Search Opinion dated Mar. 15, 2018 From the European Patent Office Re. Application No. 15831781.8. (11 Pages).
Supplementary European Search Report and the European Search Opinion dated Sep. 17, 2018 From the European Patent Office Re. Application No. 15868614.7. (18 Pages).
Supplementary Partial European Search Report and the European Provisional Opinion dated Jun. 1, 2018 From the European Patent Office Re. Application No. 15868614.7. (23 Pages).
Translation Dated Sep. 4, 2017 of Notification of Office Action dated Aug. 25, 2017 From the State Intellectual Property Office of the People's Republic of China Re. Application No. 201380019055.0.
Translation Dated Apr. 5, 2016 of Notification of Office Action dated Mar. 4, 2016 From the State Intellectual Property Office of the People's Republic of China Re. Application No. 201380019055.0.
Translation Dated Mar. 20, 2019 of Notification of Office Action dated Feb. 19, 2019 From the State Intellectual Property Office of the People's Republic of China Re. Application No. 201580075265.0. (5 Pages).
Translation Dated Sep. 21, 2015 of Office Action dated Jul. 3, 2015 From the State Intellectual Property Office of the People's Republic of China Re. Application No. 201380019055.0.
Translation of Notification Dated Jan. 30, 2019 From OA of Jan. 11, 2019 From the State Intellectual Property Office of the People's Republic of China Re. Application No. 201580055946.0.(1 Page).

(56) References Cited

OTHER PUBLICATIONS

Translation of Notification of Office Action and Search Report dated Oct. 30, 2017 From the State Intellectual Property Office of the People's Republic of China Re. Application No. 201610817276.8. (16 Pages).
Alexander et al. "*Staphylococcus aureus* and *Salmonella enterica* Serovar Dublin Induce Tumor Necrosis Factor-Related Apoptosis-Inducing Ligand Expression by Normal Mouse and Human Osteoblasts", Infection and Immunity, 69(3): 1581-1586, Mar. 2001.
Biezeveld et al. "Sustained Activation of Neutrophils in the Course of Kawasaki Disease: An Association with Matrix Metalloproteinases", Clinical & Experimental Immunology 141(1): 183-188, Jul. 2005.
Boldrick et al. "Stereotyped and Specific Gene Expression Programs in Human Innate Immune Responses to Bacteria", Proc. Natl. Acad. Sci. USA, PNAS, 99(2): 972-977, Jan. 22, 2002.
Borjesson et al. "Insights Into Pathogen Immune Evasion Mechanisms: Anaplasma Phagocytophilum Fails to Induce An Apoptosis Differentiation Program in Human Neutrophils", The Jurnal of Immunology, 174: 6364-6372, 2005.
Boser et al. "A Training Algorithm for Optimal Margin Classifiers", Proceedings of the 5th Annual ACM Workshop on Computational Learning Theory, COLT'92, Pittsburgh, PA, USA, Jul. 27-29, 1992, p. 144-152, Jul. 27, 1992.
Calvano et al. "A Network-Based Analysis of Systemic Inflammation in Humans", Nature, 437: 1032-1037, Oct. 13, 2005.
Carrol et al. "The Diagnostic and Prognostic Accuracy of Five Markers of Serious Bacterial Infection in Malawian Children With Sign of Severe Infection", PLoS ONE, 4(8): e6621-1-e6621-8, Aug. 2009.
Chagan-Yasutan et al. "Persistent Elevation of Plasma Osteopontin Levels in HIV Patients Despite Highly Active Antiretroviral Therapy", The Tohoku Journal of Experimental Medicine, 218(4): 285-292, Aug. 2009.
Chaussabel et al. "Analysis of Significance Patterns Identifies Ubiquitous and Disease-Specific Gene-Expression Signatures in Patient Peripheral Blood Leukocytes", Annals of the New York Academy of Sciences, 1062: 146-154, 2005.
Chen et al. "Discordant Protein and mRNA Expression in Lung Adenocarcinomas", Molecular & Cellular Proteomics: MCP, 1(4): 304-313, Apr. 2002.
Chieux et al. "MxA Protein in Capillary Blood of Children With Viral Infections", Journal of Medical Virology, 59: 547-551, 1999.
Chieux et al. "The MxA Protein Levels in Whole Blood Lysates of Patients With Various Viral Infections", Journal of Virological Methods, 70: 183-191, 1998.
Corada et al. "Monoclonal Antibodies Directed to Different Regions of Vascular Endothelial Cadherin Extracellular Domain Affect Adhesion and Clustering of the Protein and Modulate Endothelial Permeability", Blood, 97(6): 1679-1684, Mar. 15, 2001.
Cowland et al. "Molerular Charaderization and Pattern of Tissue Expression of the Gene for Neutrophil Gelatinase-Associated Upocalin from Humans", Genomics, 45:17-23,1997.
Cristianini et al. "An Introduction to Support Vector Machines and Other Kernel-Based Learning Methods: Contents", Cambridge University Press, 4 P., 2000.
Crowe et al. "Quantitative Immunocytofluorographic Analysis of CD4 Surface Antigen Expression and HIV Infection of Human Peripheral Blood Monocyte/Macrophages", Aids Research and Human Retroviruses, 3(2): 135-145, 1987.
Cummins et al. "The TRAIL to Viral Pathogenesis: The Good, the Bad and the Ugly", Current Molecular Medicine, XP055056835, 9(4): 495-505, May 1, 2009.
Duda et al. "Contents". Pattern Classification, 2nd Ed., 11 P., 2001.
Eberl et al. "A Rapid Crosstalk of Human ?? T Cells and Monocytes Drives the Acute Inflammation in Bacterial Infections", PLOS Pathogens 5(2): 1-16, 2009.
Falschlehner et al. "Following TRAIL's Path in the Immune System", Immunology, XP055056763, 127(2): 145-154, Jun. 1, 2009. Chapter 'TRAIL in Viral and Bacterial Infections'.

Feezor et al. "Molecular Characterization of the Acute Inflammatory Response to Infections With Gram-Negaitve Versus Gram-Positive Bacteria", Infection and Immunity, 71(10): 5803-5813, Oct. 2003.
Furey et al. "Support Vector Machine Classification and Validation of Cancer Tissue Samples Using Microarray Expression Data", Bioinformatics, 16(10): 906-914, Oct. 2000.
Halminen et al. "Expression of MxA Protein in Blood Lymphocytes Discriminates Between Viral and Bacterial Infections in Febrile Children", Pediatric Research, 41(5): 647-650, May 1997.
Hanley et al. "A Method of Comparing the Areas Under Receiver Operating Characteristics Curves Derived From the Same Cases", Radiology, 148(3): 839-843, Sep. 1983.
Hastie et al. "The Elements of Statistical Learning: Data Mining, Inference, and Prediction", Springer Series in Statistics, 2nd Ed., p. 1-745, 2001.
Hinson et al. "Viperin Is Highly Induced in Neutrophils and Macrophages during Acute and Chronic Lymphocytic Choriomeningitis Virus Infection", The Journal of Immunology, 184:5723-5731, 2010.
Hoffmann et al. "TRAIL Limits Excessive Host Immune Responses in Bacterial Meningitis", JCI The Journal of Clinical Investigation. 117(7): 2004-2013, Jul. 2, 2007.
Holland et al. "STAT3 Mutations in the Hyper-IgE Syndrome", The New England Journal of Medicine, 357(16): 1608-1619, Oct. 18, 2007.
Janols et al. "Lymphocyte and Monocyte Flow Cytometry Immunophenotyping as A Diagnostic Tool in Uncharacteristic Inflammatory Disorders", BMC Infectious Diseases, XP002663504, 10(205): 1-9, 2010. Abstract.
Jenner et al. "Insights Into Host Responses Against Pathogens From Transcriptional Profiling", Nature Review Microbiology, 3: 281-294, Apr. 2005.
Kaizer et al. "Gene Expression in Peripheral Blood Mononuclear Cells From Children With Diabetes", The Journal of Clinical Endocrinology & Metabolism, 92(9): 3705-3711, 2007.
Kawada et al. "Analysis of Gene-Expression Profiles by Oligonucleotide Microarray in Children With Influenza", Journal of General Virology, 87: 1677-1683, 2006.
Kohavi et al. "Wrappers for Feature Subset Selection", Artifical Intelligence, 97: 273-324, 1997.
Kotelkin et al. "Respiratory Syncytial Virus Infections Sensitizes Cells to Apoptosis Mediated by Tumor Necrosis Factor-Related Apoptosis-Inducing Ligand", Journal of Virology, XP055056816, 77(17): 9156-9172, Aug. 12, 2003. Fig.5B.
Lampe et al. "Expression of the Interferon-Induced MxA Protein in Viral Encephalitis", Neuropathology and Applied Neurobiology, 29(3): 273-279, May 27, 2003.
Le Roux "Les Examens a Visee Etiologique Dans les Pneumopathies Communautaires de l'Enfant (Hors Imagerie) [Laboratory Investigations in Acute Lower Respiratory Tract Infections in Children]", Archives de Pediatrie, XP002663501, 5(Suppl.l): 28S-32S, 1998. Abstract.
Leibovici et al. "The Benefit of Appropriate Empirical Antibiotic Treatment in Patients with Bloodstream Infection", Journal of Internal Medicine, 244(5): 379-386, Nov. 1, 1998.
Liabeuf et al. "The Circulating Soluble TRAIL Is A Negative Marker for Inflammation Inversely Associated With the Mortality Risk in Chronic Kidney Disease Patients", Nephrology Dialysis Transplantation, 25(8): 2596-2602, Advance Access Publication Feb. 26, 2010. Abstract, p. 2597, Right col. 2nd Para, Figs.2, 3.
Liu et al. "Early Days: Genomics and Human Responses to Infection", Current Opinion in Microbiology, 9: 312-319, Available Online May 6, 2006.
Malcolm et al. "Microarrays Analysis of Lipopolysaccharide-Treated Human Neutrophils", American Journal of Physiology, Lung Cellular' & Molecular Physiology, 284(4): L663-L670, First Published Dec. 20, 2002.
Mount "Bioinformatics: Sequence and Genome Analysis", Chaps. 1-10: 1-564, 2001.
Nakabayashi et al. "MxA-Based Recognition of Viral Illness in Febrile Children by A Whole Blood Assay", Pediatric Research, 60(6): 770-774, 2006.

(56) References Cited

OTHER PUBLICATIONS

Neu et al. "Expression of Tumor Necrosis Factor-Alpha-Related Apoptosis-Inducing Ligand and Its Proapoptotic Receptors Is Down-Regulated during Gastric Infection with Virulent cagA+/vacAsl+ Helicobacter pylori Strains", The Journal of Infectious Diseases 191(4): 571-578, Feb. 15, 2005.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008.
Niederman "Biological Markers to Determine Eligibility in Trials for Community-Acquired Pneumonia: A Focus on Procalcitonin", Clinical Infectious Diseases, XP002670357, 47(Suppl.3): S127-S132, Dec. 2008. Abstract.
Niessner et al. "Prognostic Value of Apoptosis Markers in Advanced Heart Failure Patients", European Heart Journal, 30(7): 789-796, Published Online Feb. 4, 2009. Abstract, Table 2, Fig.2.
Oda et al. "A Comprehensive Map of the Toll-Like Receptor Signaling Network". Molecular Systems Biology, 2(2006.0015): 1-20, Apr. 18, 2006.
Oved et al. "A Novel Host-Proteome Signature for Distinguishing Between Acute Bacterial and Viral Infections", PLOS ONE, 10(3): e0120012-l-e120012-18, Mar. 18, 2015. Figs.3C, 4.
Padlan "X-Ray Crystallography Of Antibodies", Advances In Protein Chemistry, 49: 57-133; 1996.
Paul et al. "Systematic Review and Meta-Analysis of the Efficacy of Appropriate Empiric Antibiotic Therapy for Sepsis", Antimicrobial Agents and Chemotherapy, 54(11): 4851-4863, Nov. 2010.
Radom-Aizik et al. "Effects of 30 Min. of Aerobic Exercise on Gene Expression in Human Neutrophils", Journal of Applied Physiology, 104: 236-243, 2008.
Ramilo et al. "Gene Expression Patterns in Blood Leukocytes Discriminate Patients With Acute Infections", Blood. 109(5): 2066-2077, Mar. 1, 2007.
Ramilo et al. "Gene Expression Patterns in Blood Leukocytes Discriminate Patients With Acute Infections", Blood. 109(5): 2066-2077, Published Online Nov. 14, 2006.
RayBiotech "Mouse L308 Array, Membrane [AAM-BLM-1]l-Series-308-Label-Based-Mouse-Cytok", RayBiotech. XP055473187, Retrieved From the Internet, 7 P., May 7, 2018.
Rosseau et al. "Comparative Transcriptional Profiling of the Lung Reveals Shared and Distinct Features of *Streptococcus pneumoniae* and Influenza A Virus Infection", Immunology, 120: 380-391, 2006.
Secchiero et al. "Potential Prognostic Significance of Decreased Serum Levels of TRAIL After Acute Myocardial Infarction", PLoS ONE, XP055056988, 4(2): e4442-1-e4442-6, Feb. 16, 2009. Fig.1.
Shimetani et al. "Levels of Three Inflammation Markers, C-Reactive Protein, Serum Amyloid A Protein and Procalcitonin, in the Serum and Cerebrospinal Fluid of Patients With Meningitis", Scandinavian Journal of Clinical and Laboratory Investigation, XP008113027, 61(7): 567-574, 2001. Abstract.
Singer et al. "The Third International Consensus Definitions for Sepsis and Septic Shock (Sepsis-3)", Journal of the American Medical Association, JAMA, 315(8): 801-810, Feb. 23, 2016. Box 3, Fig.
Smith et al. "Quantitative Assessment of Human Whole Blood RNA as A Potential Biomarker for Infectious Disease", Analyst, 132: 1200-1209, First Published Oct. 31, 2007.
Sukumaran et al. "Early Transcriptional Response of Human Neutrophils to Anaplasma Phagocytophilum Infection", Infection and Immunity, 73(12): 8089-8099, Dec. 1, 2005.
Sullivan Pepe et al. "Combining Diagnostic Test Results to Increase Accuracy", Biostatistics, XP055033234, 1(2): 123-140, Jun. 1, 2000. Abstract, Section 2.4.
Tang et al. "Gene-Expression Profiling of Gram-Positive and Gram-Negative Sepsis in Critically Ill Patients", Critical Care Medicine, 36(4): 1125-1128, 2008.

Tang et al. "Hvpoxic Preconditioning Enhances the Benefit of Cardiac Progenitor Cell Therapy for Treatment of Myocardial Infarction bv Inducing CXCR4 Expression", Circulation Research, XP055473182, 104(10): 1209-1216, May 22, 2009. Online Table 1.
Tang et al. "The Use of Gene-Expression Profiling to Identify Candidate Genes in Human Sepsis", American Journal of Respiratory and Critical Care Medicine, 176: 676-684, Originally Published Jun. 15, 2007.
Thivierge et al. "Eukaryotic Elongation Factor 1A Interacts With Turnip Mosaic Virus RNA-Dependent RNA Polymerase and VPg-Pro in Virus-Induced Vesicles", Virology, XP002663503, 377(1): 216-225, Jul. 2008. Abstract, p. 220, r-h col. Para 3-p. 222, r-h col. Para 1.
Tian et al. "Soluble Tumor Necrosis Factor Related Apoptosis Inducing Ligand Level as A Predictor of Severity of Sepsis and the Risk of Mortality in Septic Patients", PLOS One, 8(12): e82204-1-e82204-5, Dec. 12, 2013. 'Study Design' Para, 'Inclusion Criteria' Para, Table 1, Figs. 1, 3, Abstract, Table 1.
Tisato et al. "Low Circulating TRAIL Levels Are Associated with Increase of Resistin and Lipocalin-2/ngal Adipokines in Postmenopausal Women", Mediators of Inflammation, Article ID 5356020, 8 Pages, 2017.
Torkkola "Feature Extraction by Non-Parametric Mutual Information Maximization", Journal of Machine Learning Research, 3: 1415-1438, Mar. 2003.
Tsuji "TRAILing Gastrointestinal Pathogenesis", Journal of Gastroenterology and Hepatology, 18(7): 753-755, Published Online Jun. 10, 2003.
Tworoger et al. "Collection, Processing, and Storage of Biological Samples in Epidemiologic Studies: Sex Hormones, Carotenoids, Inflammatory Markers, and Proteomics as Examples", Cancer Epidemiol Biomarkers and Prevention, 15(9): 1578-1581, Sep. 2006.
Vapnik "Statistical Learning Theory", Adaptive and Learning Systems for Signal Processing, Communications, and Control, p. 1-732, 1998.
Vogel et al. "Sequence Signatures and mRNA Concentration Can Explain Two-Thirds of Protein Abundance Variation in A Human Cell Line", Molecular Systems Biology, 6(Art.400): 1-9, Published Online Aug. 24, 2010.
Wang et al. "Rotavirus Infection Alters Peripheral T-Cell Homeostasis in Children With Acute Diarrhea", Journal of Virology, 81(8): 3904-3912, Apr. 2007.
Whiteside et al. "Role of Human Natural Killer Cells in Health and Disease", Clinical and Diagnostic Laboratory Immunology, 1(2): 125-133, Mar. 31, 1994.
Xu et al. "Lipocalins as Biochemical Markers of Disease", Biochimica et Biophysica Acta, XP002376345, 1482(1): 298-307, Oct. 18, 2000. Abstract, Sections 3, 5, p. 303, col. 2-p. 304, col. l, Bridging Para, p. 304, cols. 1-2, Bidging Para, Fig. 1, Table 1.
Yamaji et al. "Significance of Eukaryotic Translation Elongation Factor 1A in Tobacco Mosaic Virus Infection", Archives of Virology. XP002663502, 155(2): 263-268, Feb. 2010. Abstract.
Yeung et al. "Serum Cytokines in Differentiating Between Viral and Bacterial Enterocolitis", Annals of Tropical Paediatrics, 24(4): 337-343, Published Online Jul. 18, 2013.
Zaas et al. "A Host-Based RT-PCR Gene Expression Signature to Identify Acute Respiratory Viral Infection", Science Translational Medicine, 5(203): 203ra126-1-203ra126-19, Sep. 18, 2013.
Zaas et al. "Gene Expression Signatures Diagnose Influenza and Other Symptomatic Respiratory Viral Infections in Humans", Cell Host & Microbe, XP002670360, 6(3): 207-217, Sep. 17, 2009. Abstract, p. 212, l-h col. p. 213, l-h col. Fig.4.
Zhu et al. "Use of Differential Display Analysis to Assess the Effect of Human Cytomegalovirus Infection on the Accumulation of Cellular RNAs: Induction of Interferon-Responsive RNAs", Proc. Natl. Acad. Sci. USA, XP002088235, 94(25): 13985-13990, Dec. 9, 1997. Abstract, Fig.2.
Zilliox et al. "Gene Expression Changes in Peripheral Blood Mononuclear Cells During Measles Virus Infection". Clinical and Vaccine Immunology, 14(7): 918-923, Jul. 2007.
Notice of Reason for Rejection dated Aug. 20, 2019 From the Japan Patent Office Re. Application No. 2017-507867 and Its Translation Into English. (5 Pages).

(56) References Cited

OTHER PUBLICATIONS

Office Action dated Jul. 30, 2020 From the Israel Patent Office Re. Application No. 261529 and Its Translation Into English. (5 Pages).
Office Action dated Jul. 30, 2020 From the Israel Patent Office Re. Application No. 261530 and Its Translation Into English. (5 Pages).
Restriction Official Action dated Jul. 30, 2020 from the US Patent and Trademark Office Re. U.S. Appl. No. 16/081,906. (7 pages).
Search Report and Opinion dated Aug. 20, 2019 From the Serviço Publico Federal, Ministerio da Economia, Institute National da Propriedade Industrial do Brasil Re. Application No. BR112014019733-4 and Its Summary in English. (4 Pages).
Translation Dated Sep. 11, 2019 of Notification of Office Action dated Aug. 22, 2019 From the State Intellectual Property Office of the People's Republic of China Re. Application No. 201580055946. 0. (1 Page).
Interview Summary dated Feb. 1, 2021 From the US Patent and Trademark Office Re. U.S. Appl. No. 16/687,726. (2 Pages).
Office Action dated Nov. 28, 2019 From the Israel Patent Office Re. Application No. 254095 and Its Translation Into English. (7 Pages).
Restriction Official Action dated Nov. 29, 2019 From the US Patent and Trademark Office Re. U.S. Appl. No. 16/238,582. (7 pages).
Translation of Reason for Rejection dated Nov. 21, 2019 of OA of Nov. 12, 2019 From the Japanese Patent Office Re. Application No. 2017-126712. (2 Pages).
Official Action dated Oct. 20, 2020 From the US Patent and Trademark Office Re. U.S. Appl. No. 16/081,069. (112 Pages).
ThermoFisher Scientific "Interferon Alpha Inducible Protein 27: IF127", ThermoFisher Scientific, Product Details, 2 P., 2020.
ThermoFisher Scientific "Interferon Induced Protein 44 Like: IF144L", ThermoFisher Scientific, Product Details, 2 P., 2020.
ThermoFisher Scientific "TaqMan Gene Expression Assay Solutions: Proven 5' Nuclease-Based Real-Time PCR Chemistry", Thermo Fisher Scientific, Applied Biosystems, 11 P., 2015.
Zaas et al. Supplementary Materials for "A Host-Based RT-PCR Gene Expression Signature to Identify Acute Respiratory Viral Infection", Science Translational Medicine, 5(203): 203ra126-1-203ra126-21, Sep. 18, 2013.
Ju et al. "Research Progress of Some Inflammatory Markers in Infectious Diseases", Chinese Journal of Practical Internal Medicine, 30(Suppl.l): 80-81, Jun. 2010. With an English Translation.
Communication Pursuant to Article 94(3) EPC dated Nov. 12, 2020 From the European Patent Office Re. Application No. 17759389.4. (6 Page).
Official Action dated Nov. 23, 2020 From the US Patent and Trademark Office Re. U.S. Appl. No. 16/355,984. (9 pages).
Patent Examination Report dated Feb. 8, 2021 From the Australian Government, IP Australia Re. Application No. 2015302870. (4 Pages).
Vapnik "Statistical Learning Theory", Adaptive and Learning Systems for Signal Processing, Communications, and Control, p. 1-732, 1998.—Part I.
Vapnik "Statistical Learning Theory", Adaptive and Learning Systems for Signal Processing, Communications, and Control, p. 1-732, 1998.—Part II.
Vapnik "Statistical Learning Theory", Adaptive and Learning Systems for Signal Processing, Communications, and Control, p. 1-732, 1998.—Part III.
Vapnik "Statistical Learning Theory", Adaptive and Learning Systems for Signal Processing, Communications, and Control, p. 1-732, 1998.—Part IV.
Communication Pursuant to Article 94(3) EPC dated May 25, 2020 From the European Patent Office Re. Application No. 11748712.4. (7 Pages).
Official Action dated May 15, 2020 from the US Patent and Trademark Office Re. U.S. Appl. No. 16/238,582. (92 pages).
Official Action dated May 7, 2020 from the US Patent and Trademark Office Re. U.S. Appl. No. 16/157,193. (23 pages).
Supplementary European Search Report and the European Search Opinion dated May 4, 2020 From the European Patent Office Re. Application No. 17855163.6. (9 Pages).

Ali et al. "Reliability of Serum Procalcitonin Concentrations for the Diagnosis of Sepsis in Neonates", Egypt Journal of Immunology, 15(1): 75-84, 2008. Abstract only.
Becker et al. "Procalcitonin in Sepsis and Systemic Inflammation: a Harmful Biomarker and a Therapeutic Target", British Journal of Pharmacology, 159: 253-264, 2010.
Forde et al. "The Beneficial Pleiotropic Effects of Tumour Necrosis Factor-Related Apoptosis-Inducing Ligand (TRAIL) Within the Vasculature: A Review of the Evidence", Atherosclerosis, XP029468976, 247: 87-96, Available Online Feb. 9, 2016.
Herzig et al. "The Role of CXCL10 in the Pathogenesis of Experimental Septic Shock", Critical Care, 18(3): 1-18, 2014.
Ng et al. "IP-10 Is an Early Diagnostic Marker for Identification of Late-Onset Bacterial Infection in Preterm Infants", Pediatric Research, 61(1): 93-98. 2007.
Povoa et al. "C-Reactive Protein, an Early Marker of Community-Acquired Sepsis Resolution: a Multi-Center Prospective Observational Study", Critical Care, 15(4): 1-10, 2011.
Sasaki et al. "Differentiating Between Bacterial and Viral Infection by Measuring Both C-Reactive Protein and 2'-5'-Oligoadenylate Synthetase as Inflammatory Markers", Journal of Infection and Chemotherapy, XP055696216, 8(1): 76-80, Mar. 2002.
Notification of Office Action and Search Report dated Jul. 28, 2020 From the State Intellectual Property Office of the People's Republic of China Re. Application No. 201810781584.9 and Its Translation of Office Action Into English.
Bai et al. "A New Early Diagnostic Marker for Inflammatory Diseases—sTREM-1", International Journal of Pathology and Clinical Medicine, 27(1): 73-76, Feb. 2007.
Cai et al. "The Study on the Relationship Between PCT and CRP in Infective Diseases", Journal of Qiqihar University of Medicine, 32(5): 696-697, 2011.
Requisition by the Examiner dated Dec. 7, 2020 From the Innovation, Science and Economic Development Canada, Canadian Intellectual Property Office Re. Application No. 2,863,819. (4 Pages).
Restriction Official Action dated Dec. 9, 2020 from the US Patent and Trademark Office Re. U.S. Appl. No. 16/336,528. (7 pages).
Communication Pursuant to Article 94(3) EPC dated Jul. 31, 2019 From the European Patent Office Re. Application No. 18162713.4. (4 Pages).
Ludwig et al. "Tumor Necrosis Factor Related Apoptosis Inducing Ligand: A Novell Mechanism for Bacillus Calmette Guerin Induced Antitumor Activity" Cancer Research 64: 3386-3390, May 15, 2004.
Official Action dated Dec. 30, 2020 from the US Patent and Trademark Office Re. U.S. Appl. No. 16/334,033. (112 pages).
Bone et al. "Definitions for Sepsis and Organ Failure and Guidelines for the Use of Innovative Therapies in Sepsis", Chest, 101(6): 1644-1655, 1992.
Kang et al. "Low serum TNF-Related Apoptosis-Inducing Ligand (TRAIL) Levels Are Associated with Acute Ischemic Stroke Severity", Atherosclerosis, 240: 228-233, 2015.
Michowitz et al. "The Involvement of Tumor Necrosis Factor-Related Apoptosis-Inducing Ligand (TRAIL) in Atherosclerosis.", Journal of the American College of Cardiology, 45(7): 1018-1024, 2005.
Osmancik et al. "Prognostic Value of TNF-Related Apoptosis Inducing Ligand (TRAIL) in Acute Coronary Syndrome Patients", PLoS One, 8(2): e53860, 2013.
Volpato et al. "Association of Tumor Necrosis Factor-Related Apoptosis-Inducing Ligand with Total and Cardiovascular Mortality in Older Adults", Atherosclerosis, 215:452-458, 2011.
Official Action dated Nov. 4, 2020 From the US Patent and Trademark Office Re. U.S. Appl. No. 16/238,582. (37 Pages).
Applicant-Initiated Interview Summary dated Feb. 10, 2020 From the US Patent and Trademark Office Re. U.S. Appl. No. 16/157,193. (3 pages).
Supplementary European Search Report and the European Search Opinion dated Feb. 18, 2020 From the European Patent Office Re. Application No. 17827121.9. (5 Pages).
Restriction Official Action dated Dec. 5, 2019 From the US Patent and Trademark Office Re. U.S. Appl. No. 16/081,906. (9 pages).

(56) References Cited

OTHER PUBLICATIONS

Examination Report Under Sections 12 & 13 of the Patents Act, 1970 and the Patents Rules, 2003 dated Oct. 21, 2019 From the Government of India, Intellectual Property India, Patents, Designs, Trade Marks, Geographical Indications Re. Application No. 9122/DELNP/2012 (5 Pages).
Notice of Reason for Rejection dated Nov. 12, 2019 From the Japan Patent Office Re. Application No. 2017-126712 and an English Summary. (3 Pages).
Official Action dated Oct. 15, 2019 From the US Patent and Trademark Office Re. Application No. 151713,722. (57 Pages).
Official Action dated Sep. 16, 2019 From the US Patent and Trademark Office Re. U.S. Appl. No. 16/355,984. (44 pages).
Official Action dated Sep. 18, 2019 From the US Patent and Trademark Office Re. U.S. Appl. No. 16/157,193. (30 pages).
Official Action dated Oct. 24, 2019 From the US Patent and Trademark Office Re. U.S. Appl. No. 15/531,747. (37 Pages).
Requisition by the Examiner dated Oct. 4, 2019 From the Innovation, Science and Economic Development Canada, Canadian Intellectual Property Office Re. Application No. 2,863,819. (3 Pages).
Supplementary European Search Report and the European Search Opinion dated Sep. 30, 2019 From the European Patent Office Re. Application No. 17759388.6. (11 Pages).
Supplementary Partial European Search Report and the European Provisional Opinion Dated Oct. 24, 2019 From the European Patent Office Re. Application No. 17759389.4. (15 Pages).
Translation Dated Sep. 22, 2019 of Search Report and Opinion dated Aug. 20, 2019 From the Servi?o Publico Federal, Ministerio da Economia, Instituto Nacional da Propriedade Industrial do Brasil Re. Application No. BR112014 019733-4 and Its Summary in English. (4 Pages).
Barnhart et al. "Changes in Cellular mRNA Stability, Splicing, and Polyadenylation Through HuR Protein Sequestration by A Cytoplasmic RNA Virus", Cell Reports, XP055621573, 5(4): 909-917, Nov. 27, 2013.
Consiglio et al. "BEAT: Bioinformatics Exon Array Tool to Store, Analyze and Visualize Affymetrix GeneChip Human Exon Array Data From Disease Experiments", BMC Bioinformatics, XP021117755, 13(Suppl.4): S21-1-S21-14, Mar. 28, 2012.
UCSC "UCSC Browser on Human Feb. 2009 (GRCh37/hg19) Assembly: Showing Location of Probes on the Affymetrix ExonChip Binding to Exons of ANKRD22", UCSC Browser, XP055621243, Retrieved From the Internet, 7 P., Jan. 2009.
UCSC "UCSC Genome Browser on Human Feb. 2009 (GRCh37/hg19) Assembly: Showing Location of Probes on the Affymetrix ExonChip Binding to Exons of AIM2", UCSC Browser, XP055621240, Retrieved From the Interent, 8 P., Jan. 2009.
Zaas et al. "The Current Epidemiology and Clinical Decisions Surrounding Acute Respiratory Infections", Trends in Molecular Medicine, XP055522333, 20(10): 579-588, Published Online Sep. 5, 2014.
Communication Pursuant to Article 94(3) EPC dated May 7, 2019 From the European Patent Office Re. Application No. 15831781.8. (3 Pages).
Examination Report dated May 29, 2019 From the Australian Government, IP Australia Re. Application No. 2018202302. (5 Pages).
Notification of Office Action dated Jun. 3, 2019 From the China National Intellectual Property Administration Re. Application No. 201610817276.8 and Its Translation Into English. (10 Pages).
Communication Pursuant to Article 94(3) EPC dated Jun. 4, 2020 From the European Patent Office Re. Application No. 17759388.6. (3 Pages).
Supplementary European Search Report and the European Search Opinion dated May 18, 2020 From the European Patent Office Re. Application No. 17855164.4. (13 Pages).
Shommu et al. "Metabolomic and Inflammatory Mediator Based Biomarker Profiling as A Potential Novel Method to Aid Pediatric Appendicitis Identification", PLOS ONE, XP055692841, 13(3): e0193563-1-e0193563-13, Mar. 12, 2018.

Communication Pursuant to Article 94(3) EPC dated Aug. 18, 2020 From the European Patent Office Re. Application No. 11748712.4. (3 Pages).
Communication Pursuant to Article 94(3) EPC dated Mar. 25, 2020 From the European Patent Office Re. Application No. 18162713.4. (5 Pages).
Communication Pursuant to Article 94(3) EPC dated Mar. 27, 2020 From the European Patent Office Re. Application No. 15868614.7. (6 Pages).
Official Action dated Mar. 26, 2020 from the US Patent and Trademark Office Re. U.S. Appl. No. 16/687,726. (47 pages).
Official Action dated Mar. 31, 2020 from the US Patent and Trademark Office Re. U.S. Appl. No. 15/531,747. (21 pages).
Restriction Official Action dated Apr. 2, 2020 from the US Patent and Trademark Office Re. U.S. Appl. No. 16/081,069. (7 pages).
Greenspan et al. "Defining Epitopes: It's Not As Easy As It Seems", Nature Biotechnology, 17: 936-937, Oct. 1999.
Lloyd et al. "Modelling The Human Immune Response: Performance Of A 1011 Human Antibody Repertoire Against A Broad Panel Of Therapeutically Relevant Antigens", Protein Engineering, Design & Selection 22(3): 159-168, Oct. 29, 2008.
Rudikoff et al. "Single Amino Acid Substitution Altering Antigen-Binding Specificity", PNAS, 79(6): 1979-1983, Mar. 1982.
Advisory Action Before the Filing of An Appeal Brief dated Dec. 23, 2019 From the US Patent and Trademark Office Re. U.S. Appl. No. 16/157,193. (3 pages).
Final Official Action dated Sep. 8, 2020 from the US Patent and Trademark Office Re. U.S. Appl. No. 16/687,726. (28 pages).
Official Action dated Mar. 5, 2020 From the US Patent and Trademark Office Re. U.S. Appl. No. 15/713,722. (24 pages).
Requisition by the Examiner dated Jul. 30, 2021 From the Innovation, Science and Economic Development Canada, Canadian Intellectual Property Office Re. Application No. 2,954,601. (4 Pages).
Communication Pursuant to Article 94(3) EPC dated Jun. 2, 2021 From the European Patent Office Re. Application No. 17827121.9. (5 Pages).
Communication Pursuant to Article 94(3) EPC dated Mar. 17, 2021 From the European Patent Office Re. Application No. 15868614.7. (5 Pages).
Restriction Official Action dated Mar. 29, 2021 From the US Patent and Trademark Office Re. U.S. Appl. No. 16/081,069. (8 Pages).
European Search Report and the European Search Opinion dated Jul. 14, 2021 From the European Patent Office Re. Application No. 21170448.1. (6 Pages).
Notice of Allowance Dated and Interview Summary dated Jul. 19, 2021 from the US Patent and Trademark Office Re. U.S. Appl. No. 16/687,726. (24 pages).
Translation Dated Jul. 22, 2021 of Notification of Office Action dated Jul. 13, 2021 From the State Intellectual Property Office of the People's Republic of China Re. Application No. 20180781584.9. (2 Pages).
Translation Dated Jul. 27, 2021 of Notification of Office Action dated Jul. 2, 2021 From the State Intellectual Property Office of the People's Republic of China Re. Application No. 201780055014.5. (12 Pages).
Notice of Reasons for Rejection dated Apr. 20, 2021 From the Japan Patent Office Re. Application No. 2020-021606 and Its Translation Into English. (9 Pages).
Official Action dated May 5, 2021 From the US Patent and Trademark Office Re. U.S. Appl. No. 16/336,528. (108 Pages).
Brost et al. "Differential Expression of the TRAIL/TRAIL-receptor System in Patients with Inflammatory Bowel Disease", Pathology—Research and Practice, 206(1):43-50, Jan. 15, 2010.
Notification of Office Action and Search Report dated Jun. 3, 2021 From the State Intellectual Property Office of the People's Republic of China Re. Application No. 20180014541.1 and Its Translation Into English. (17 Pages).
Notification of Office Action and Search Report dated Jul. 2, 2021 From the State Intellectual Property Office of the People's Republic of China Re. Application No. 201780055014.5. (23 Pages).

(56) References Cited

OTHER PUBLICATIONS

Notification of Office Action and Search Report dated Jul. 13, 2021 From the State Intellectual Property Office of the People's Republic of China Re. Application No. 20180781584.9 and an English Summary. (4 Pages).
Final Official Action dated Jun. 15, 2021 From the US Patent and Trademark Office Re. U.S. Appl. No. 16/334,033. (36 Pages).
Notice of Reason(s) for Rejection dated Jun. 15, 2021 From the Japan Patent Office Re. Application No. 2020-109710 and Its Translation Into English. (12 Pages).
Examination Report Under Sections 12 & 13 of the Patents Act, 1970 and the Patents Rules, 2003 dated Mar. 31, 2021 From the Government of India, Intellectual Property India, Patents, Designs, Trade Marks, Geographical Indications, The Patent Office Re. Application No. 201727005513. (7 Pages).
Notice of Allowance dated Apr. 19, 2021 from the US Patent and Trademark Office Re. U.S. Appl. No. 16/238,582. (22 pages).
Bloos et al. "Rapid Diagnosis of Sepsis"; Virulence, 5(1): 154-160, 2014.
Henriquez-Camacho et al. "Biomarkers for Sepsis"; BioMed Research International, 547818: 6 pages, 2014.
Notification of Office Action and Search Report dated Feb. 20, 2021 From the State Intellectual Property Office of the People's Republic of China Re. Application No. 201780014568.0. (9 Pages).
Notification of Office Action dated Mar. 5, 2021 From the State Intellectual Property Office of the People's Republic of China Re. Application No. 201810781584.9 and Its Translation of Office Action Into English. (13 Pages).
Official Action dated Mar. 10, 2021 From the US Patent and Trademark Office Re. U.S. Appl. No. 16/081,906. (127 Pages).
Shair et al. "Epstein-Barr Virus Latent Membrane Protein-1 Effects on Junctional Plakoglobin and Induction of a Cadherin Switch", Cancer Research, Cell, Tumor, and Stem Cell Biology, 69(14): 5734-5742, Jul. 15, 2009.
Final Official Action dated Nov. 29 together with Interview Summary dated Nov. 14, 2021 from US Patent and Trademark Office Re. U.S. Appl. No. 16/081,906. (45 pages).
Interview Summary dated Dec. 3, 2021 from US Patent and Trademark Office Re. U.S. Appl. No. 16/081,069. (3 pages).

Notification of Office Action and Search Report dated Sep. 30, 2021 From the State Intellectual Property Office of the People's Republic of China Re. Application No. 201780073531.5 and Its Translation of Office Action Into English. (14 Pages).
Official Action dated Nov. 22, 2021 from the US Patent and Trademark Office Re. U.S. Appl. No. 16/998,006. (116 pages).
Requisition by the Examiner dated Nov. 5, 2021 From the Innovation, Science and Economic Development Canada, Canadian Intellectual Property Office Re. Application No. 2,968,650. (7 Pages).
Ioannidis et al. "Plasticity and Virus Specifity of the Airway Epithelial Cell Immune Response During Respiratory Virus Infection", Journal of Virology. 86(10): 5422-36, Mar. 7, 2012.
Zhang "Research Progress of Interferon-Inducible Protein 10 and Its Effect in Newborn Infection Diagnosis", Chinese Journal of Neonatology. 4: 60-62, Jul. 15, 2013.
European Search Report and the European Search Opinion dated Oct. 6, 2021 From the European Patent Office Re. Application No. 21178885.6. (10 Pages).
Final Official Action dated Sep. 10, 2021 from the US Patent and Trademark Office Re. U.S. Appl. No. 16/081,069. (61 pages).
Notification of Office Action and Search Report dated Aug. 3, 2021 From the State Intellectual Property Office of the People's Republic of China Re. Application No. 201780055347.8 and Its Translation of Office Action Into English. (526Pages).
Notification of Office Action dated Sep. 1, 2021 From the State Intellectual Property Office of the People's Republic of China Re. Application No. 201780014568.0 and Its Translation Into English. (7 Pages).
Affymetrix "Whole-Transcript Expression Analysis", Affymetrix, 8 pages, 2007.
New England Biolabs "New England Biolabs Catalog", New England Biolabs, 1-4 pages, 1996.
Rothstein et al. "Chronic Inhibition of Superoxide Dismutase Produces Apoptotic Death of Spinal Neurons", PNAS, (10): 4155-4159, May 1994.
Zhang et al. "Expression of Tumor Necrosis Factor-Related Apoptosis-Inducing Ligand in Serum of Severe Hepatitis Patients with Nosocomial Infections and its Clinical Significance", Chinese Journal of Nosocomiology, 24, Abstract, 2012.

\* cited by examiner

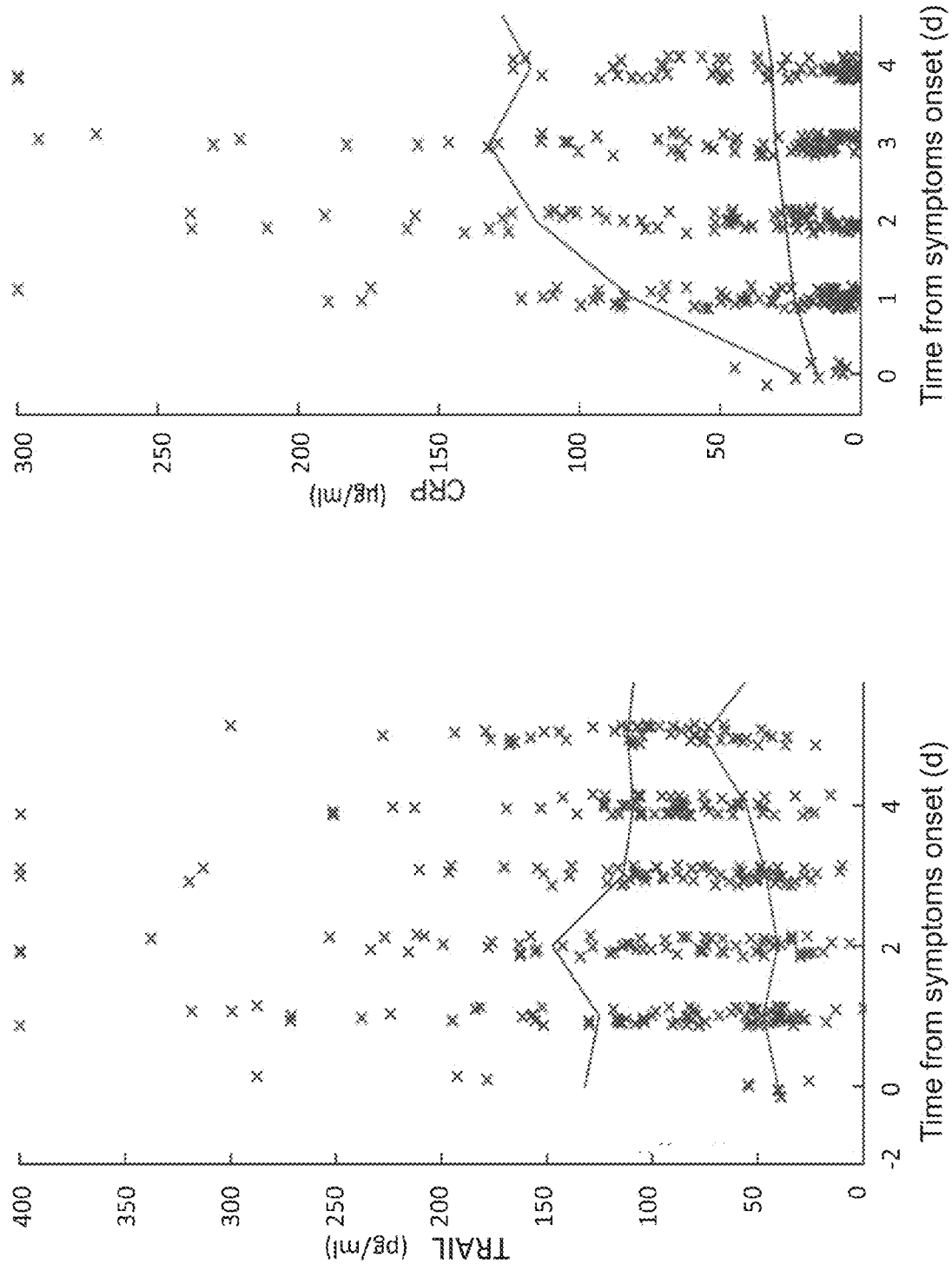

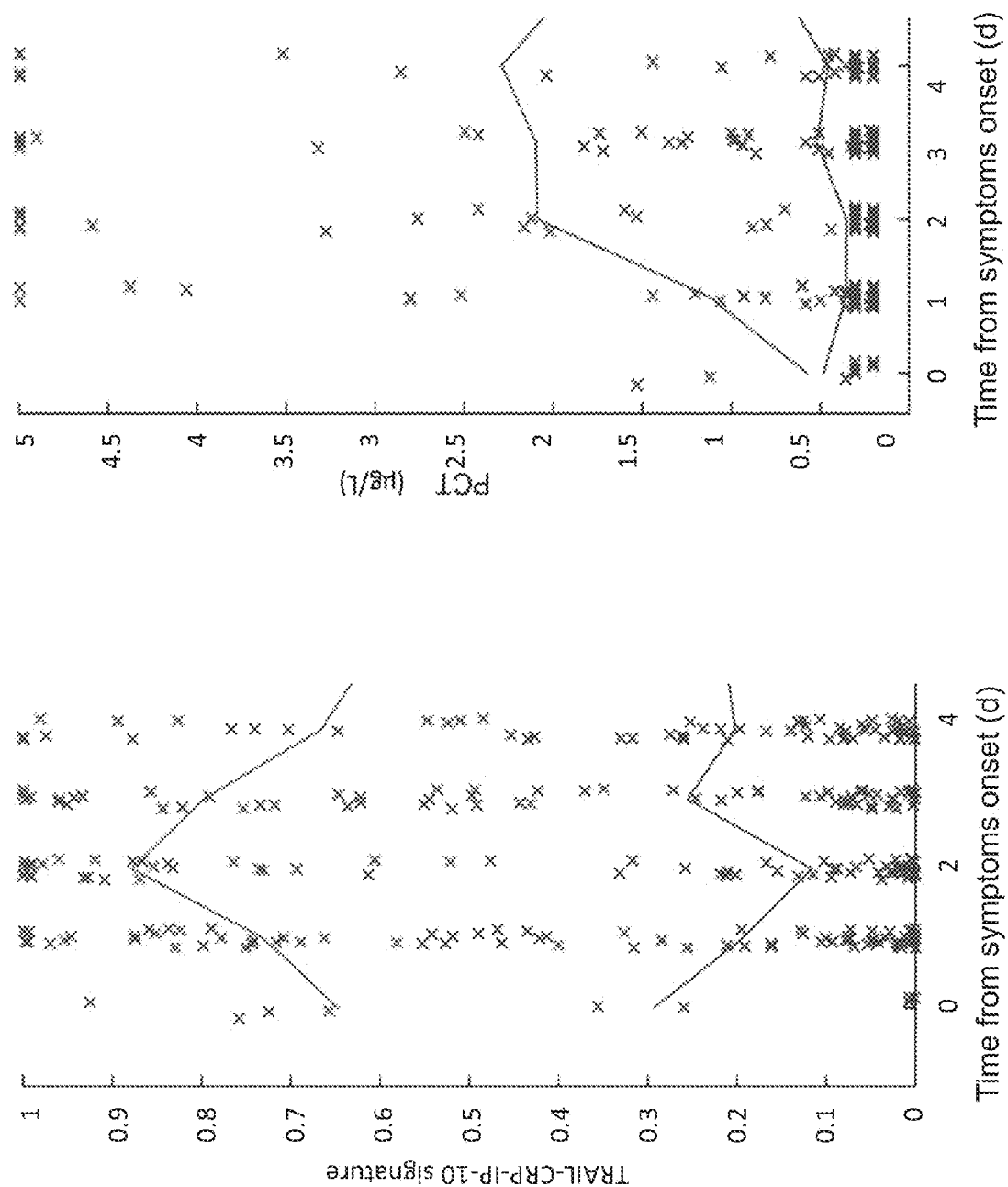

EARLY DIAGNOSIS OF INFECTIONS

RELATED APPLICATIONS

This application is a National Phase of PCT Patent Application No. PCT/IL2017/050781 having International filing date of Jul. 10, 2017, which claims the benefit of priority under 35 USC § 119(e) of U.S. Provisional Patent Application No. 62/360,420 filed on Jul. 10, 2016. The contents of the above applications are all incorporated by reference as if fully set forth herein in their entirety.

FIELD AND BACKGROUND OF THE INVENTION

Sequence Listing Statement

The ASCII file, entitled 75587SequenceListing.txt, created on Jan. 10, 2019, comprising 58,461 bytes, submitted concurrently with the filing of this application is incorporated herein by reference. The sequence listing submitted herewith is identical to the sequence listing forming part of the international application.

The present invention, in some embodiments thereof, relates to the identification of signatures and determinants associated with bacterial and viral infections. More specifically, it was discovered that the protein TRAIL is a particularly accurate determinant when it is analyzed less than two days following symptom onset.

Antibiotics are the world's most prescribed class of drugs with a 25-30 billion $US global market. Antibiotics are also the world's most misused drug with a significant fraction of all drugs (40-70%) being wrongly prescribed.

One type of antibiotic misuse is when the drug is administered in case of a non-bacterial disease, such as a viral infection, for which antibiotics are ineffective. For example, according to the USA center for disease control and prevention CDC, over 60 Million wrong antibiotic prescriptions are given annually to treat flu in the US. The health-care and economic consequences of the antibiotic over-prescriptions include: (i) the cost of antibiotics that are unnecessarily prescribed globally, estimated at >$10 billion annually; (ii) side effects resulting from unnecessary antibiotics treatment are reducing quality of healthcare, causing complications and prolonged hospitalization (e.g. allergic reactions, Antibiotics-associated diarrhea, intestinal yeast etc.) and (iii) the emergence of resistant strains of bacteria as a result of the overuse.

Resistance of microbial pathogens to antibiotics is increasing world-wide at an accelerating rate ("CDC—Get Smart: Fast Facts About Antibiotic Resistance" 2013; "European Surveillance of Antimicrobial Consumption Network (ESAC-Net)" 2014; "CDC—About Antimicrobial Resistance" 2013; "Threat Report 2013|Antimicrobial Resistance|CDC" 2013), with a concomitant increase in morbidity and mortality associated with infections caused by antibiotic resistant pathogens ("Threat Report 2013|Antimicrobial Resistance|CDC" 2013). At least 2 million people are infected with antibiotic resistant bacteria each year in the US alone, and at least 23,000 people die as a direct result of these infections ("Threat Report 2013|Antimicrobial Resistance|CDC" 2013). In the European Union, an estimated 400,000 patients present with resistant bacterial strains each year, of which 25,000 patients die ("WHO Europe—Data and Statistics" 2014). Consequently, the World Health Organization has warned that therapeutic coverage will be insufficient within 10 years, placing the world at risk of entering a "post-antibiotic era", in which antibiotics will no longer be effective against infectious diseases ("WHO|Antimicrobial Resistance" 2013). The CDC considers this phenomenon "one of the world's most pressing health problems in the $21^{st}$ century" ("CDC—About Antimicrobial Resistance" 2013).

Antibiotic under-prescription is not uncommon either. For example, up to 15% of adult bacterial pneumonia-hospitalized patients in the US receive delayed or no Abx treatment, even though in these instances early treatment can save lives and reduce complications.

Technologies for infectious disease diagnostics have the potential to reduce the associated health and financial burden associated with antibiotics misuse. Ideally, such a technology should: (i) accurately differentiate between a bacterial and viral infections; (ii) be rapid (within minutes); (iii) be able to differentiate between pathogenic and non-pathogenic bacteria that are part of the body's natural flora; (iv) differentiate between mixed co-infections and pure viral infections and (v) be applicable in cases where the pathogen is inaccessible (e.g. sinusitis, pneumonia, otitis-media, bronchitis, etc).

Correct identification of bacterial patients is of high importance as these patients require antibiotic treatment and in some cases more aggressive management (hospitalization, additional diagnostic tests etc). Misclassification of bacterial patients increases the chance of morbidity and mortality. Therefore, increasing the sensitivity of a diagnostic test that distinguishes between bacterial and viral infections is desired, even at a cost of reduced specificity.

Additional background art includes US Patent Application No. 20080171323, WO2011/132086 and WO2013/117746.

SUMMARY OF THE INVENTION

According to an aspect of some embodiments of the present invention there is provided a method of ruling in a bacterial infection in a subject showing symptoms of an infection, the method comprising measuring the amount of TRAIL in a blood sample being derived from the subject no more than two days following symptom onset, wherein when the amount of the TRAIL is below a first predetermined level, a bacterial infection is ruled in.

According to an aspect of some embodiments of the present invention there is provided a method of determining a treatment regimen in a subject showing symptoms of a pathogenic infection comprising measuring the amount of TRAIL in a blood sample, the blood sample being derived from the subject no more than two days following symptom onset, wherein when the amount of the TRAIL is below a first predetermined level, the subject is recommended an anti-bacterial agent.

According to an aspect of some embodiments of the present invention there is provided a method of classifying an infection type of a subject comprising:

(a) analyzing for the presence of specific pathogen in a sample of the subject; and (b) measuring the amount of TRAIL in a sample of the subject, wherein the presence of the specific pathogen and the amount of TRAIL is indicative of the infection type.

According to an aspect of some embodiments of the present invention there is provided a method of distinguishing between an infectious exacerbation state and a non-infectious exacerbation state of chronic obstructive pulmonary disease (COPD) or asthma of a subject comprising measuring the amount of TNF-related apoptosis-inducing ligand (TRAIL) in a blood sample derived from the subject, wherein the amount is indicative of the infectivity of the exacerbation state of COPD or asthma.

According to an aspect of some embodiments of the present invention there is provided a method of treating a subject showing symptoms of an infection comprising:

(a) determining a treatment regimen as described herein and;

(b) treating the subject according to the results of the determining.

According to an aspect of some embodiments of the present invention there is provided a method of diagnosing an infection in a subject showing symptoms of an infection, the method comprising measuring the amount of IP10 in a blood sample being derived from the subject no more than two days following symptom onset, wherein the amount of the IP10 is indicative of the infection.

According to some embodiments of the invention, the bacterial infection is a group a streptococcal infection.

According to some embodiments of the invention, the amount of TRAIL is above a second predetermined level, a viral infection is ruled in.

According to some embodiments of the invention, the amount of TRAIL is above a second predetermined level, the subject is recommended an anti-viral agent.

According to some embodiments of the invention, the specific pathogen is selected from the group consisting of Influenza, Respiratory syncytial virus (RSV), Rhinovirus and Group A *Streptococcus*.

According to some embodiments of the invention, the infection type comprises a pathogenic infection or a non-pathogenic infection.

According to some embodiments of the invention, step (a) is effected following step (b).

According to some embodiments of the invention, step (b) is effected following step (a).

According to some embodiments of the invention, the level is 70 pg/ml.

According to some embodiments of the invention, the subject has a normal level of creatine kinase.

According to some embodiments of the invention, the first predetermined level and the second predetermined level are identical.

According to some embodiments of the invention, the first predetermined level and the second predetermined level are non-identical.

According to some embodiments of the invention, the symptoms of an infection comprise fever.

According to some embodiments of the invention, the symptoms of a pathogenic infection comprise fever.

According to some embodiments of the invention, the sample is derived from the subject no more than one day following symptom onset.

According to some embodiments of the invention, the sample is whole blood or a fraction thereof.

According to some embodiments of the invention, the fraction comprises serum.

According to some embodiments of the invention, the blood fraction sample comprises cells selected from the group consisting of lymphocytes, monocytes and granulocytes.

According to some embodiments of the invention, the method further comprises analyzing a level of C-reactive protein (CRP) and/or Interferon gamma-induced protein 10 (IP10).

According to some embodiments of the invention, the method further comprises analyzing a level of a polypeptide selected from the group consisting of Interferon gamma-induced protein 10 (IP10), Interleukin 6 (IL-6), and Interleukin 1 receptor, type I (IL1RA).

According to some embodiments of the invention, the method further comprises analyzing a level of a polypeptide selected from the group consisting of Interferon gamma-induced protein 10 (IP10), Interleukin 6 (IL-6), Interleukin 1 receptor, type I (IL1RA), C-reactive protein (CRP) and procalcitonin (PCT).

According to some embodiments of the invention, the TRAIL is measured using a lateral flow immunoassay.

According to some embodiments of the invention, the TRAIL is measured using an antibody which binds specifically to TRAIL.

According to some embodiments of the invention, the antibody is a monoclonal antibody.

According to some embodiments of the invention, the treating comprises administering to the subject a therapeutically effective amount of an anti-bacterial agent.

According to some embodiments of the invention, the anti-bacterial agent is an antibiotic.

According to some embodiments of the invention, when the amount is above a predetermined level a viral infection is ruled in.

According to some embodiments of the invention, when the amount is below a predetermined level, an infection is ruled out.

According to some embodiments of the invention, the method further comprises analyzing a level of a polypeptide selected from the group consisting of TRAIL, Interleukin 6 (IL-6), and Interleukin 1 receptor, type I (IL1RA).

According to some embodiments of the invention, the method further comprises analyzing a level of a polypeptide selected from the group consisting of Interferon gamma-induced protein 10 (IP10), Interleukin 6 (IL-6), Interleukin 1 receptor, type I (IL1RA), C-reactive protein (CRP) and procalcitonin (PCT).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL
VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1: Clinical study workflow.

Figure 2:
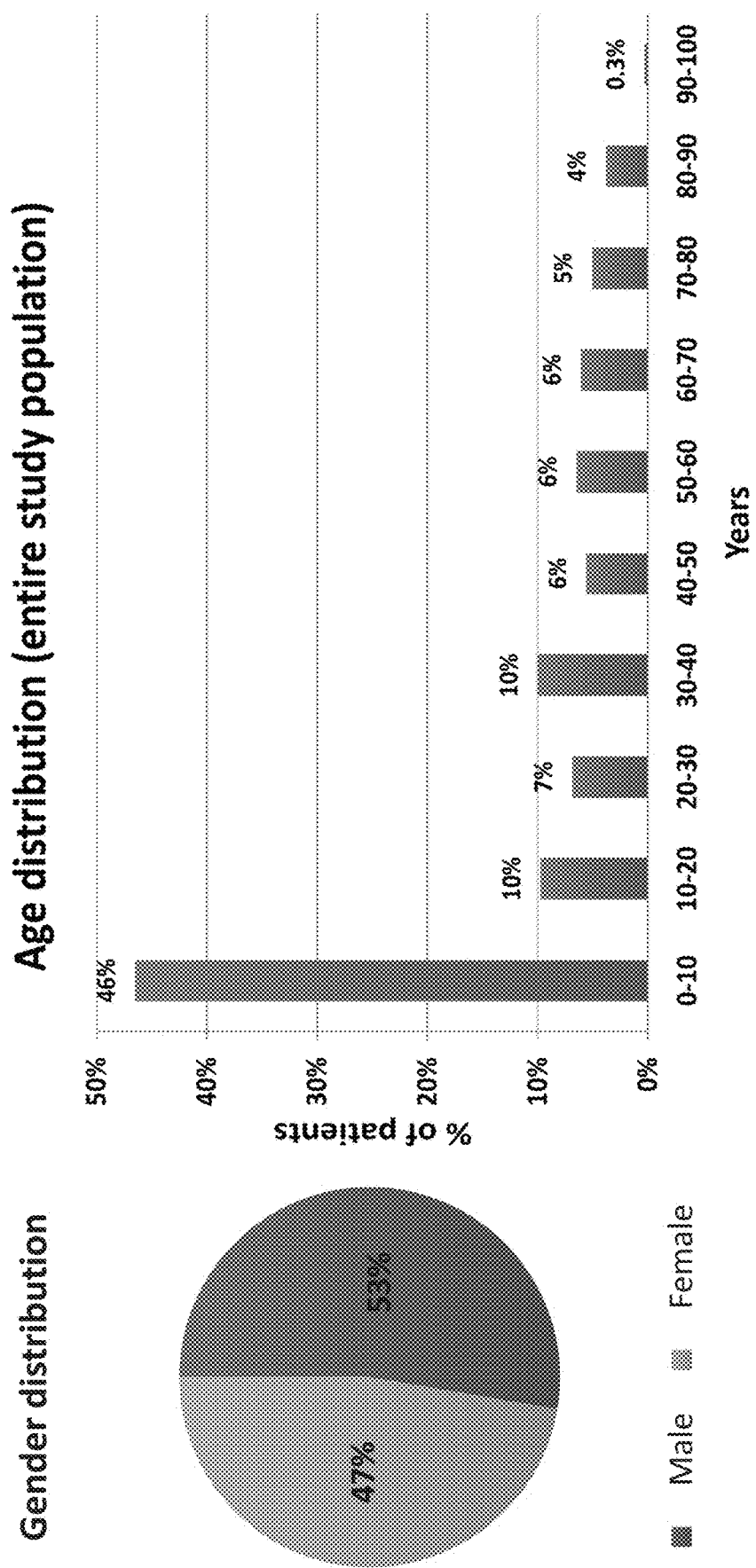

FIG. 2: Distribution of age and gender of the patients enrolled in the clinical study.

Figure 3:
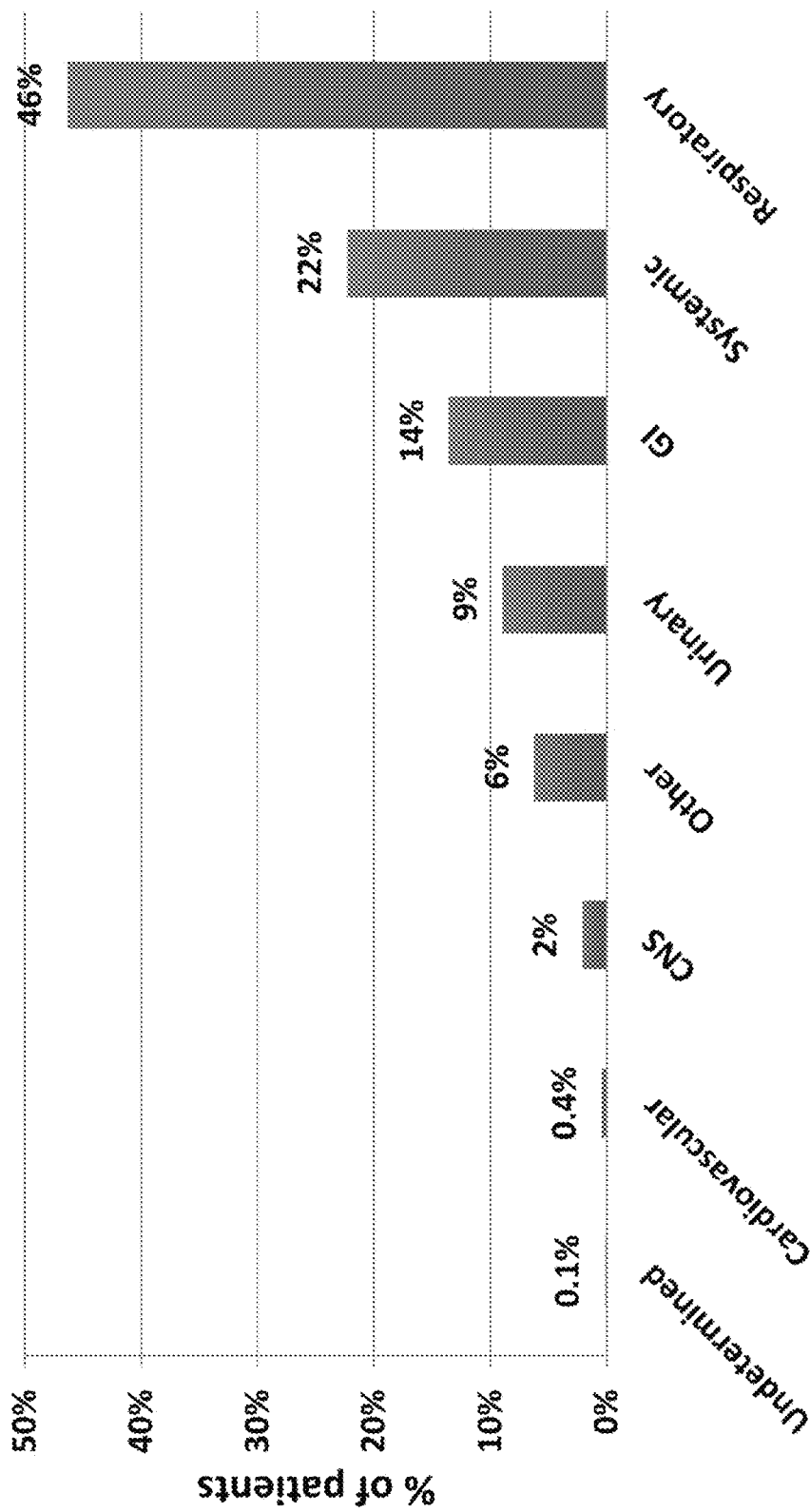
Figure 4:
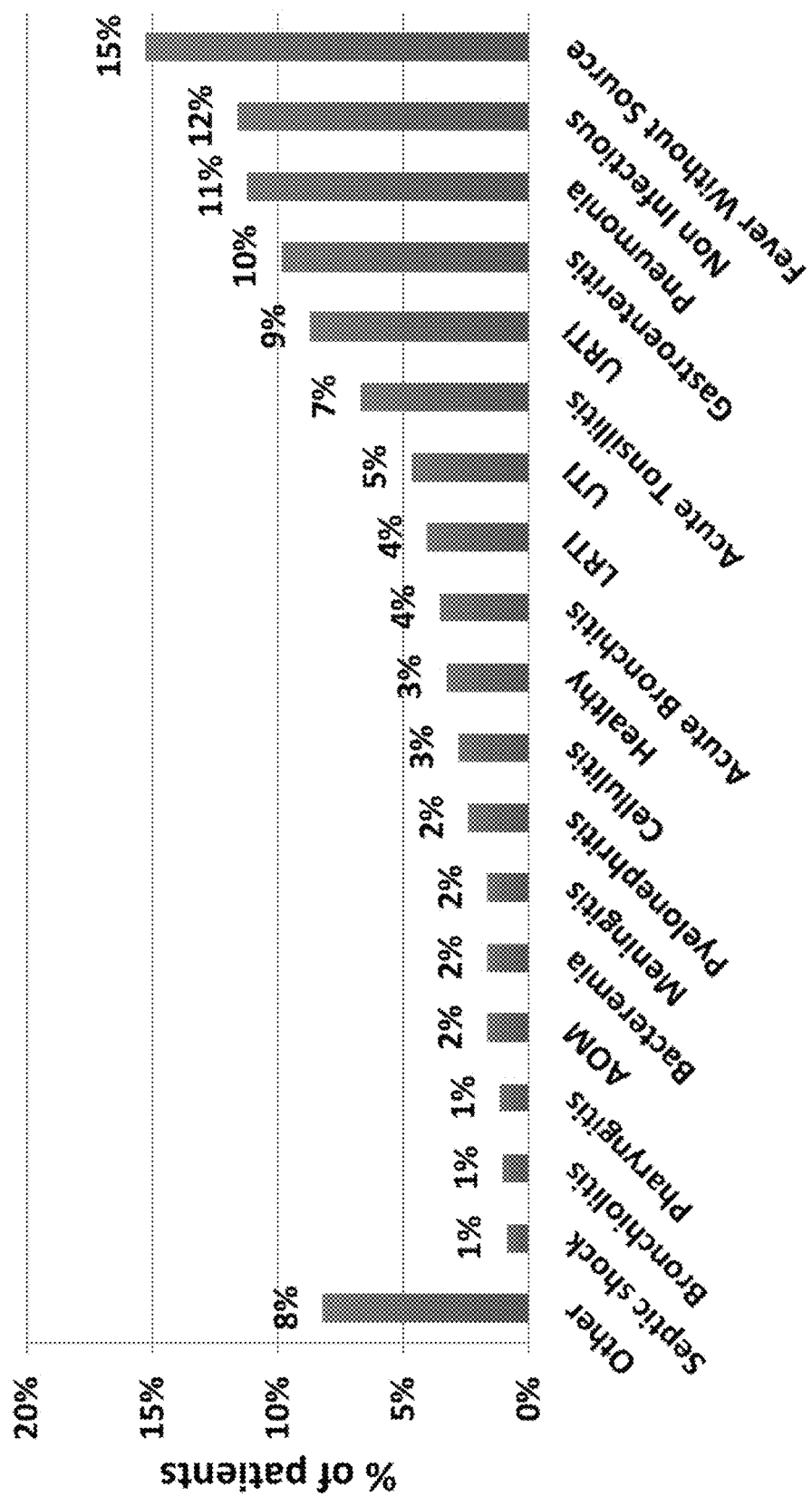

FIG. 3: Distribution of physiological systems of the infectious disease patients enrolled in the clinical study.

FIG. 4: Distribution of major clinical syndromes of the infectious disease patients enrolled in the clinical study.

Figure 5:
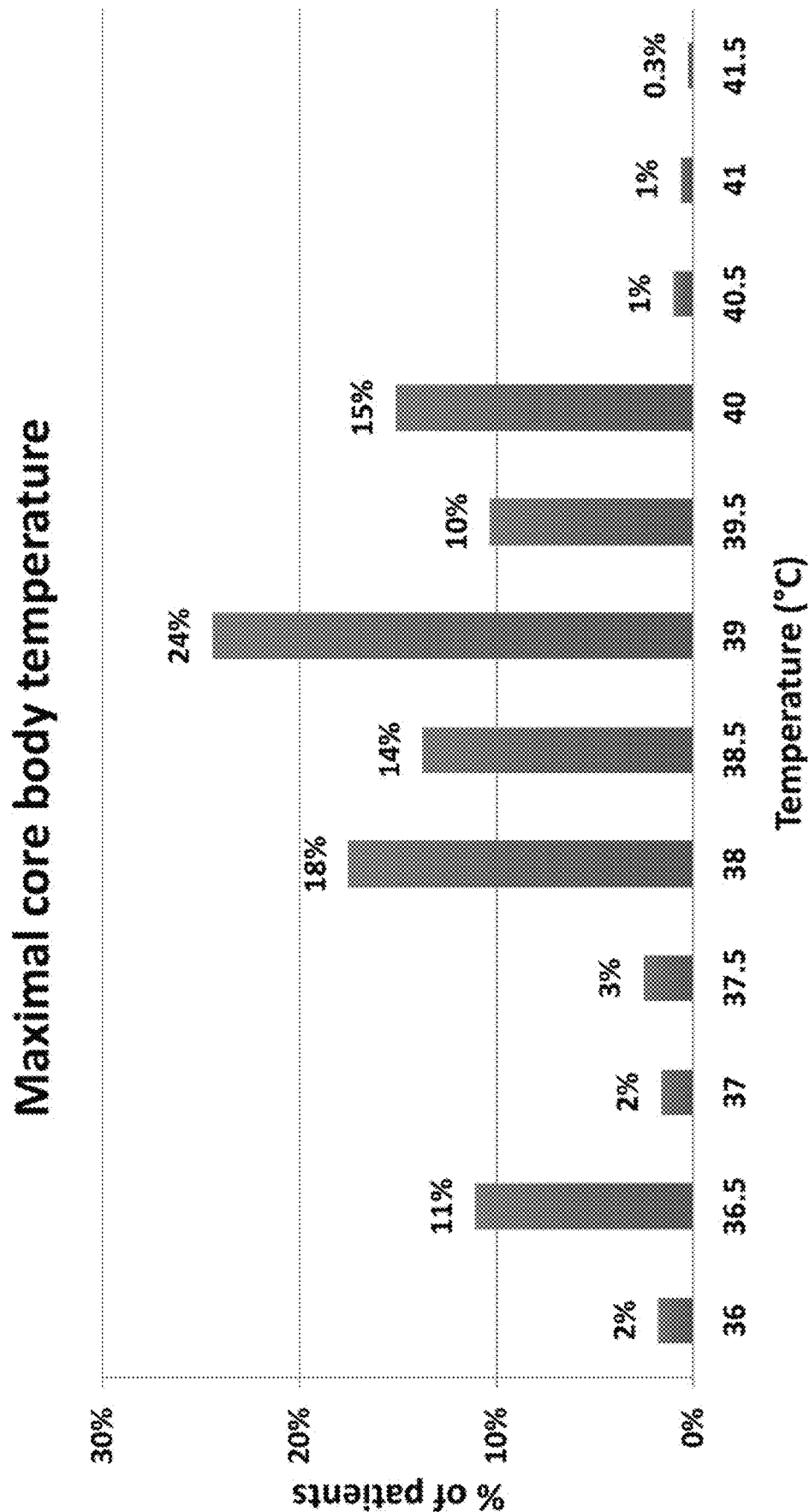

FIG. 5: Distribution of maximal body temperatures of the infectious disease patients enrolled in the clinical study.

Figure 6:
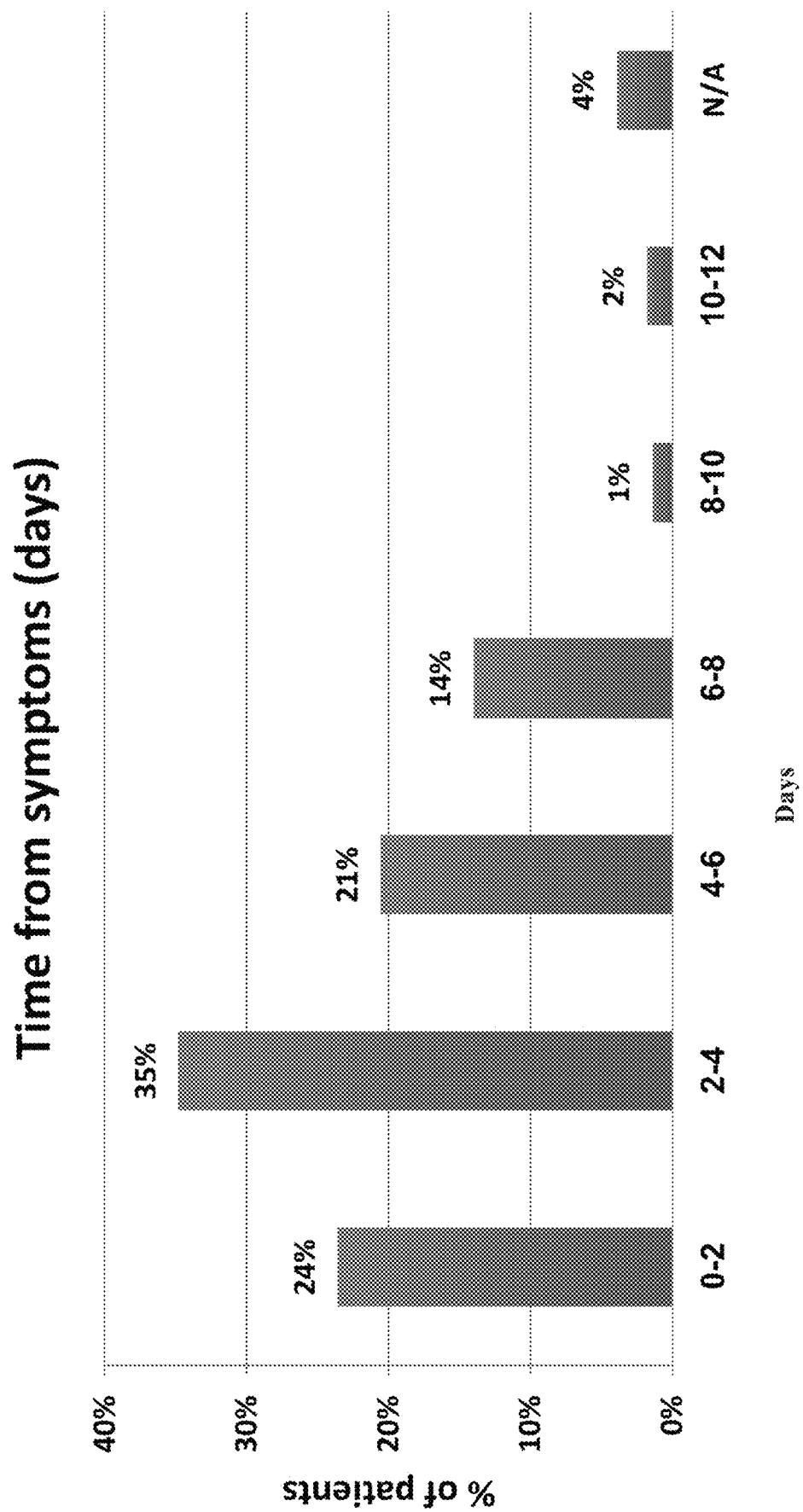

FIG. 6: Distribution of time from initiation of symptoms of the infectious disease patients enrolled in the clinical study.

Figure 7:
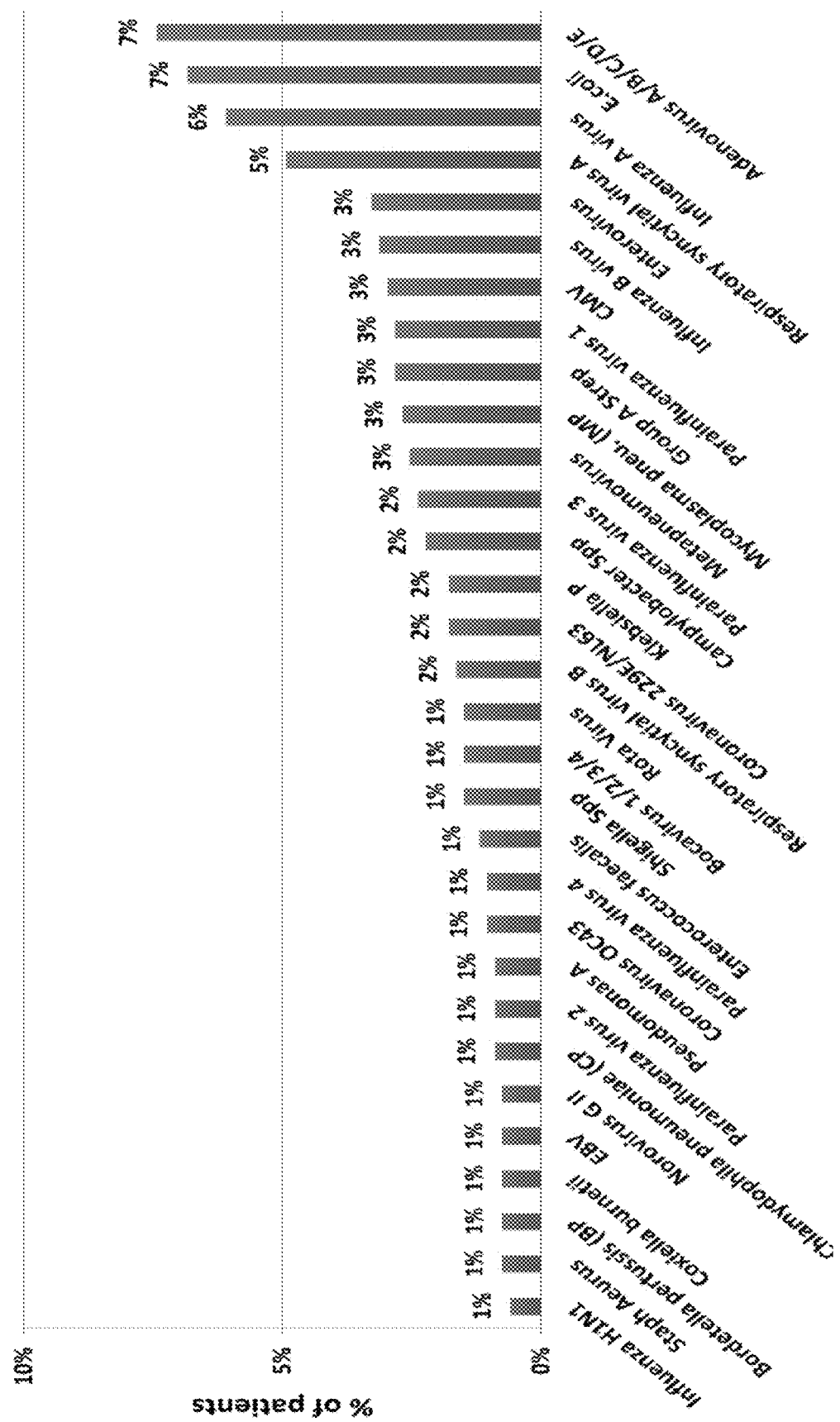

FIG. 7: Pathogen isolated from infectious disease patients enrolled in the clinical study FIG. 8: TRAIL is differentially expressed in bacterial, viral and non-infectious patients (n=765). Red line and circle correspond to group median and average respectively.

Figure 9:
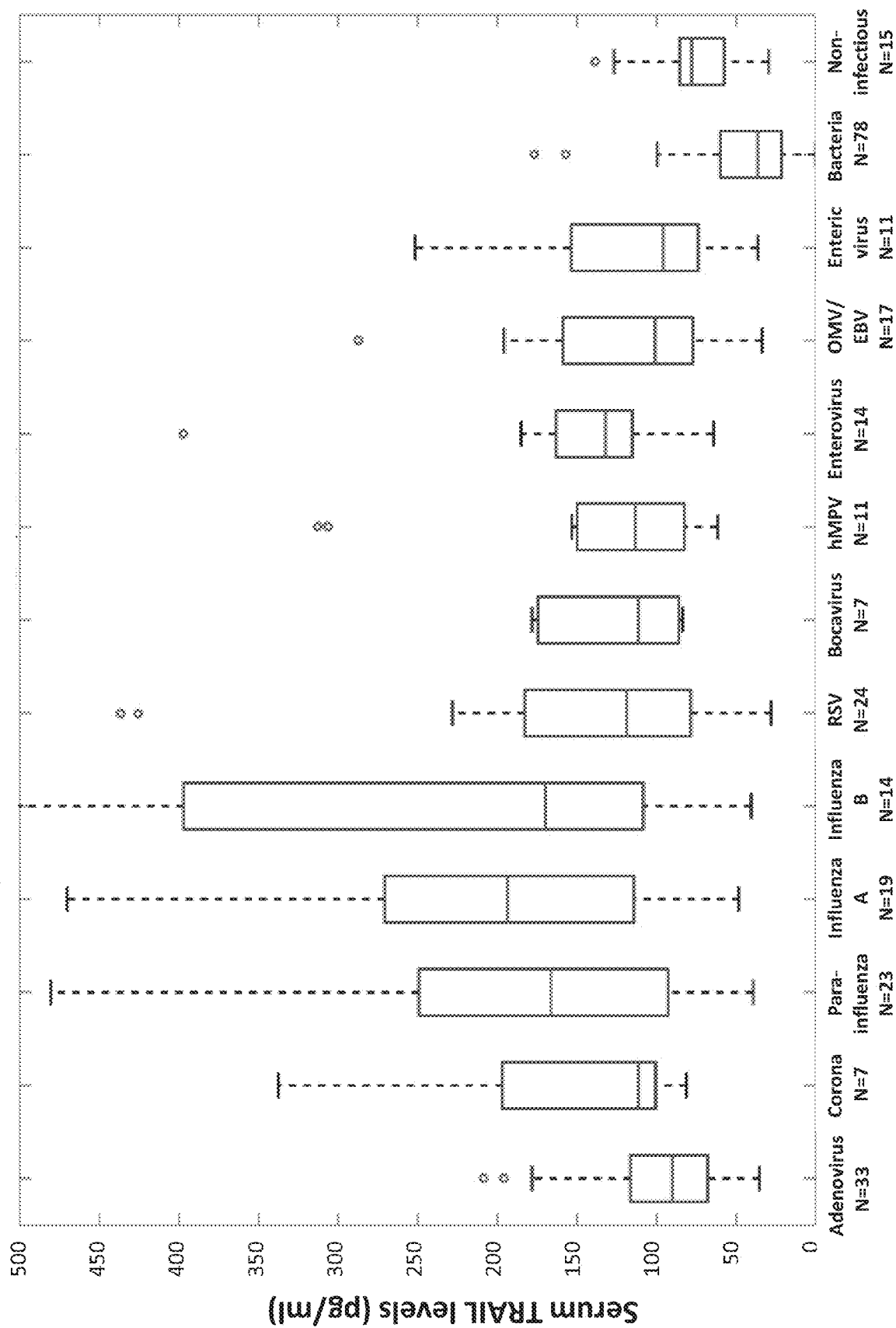

FIG. 9: Serum TRAIL levels of pediatric patients presenting with different infection types.

Blue boxes present first to third quartiles. Red line corresponds to group median. RSV—Respiratory syncytial virus; hMPV—human Metapneumovirus; Enteric viruses include: Rota Virus, Astrovirus, Enteric Adenovirus, Norovirus G I and G II.

Figure 10C:
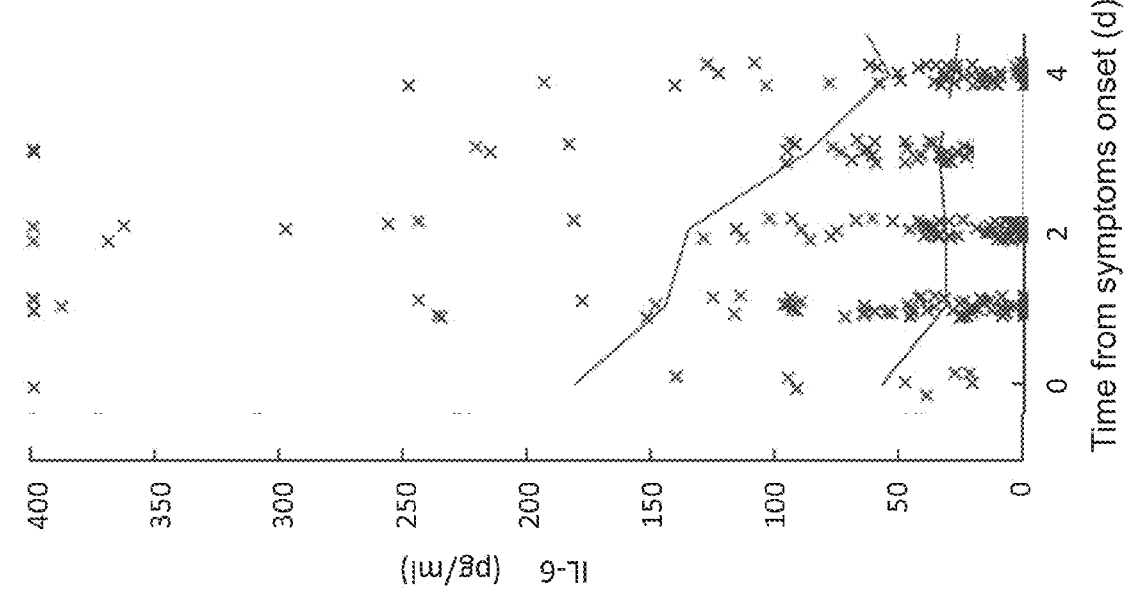

FIGS. 10A-10C: TRAIL is a useful marker for early diagnosis of bacterial and viral infections. Average serum levels of TRAIL, CRP, PCT, IP-10, IL-6 and the TRAIL-CRP-IP-10 signature score at different days from symptoms onset in bacterial and viral patients.

Figure 11:
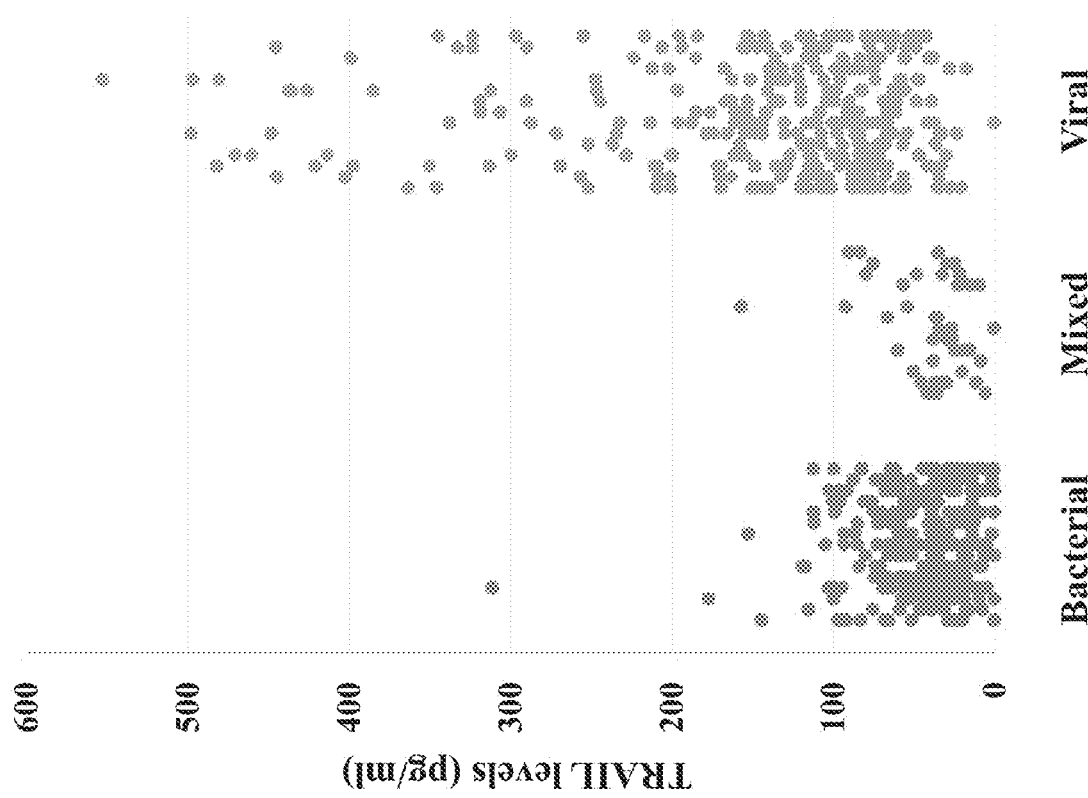

FIG. 11: TRAIL levels are reduced in patients with bacterial-viral co-infection (mixed), similar to patients with pure bacterial infections. Serum TRAIL levels of patients with different infection types as indicated.

DESCRIPTION OF SPECIFIC EMBODIMENTS OF THE INVENTION

The present invention, in some embodiments thereof, relates to the identification of signatures and determinants associated with infections.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Figure 8:
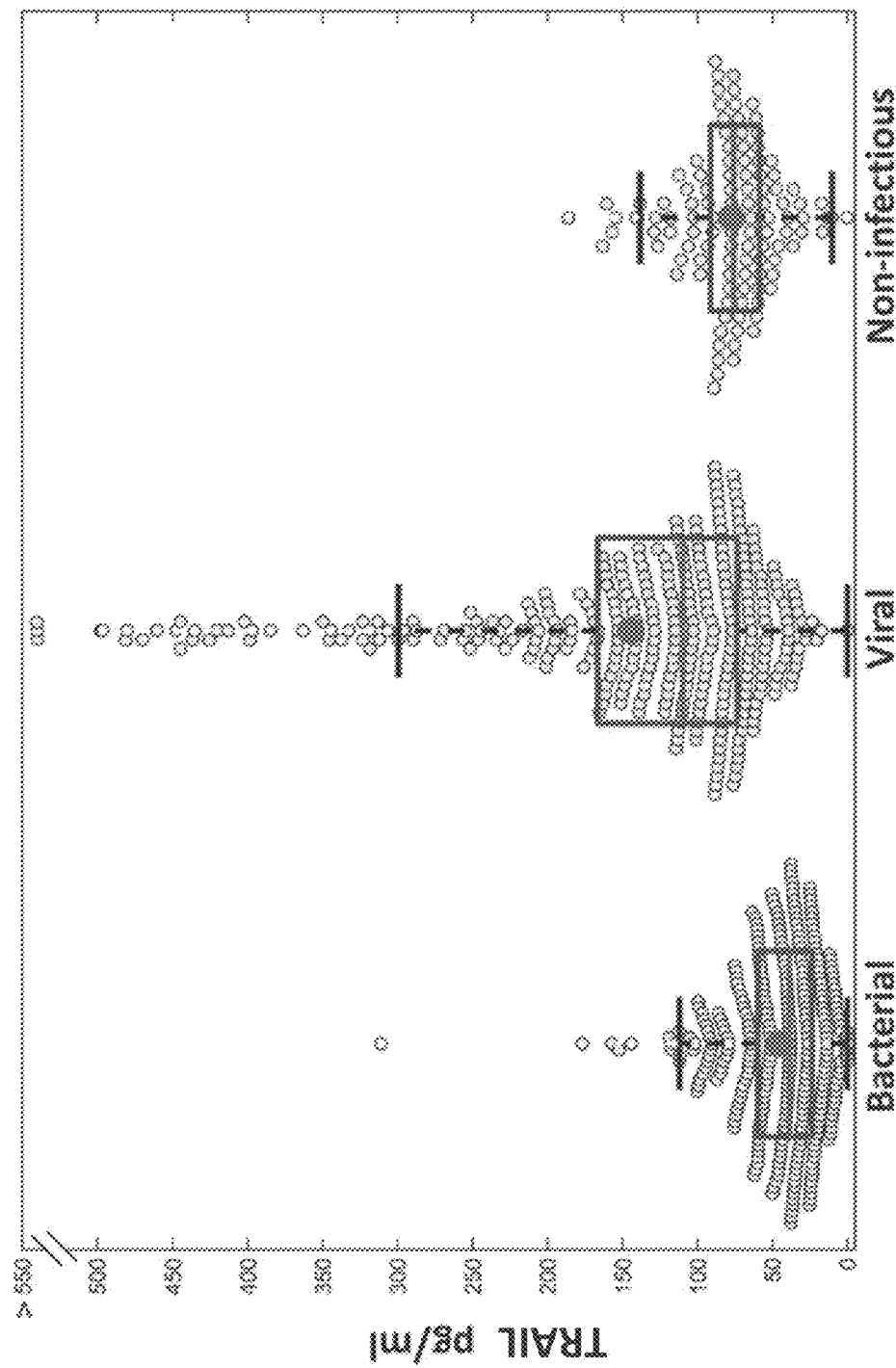

Correct identification of bacterial patients is of high importance as these patients require antibiotic treatment and in some cases more aggressive management (hospitalization, additional diagnostic tests etc). Misclassification of bacterial patients increases the chance of morbidity and mortality. The clinical challenge is to distinguish between these patients from patients with viral infection that have similar symptoms but do not require antibiotic treatment. Circulating host-proteins, such as C-reactive protein (CRP), are routinely used to support diagnosis of infection. The blood levels of these biomarkers are moderately elevated in response to viral infections and to higher extent in response to bacterial infections, with some degree of overlapping. Moreover, some virus type (e.g., adenovirus and influenza), can cause a significant increase in CRP levels, similar to various bacterial infections. The present inventors previously identified TNF-related apoptosis-inducing ligand (TRAIL), as a novel biomarker that can accurately distinguish between bacterial and viral infections. Unlike known biomarkers, TRAIL has unique dynamics in response to infections as its serum levels decrease in response to bacterial infections and increase in response to viral infections (FIG. 8). For example, in a sub-cohort of 233 febrile children (78 bacterial and 155 viral) and 15 non-infectious controls, TRAIL levels were increased in viral patients and decreased in bacterial patients as compared to controls (average±SD [pg/ml]: bacterial 44±32; viral 153±110; controls 78±29; FIG. 9). The difference between TRAIL levels in viral and bacterial patients was statistically significant for all 11 evaluated viral strains (test p-value<0.001; FIG. 9).

Figure 10C:
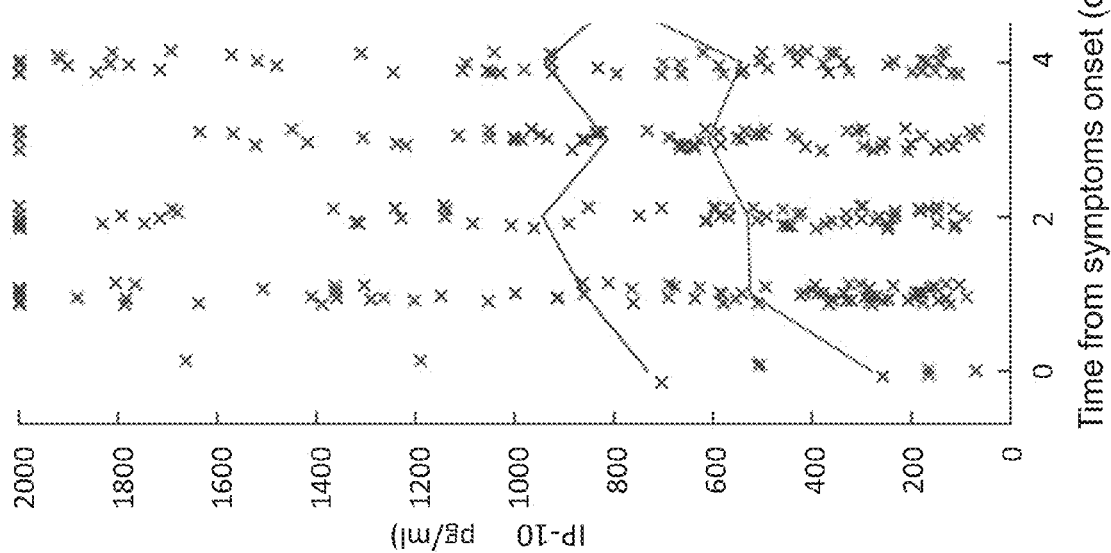

Delayed or no antibiotic treatment in cases of bacterial disease is very common (24%-40% of all bacterial infections), and can lead to disease-related complications resulting in increased rates of morbidity and mortality. Thus, timely identification of patients with bacterial infection is of great importance to guide correct patient management. The present inventors therefore, evaluated the performance of TRAIL in different stages of disease progression. Importantly, it was found that TRAIL levels are already significantly different in patients with bacterial infections at the first days following symptoms onset (FIG. 10). This is compared to currently used biomarkers such as CRP or Procalcitonin (PCT) that reach their maximal differential expression between bacterial and viral patients, only 2-3 days after symptoms onset (FIG. 10). Moreover, the accuracy levels of TRAIL in distinguishing between patients with bacterial and viral infections were higher in the first days following symptoms onset using different TRAIL cutoffs (Tables 5A and B).

Thus, according to a first aspect of the present invention there is provided a method of ruling in a bacterial infection in a subject showing symptoms of an infection, the method comprising measuring the amount of TRAIL in a blood sample being derived from the subject no more than two days following symptom onset, wherein when the amount of the TRAIL is below a first predetermined level, a bacterial infection is ruled in.

The present inventors have also shown that IP10 levels are already significantly different in patients with infections at the first days following symptoms onset (FIG. 10).

According to a particular embodiment, the bacterial infection is a Group A streptococcal bacterial infection.

According to another aspect of the present invention there is provided a method of determining a treatment regimen in a subject showing symptoms of a pathogenic infection comprising measuring the amount of TRAIL in a blood sample being derived from the subject no more than two days following symptom onset, wherein when the amount of the TRAIL is below a first predetermined level, the subject is recommended an anti-bacterial agent.

The methods disclosed herein are used to identify subjects with an infection or a specific infection type. By type of infection it is meant to include bacterial infections, viral infections, mixed infections (bacterial and viral co-infection), no infection (i.e., non-infectious). In a particular embodiment, the methods disclosed are used to rule in a bacterial infection. In further embodiments, the methods disclosed are used to rule in a viral infection or rule out a viral infection. Some methods of the invention are used to distinguish subjects having a bacterial infection, a viral infection, a mixed infection (i.e., bacterial and viral co-infection), patients with a non-infectious disease and healthy individuals. Some methods of the present invention can also be used to monitor or select a treatment regimen for a subject who has an infection In various aspects the method distinguishes a bacterially infected subject from either a subject with non-infectious disease or a healthy subject; a bacterially infected subject from a virally infected subject; a bacterially infected subject from a subject having both a viral and bacterial infection (mixed infection) and a virally infected subject from a subject having both a viral and bacterial infection.

A mixed infected subject refers to a subject having a bacterial and viral co-infection.

In another embodiment, the method is used to discriminate between bacterial and viral etiologies of chronic obstructive pulmonary disease (COPD) exacerbation.

In still another embodiment, the method is used to distinguish between an infective exacerbation state of chronic obstructive pulmonary disease (COPD) and a non-infective exacerbation state of COPD, as further described herein below.

In further embodiments, the method is used in conjunction with an assay to determine the presence of a specific virus/bacteria, as further described herein below.

The infection may be an acute or chronic infection.

A chronic infection is an infection that develops slowly and lasts a long time. Viruses that may cause a chronic infection include Hepatitis C and HIV. One difference between acute and chronic infection is that during acute infection the immune system often produces IgM+ antibodies against the infectious agent, whereas the chronic phase of the infection is usually characteristic of IgM−/IgG+ antibodies. In addition, acute infections cause immune mediated necrotic processes while chronic infections often cause inflammatory mediated fibrotic processes and scaring (e.g. Hepatitis C in the liver). Thus, acute and chronic infections may elicit different underlying immunological mechanisms.

As used herein, the term "infection" refers to a state caused by an infectious agent of viral or bacterial origin. The bacterial infection may be the result of gram-positive, gram-negative bacteria or atypical bacteria.

The term "Gram-positive bacteria" are bacteria that are stained dark blue by Gram staining. Gram-positive organisms are able to retain the crystal violet stain because of the high amount of peptidoglycan in the cell wall.

The term "Gram-negative bacteria" are bacteria that do not retain the crystal violet dye in the Gram staining protocol.

The term "Atypical bacteria" are bacteria that do not fall into one of the classical "Gram" groups. They are usually, though not always, intracellular bacterial pathogens. They include, without limitations, Mycoplasmas spp., *Legionella* spp. Rickettsiae spp., and Chlamydiae spp.

By "ruling in" an infection it is meant that the subject has that type of infection.

By "ruling out" an infection it is meant that the subject does not have that type of infection.

The subjects of this aspect of the present invention may present with a variety of pathogens including, but not limited to Adenovirus, Coronavirus, Parainfluenza virus, Influenza A virus, Influenza B virus, Respiratory syncytial virus A/B, *Chlamydophila pneumoniae, Mycoplasma pneumoniae, Legionella pneumophila*, Rota Virus, *Staphylococcus aureus, Streptococcus pneumoniae*, Astrovirus, Enteric Adenovirus, Norovirus G I and G II, Bocavirus 1/2/3/4, Enterovirus, CMV virus, EBV virus, Group A Strep, or *Escherichia coli*.

Exemplary pathogens contemplated by the present invention include, but are not limited to influenza, respiratory syncytial virus (RSV), rhinovirus and Group A *Streptococcus*.

The subjects (e.g. children) may present with a particular clinical syndrome—for example, low respiratory tract infection (LRTI) infection, upper respiratory tract infection (URTI), fever without identifiable source (FWS), or a serious bacterial infection (SBI) such as UTI (urinary tract infections), septic shock, bacteremia, pneumonia or meningitis.

"Measuring" or "measurement," or alternatively "detecting" or "detection," means assessing the presence, absence, quantity or amount (which can be an effective amount) of the determinant within a clinical or subject-derived sample, including the derivation of qualitative or quantitative concentration levels of such determinants.

A "sample" in the context of the present invention is a biological sample isolated from a subject and can include, by way of example and not limitation, whole blood, serum, plasma, saliva, mucus, breath, urine, CSF, sputum, sweat, stool, hair, seminal fluid, biopsy, rhinorrhea, tissue biopsy, cytological sample, platelets, reticulocytes, leukocytes, epithelial cells, or whole blood cells.

In a particular embodiment, the sample is a blood sample—e.g. serum or a sample comprising blood cells. In a particular embodiment, the sample is depleted of red blood cells.

According to this aspect of the present invention, the sample is derived from the subject no more than 72 hours, no more than 60 hours, no more than 48 hours, no more than 36 hours, no more than one 24 hours or even no more than 12 hours following symptom onset.

The sample may be fresh or frozen.

A "subject" in the context of the present invention may be a mammal (e.g. a human, dog, cat, horse, cow, sheep, pig, goat). According to another embodiment, the subject is a bird (e.g. chicken, turkey, duck or goose). According to a particular embodiment, the subject is a human. The subject may be male or female. The subject may be an adult (e.g. older than 18, 21, or 22 years or a child (e.g. younger than 18, 21 or 22 years). In another embodiment, the subject is an adolescent (between 12 and 21 years), an infant (29 days to less than 2 years of age) or a neonate (birth through the first 28 days of life).

Exemplary symptoms which the subject may present include but are not limited to fever, nausea, headache, sore throat, runny nose, rash and/or muscle soreness.

According to a particular embodiment, the subject does not show signs of having had a heart attack (e.g. has a normal level of creatine kinase, troponin or serum myoglobin, and/or has a normal ECG or EKG).

According to one aspect of the present invention, the level of the polypeptide TRAIL is used to rule in a bacterial infection.

TRAIL:

The protein encoded by this gene is a cytokine that belongs to the tumor necrosis factor (TNF) ligand family. The present invention contemplates measuring either the soluble and/or the membrane form of this protein. In one embodiment, only the soluble form of this protein is measured. Additional names of the gene include without limitations APO2L, TNF-related apoptosis-inducing ligand, TNFSF10 and CD253. This protein binds to several members of the TNF receptor superfamily such as TNFRSF10A/TRAILR1, TNFRSF10B/TRAILR2, TNFRSF10C/TRAILR3, TNFRSF10D/TRAILR4, and possibly also to TNFRSF11B/OPG.

Additional information concerning TRAIL is provided in Table 1, herein below.

TABLE 1

| Protein symbol | Full Gene Name | RefSeq DNA sequence | RefSeq proteins |
| --- | --- | --- | --- |
| TRAIL | Tumor necrosis factor superfamily member 10 | NC_000003.12 NC_018914.2 NT_005612.17 | NP_001177871.1 NP_001177872.1 NP_003801.1 |

Exemplary amino acid sequences of TRAIL are set forth in SEQ ID NOs: 4-8.

In a particular embodiment, TRAIL is the protein that is recognized by the antibody of the kit R&D systems, Human TRAIL/TNFSF10 Quantikine ELISA Kit catalog #DTRL00.

The level of TRAIL increases in viral infections (as compared to non-infectious diseases), and decreases in bacterial infections (as compared to non-infectious diseases).

Thus, when the level of TRAIL is above a predetermined level, it is indicative that the infection is a viral infection and a viral infection may be ruled in (or a bacterial infection may be ruled out).

When the level of TRAIL is below a predetermined level, it is indicative that the infection is a bacterial infection and a bacterial infection may be ruled in (or a viral infection may be ruled out).

For example, a bacterial infection may be ruled out if the polypeptide concentration of TRAIL determined is higher than a pre-determined first threshold value. Optionally, the method further includes determining if a subject has a viral infection (i.e., ruling in a viral infection). A viral infection is ruled in if the polypeptide concentration of TRAIL is higher than a pre-determined second threshold value.

In another specific embodiment the invention includes determining if a subject does not have a viral infection (i.e. ruling out a viral infection). A viral infection is ruled out if the polypeptide concentration of TRAIL determined is lower than a pre-determined first threshold value. Optionally, the method further includes determining if a subject has a bacterial infection (i.e., ruling in a bacterial infection). A bacterial infection is ruled in if the polypeptide concentration of TRAIL is lower than a pre-determined second threshold value.

More specifically, TRAIL levels of 100-1000 pg/ml are usually indicative of a viral infection, while 0-85 pg/ml are usually indicative of a bacterial infection. Bacterial infection can usually be ruled in if TRAIL levels are lower than 85 pg/ml, 70 pg/ml, 60 pg/ml or more preferably 50, 40, 30 or 20 pg/ml, and ruled out if TRAIL levels are higher than 100, 120, 140 or preferably 150 pg/ml.

Additional polypeptides that may be analyzed for the early detection of bacterial infections include but are not limited to CRP and IP10. Thus TRAIL and CRP may be measured, TRAIL and IP10 may be measured or TRAIL, CRP and IP10 may be measured.

Information regarding CRP and IP10 is provided in Table 2, herein below.

TABLE 2

| Protein symbol | Full Gene Name | RefSeq DNA sequence | RefSeq proteins |
| --- | --- | --- | --- |
| CRP | C-reactive protein, pentraxin-related | NC_000001.11 NT_004487.20 NC_018912.2 | NP_000558.2 |
| IP-10 | Chemokine (C-X-C motif) ligand 10 | NC_000004.12 NC_018915.2 NT_016354.20 | NP_001556.2 |

CRP: C-reactive protein; additional aliases of CRP include without limitation RP11-419N10.4 and PTX1.

An exemplary amino acid sequence of human CRP is set forth below in SEQ ID NO: 1.

The level of CRP typically increases in infections (as compared to non-infectious diseases), with the level of CRP being higher in bacterial infections as opposed to viral infections.

Thus, when the level of CRP is above a predetermined level, it is indicative that the infection is a bacterial infection and a bacterial infection may be ruled in (or a viral infection may be ruled out).

When the level of CRP is below a predetermined level, it is indicative that the infection is a viral infection and a viral infection may be ruled in (or a bacterial infection may be ruled out).

CRP levels of 0-40 μg/ml are usually indicative of a viral infection, while 40-400 μg/ml are usually indicative of a bacterial infection. Bacterial infection can usually be ruled in if CRP levels are higher than 50, 60, 70 or more preferably 80 μg/ml, and ruled out if CRP levels are lower than 30 and more preferably 20 μg/ml.

IP10:

This gene encodes a chemokine of the CXC subfamily and ligand for the receptor CXCR3. Additional names of the gene include without limitations: CXCL10, Gamma-IP10, INP10 and chemokine (C-X-C motif) ligand 10.

An exemplary amino acid sequence of human IP10 is set forth in SEQ ID NO: 16. In a particular embodiment, IP10 is the protein that is recognized by the antibody of the kit (R&D systems, Human CXCL10/IP-10 Quantikine ELISA Kit catalog #DIP100).

The level of IP10 increases in infections (as compared to non-infectious diseases), with the level of IP10 being higher in viral infections as opposed to bacterial infections.

Thus, when the level of IP10 is above a predetermined level, it is indicative that the infection is a viral infection and a viral infection may be ruled in (or a bacterial infection may be ruled out).

When the level of IP10 is below a predetermined level, it is indicative that the infection is a bacterial infection and a bacterial infection may be ruled in (or a viral infection may be ruled out).

IP-10 levels of 300-2000 pg/ml are usually indicative of a viral infection, while 160-860 pg/ml are usually indicative of a bacterial infection.

Since IP-10 levels have been shown to be significantly different in patients with infections at the first days following symptoms onset (FIG. 10), the present inventors further contemplate that IP-10 alone can be used as a marker of early infection.

The concentrations of each of the above identified polypeptides may be combined (e.g. by way of a pre-determined mathematical function) to compute a score and the score may be compared to a predetermined reference value as further described herein below.

Further information on generating pre-determined mathematical functions in general and for CRP, IP10 and TRAIL in particular are provided in International Patent Application IL2015/050823, the contents of which are incorporated herein by reference.

Statistical classification algorithms which may be used to calculate the score include, but are not limited to Support Vector Machine (SVM), Logistic Regression (LogReg), Neural Network, Bayesian Network, and a Hidden Markov Model.

A reference value can be relative to a number or value derived from population studies, including without limitation, such subjects having the same infection, subject having the same or similar age range, subjects in the same or similar ethnic group, or relative to the starting sample of a subject undergoing treatment for an infection. Such reference values can be derived from statistical analyses and/or risk prediction data of populations obtained from mathematical algorithms and computed indices of infection. Reference determinant indices can also be constructed and used using algorithms and other methods of statistical and structural classification.

In one embodiment of the present invention, the reference value is the amount (i.e. level) of determinants in a control sample derived from one or more subjects who do not have an infection (i.e., healthy, and or non-infectious individuals). In a further embodiment, such subjects are monitored and/or periodically retested for a diagnostically relevant period of time ("longitudinal studies") following such test to verify continued absence of infection. Such period of time may be one day, two days, two to five days, five days, five to ten days, ten days, or ten or more days from the initial testing date for determination of the reference value. Furthermore, retrospective measurement of determinants in properly banked historical subject samples may be used in establishing these reference values, thus shortening the study time required.

A reference value can also comprise the amounts of determinants derived from subjects who show an improvement as a result of treatments and/or therapies for the infection. A reference value can also comprise the amounts of determinants derived from subjects who have confirmed infection by known techniques.

An example of a bacterially infected reference value index value is the mean or median concentrations of that determinant in a statistically significant number of subjects having been diagnosed as having a bacterial infection.

An example of a virally infected reference value is the mean or median concentrations of that determinant in a statistically significant number of subjects having been diagnosed as having a viral infection.

In another embodiment, the reference value is an index value or a baseline value. An index value or baseline value is a composite sample of an effective amount of determinants from one or more subjects who do not have an infection. A baseline value can also comprise the amounts of determinants in a sample derived from a subject who has shown an improvement in treatments or therapies for the infection. In this embodiment, to make comparisons to the subject-derived sample, the amounts of determinants are similarly calculated and compared to the index value. Optionally, subjects identified as having an infection, are chosen to receive a therapeutic regimen to slow the progression or eliminate the infection.

Additionally, the amount of the determinant can be measured in a test sample and compared to the "normal control level," utilizing techniques such as reference limits, discrimination limits, or risk defining thresholds to define cutoff points and abnormal values. The "normal control level" means the level of one or more determinants or combined determinant indices typically found in a subject not suffering from an infection. Such normal control level and cutoff points may vary based on whether a determinant is used alone or in a formula combining with other determinants into an index. Alternatively, the normal control level can be a database of determinant patterns from previously tested subjects.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections). This will allow patients to be stratified and treated accordingly.

In a specific embodiment of the invention a treatment recommendation (i.e., selecting a treatment regimen) for a subject is provided by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

Examples of antibiotics contemplated by the present invention include, but are not limited to Daptomycin; Gemifloxacin; Telavancin; Ceftaroline; Fidaxomicin; Amoxicillin; Ampicillin; Bacampicillin; Carbenicillin; Cloxacillin; Dicloxacillin; Flucloxacillin; Mezlocillin; Nafcillin; Oxacillin; Penicillin G; Penicillin V; Piperacillin; Pivampicillin; Pivmecillinam; Ticarcillin; Aztreonam; Imipenem; Doripenem; Meropenem; Ertapenem; Clindamycin; Lincomycin; Pristinamycin; Quinupristin; Cefacetrile (cephacetrile); Cefadroxil (cefadroxyl); Cefalexin (cephalexin); Cefaloglycin (cephaloglycin); Cefalonium (cephalonium); Cefaloridine (cephaloridine); Cefalotin (cephalothin); Cefapirin (cephapirin); Cefatrizine; Cefazaflur; Cefazedone; Cefazolin (cephazolin); Cefradine (cephradine); Cefroxadine; Ceftezole; Cefaclor; Cefamandole; Cefmetazole; Cefonicid; Cefotetan; Cefoxitin; Cefprozil (cefproxil); Cefuroxime; Cefuzonam; Cefcapene; Cefdaloxime; Cefdinir; Cefditoren; Cefetamet; Cefixime; Cefmenoxime; Cefodizime; Cefotaxime; Cefpimizole; Cefpodoxime; Cefteram; Ceftibuten; Ceftiofur; Ceftiolene; Ceftizoxime; Ceftriaxone; Cefoperazone; Ceftazidime; Cefclidine; Cefepime; Cefluprenam; Cefoselis; Cefozopran; Cefpirome; Cefquinome; Fifth Generation; Ceftobiprole; Ceftaroline; Not Classified; Cefaclomezine; Cefaloram; Cefaparole; Cefcanel; Cefedrolor; Cefempidone; Cefetrizole; Cefivitril; Cefmatilen; Cefmepidium; Cefovecin; Cefoxazole; Cefrotil; Cefsumide; Cefuracetime; Ceftioxide; Azithromycin; Erythromycin; Clarithromycin; Dirithromycin; Roxithromycin; Telithromycin; Amikacin; Gentamicin; Kanamycin; Neomycin; Netilmicin; Paromomycin; Streptomycin; Tobramycin; Flumequine; Nalidixic acid; Oxolinic acid; Piromidic acid; Pipemidic acid; Rosoxacin; Ciprofloxacin; Enoxacin; Lomefloxacin; Nadifloxacin; Norfloxacin; Ofloxacin; Pefloxacin; Rufloxacin; Balofloxacin; Gatifloxacin; Grepafloxacin; Levofloxacin; Moxifloxacin; Pazufloxacin; Sparfloxacin; Temafloxacin; Tosufloxacin; Besifloxacin; Clinafloxacin; Gemifloxacin; Sitafloxacin; Trovafloxacin; Prulifloxacin; Sulfamethizole; Sulfamethoxazole; Sulfisoxazole; Trimethoprim-Sulfamethoxazole; Demeclocycline; Doxycycline; Minocycline; Oxytetracycline; Tetracycline; Tigecycline; Chloramphenicol; Metronidazole; Tinidazole; Nitrofurantoin; Vancomycin; Teicoplanin; Telavancin; Linezolid; Cycloserine 2; Rifampin; Rifabutin; Rifapentine; Bacitracin; Polymyxin B; Viomycin; Capreomycin.

If a viral infection is ruled in, the subject may be treated with an antiviral agent. Examples of antiviral agents include, but are not limited to Abacavir; Aciclovir; Acyclovir; Adefovir; Amantadine; Amprenavir; Ampligen; Arbidol; Atazanavir; Atripla; Balavir; Boceprevirertet; Cidofovir; Combivir; Dolutegravir; Darunavir; Delavirdine; Didanosine; Docosanol; Edoxudine; Efavirenz; Emtricitabine; Enfuvirtide; Entecavir; Ecoliever; Famciclovir; Fomivirsen; Fosamprenavir; Foscarnet; Fosfonet; Fusion inhibitor; Ganciclovir; Ibacitabine; Imunovir; Idoxuridine; Imiquimod; Indinavir; Inosine; Integrase inhibitor; Interferon type III; Interferon type II; Interferon type I; Interferon; Lamivudine; Lopinavir; Loviride; Maraviroc; Moroxydine; Methisazone; Nelfinavir; Nevirapine; Nexavir; Oseltamivir; Peginterferon alfa-2a; Penciclovir; Peramivir; Pleconaril; Podophyllotoxin; Raltegravir; Reverse transcriptase inhibitor; Ribavirin; Rimantadine; Ritonavir; Pyramidine; Saquinavir; Sofosbuvir; StavudineTelaprevir; Tenofovir; Tenofovir disoproxil; Tipranavir; Trifluridine; Trizivir; Tromantadine; Truvada; traporved; Valaciclovir; Valganciclovir; Vicriviroc; Vidarabine; Viramidine; Zalcitabine; Zanamivir; Zidovudine; RNAi antiviralsmonoclonal antibody respigams; neuraminidase blocking agents.

In another embodiment, the methods of the invention can be used to prompt additional targeted diagnosis such as pathogen specific PCRs, chest-X-ray, cultures etc. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

In a specific embodiment, a diagnostic test recommendation for a subject is provided by identifying the infection type (i.e., bacterial, viral, mixed infection or no infection) in the subject according to any of the disclosed methods and recommending a test to determine the source of the bacterial infection if the subject is identified as having a bacterial infection or a mixed infection; or a test to determine the source of the viral infection if the subject is identified as having a viral infection.

As well as measuring the polypeptide determinants mentioned herein above, the present inventors contemplate measuring at least one, two, three, four, five, six, seven, eight, nine, ten or more additional (non-identical) determinants (polypeptide, RNA or other), wherein the at least one additional determinant is set forth in US Patent Application No. 20080171323, WO2011/132086 and WO2013/117746 and PCT Application IL 2015/051024 and PCT Application IL 2015/051201 and Provisional Application No. 62/302, 849 the contents of each are incorporated herein by reference. Other polypeptide determinants contemplated by the present inventors are the polypeptide counterparts of the RNA determinants described therein.

In one embodiment, at least of the additional determinants is set forth in Table 3 herein below.

TABLE 3

| Protein symbol | Full Gene Name | RefSeq DNA sequence | RefSeq proteins |
| --- | --- | --- | --- |
| IL1R/IL1R1/ IL1RA | Interleukin 1 receptor, type I | NC_000002.12 NT_005403.18 NC_018913.2 | NP_000868.1 NP_001275635.1 |
| SAA/SAA1 | Serum amyloid A1 | NC_000011.10 NC_018922.2 NT_009237.19 | NP_000322.2 NP_001171477.1 NP_954630.1 |
| TREM1 | Triggering receptor expressed on myeloid cells 1 | NC_000006.12 NT_007592.16 NC_018917.2 | NP_001229518.1 NP_001229519.1 NP_061113.1 |
| TREM2 | Triggering receptor expressed on myeloid cells 2 | NC_000006.12 NT_007592.16 NC_018917.2 | NP_001258750.1 NP_061838.1 |
| RSAD2 | Radical S-adenosyl methionine domain containing 2 | NC_000002.12 NT_005334.17 NC_018913.2 | NP_542388.2 |
| NGAL | Lipocalin 2 | NC_000009.12 NC_018920.2 NT_008470.20 | NP_005555.2 |
| MMP8 | Matrix metallopeptidase 8 | NC_000011.10 NT_033899.9 NC_018922.2 | NP_001291370.1 NP_001291371.1 NP_002415.1 |
| MX1 | MX Dynamin-Like GTPase 1 | NC_000021.9 NT_011512.12 NC_018932.2 | NP_001138397.1 NP_001171517.1 NP_001269849.1 NP_002453.2 |
| Neopterin | 2-amino-6-(1,2,3-trihydroxypropyl)-1H-pteridin-4-one IUPAC name | N/A | N/A |
| Procalcitonin (PCT) e.g. SEQ ID NOs: 19-22 | Calcitonin-related polypeptide alpha | NC_000011.10 NC_018922.2 NT_009237.19 | NP_001029124.1 NP_001029125.1 NP_001732.1 |
| IL-6 e.g. SEQ ID NOs: 23-24 | Interleukin 6 | NC_000007.14 NT_007819.18 NC_018918.2 | NP_000591.1 |

More specifically, as well as analyzing TRAIL polypeptide, at least one, at least two, at least three, at least four of the following polypeptides may be analyzed: Interferon gamma-induced protein 10 (IP10), Interleukin 6 (IL-6), and Interleukin 1 receptor, type I (IL1RA). In another embodiment CRP and/or PCT may also be analyzed.

More specifically, as well as analyzing IP10 polypeptide, at least one, at least two, at least three, at least four of the following polypeptides may be analyzed: TRAIL, Interleukin 6 (IL-6), and Interleukin 1 receptor, type I (IL1RA). In another embodiment CRP and/or PCT may also be analyzed.

Contemplated combinations of polypeptides include, but are not limited to:
TRAIL+ IP-10,
TRAIL+ CRP,
TRAIL+ PCT,
TRAIL+ IL1Ra,
TRAIL+ IL-6,
IP-10+ CRP,
IP-10+ PCT,
IP-10+ IL1Ra,
IP-10+ IL-6,
TRAIL+ IP-10+ CRP,
TRAIL+ IP-10+ PCT,
TRAIL+ IP-10+ IL1Ra,
TRAIL+ IP-10+ IL-6,
TRAIL+ CRP+ PCT,
TRAIL+ CRP+ IL1Ra,
TRAIL+ CRP+ IL-6,
TRAIL+ PCT+ IL1Ra,
TRAIL+ PCT+ IL-6,
TRAIL+ IL1Ra+ IL-6,
IP-10+ CRP+ PCT,
IP-10+ CRP+ IL1Ra,
IP-10+ CRP+ IL-6,
IP-10+ PCT+ IL1Ra,
IP-10+ PCT+ IL-6,
IP-10+ IL1Ra+ IL-6,
TRAIL+ IP-10+ CRP+ PCT,
TRAIL+ IP-10+ CRP+ IL1Ra,
TRAIL+ IP-10+ CRP+ IL-6,
TRAIL+ IP-10+ PCT+ IL1Ra,
TRAIL+ IP-10+ PCT+ IL-6,
TRAIL+ IP-10+ IL1Ra+ IL-6,
TRAIL+ CRP+ PCT+ IL1Ra,
TRAIL+ CRP+ PCT+ IL-6,
TRAIL+ CRP+ IL1Ra+ IL-6,
TRAIL+ PCT+ IL1Ra+ IL-6,
IP-10+ CRP+ PCT+ IL1Ra,
IP-10+ CRP+ PCT+ IL-6,
IP-10+ CRP+ IL1Ra+ IL-6,
IP-10+ PCT+ IL1Ra+ IL-6,
TRAIL+ IP-10+ CRP+ PCT+ IL1Ra,
TRAIL+ IP-10+ CRP+ PCT, IL-6,
TRAIL+ IP-10+ CRP+ IL1Ra+ IL-6,
TRAIL+ IP-10+ PCT+ IL1Ra+ IL-6,
TRAIL+ CRP+ PCT+ IL1Ra+ IL-6,
IP-10+ CRP+ PCT+ IL1Ra+ IL-6,
TRAIL+ IP-10+ CRP+ PCT+ IL1Ra+ IL-6, According to this aspect of the present invention, in order to distinguish between the different infection types (or to rule in a bacterial infection), no more than 30 determinants are measured, no more than 25 determinants are measured, no more than 20 determinants are measured, no more than 15 determinants are measured, no more than 10 determinants are measured, no more than 5 determinants are measured, no more than 4 determinants are measured, no more than 3 determinants are measured, no more than 2 determinants are measured or only TRAIL is measured.

Other determinants that may be measured according to aspects of the present invention include pathogen (bacterial or viral) specific RNA or polypeptide determinants. This may be carried out in order to aid in identification of a specific pathogen. The measurements may be effected simultaneously with the above-described measurements or consecutively.

According to another aspect of the present invention there is provided a method of distinguishing between an infectious exacerbation state and a non-infectious exacerbation state of chronic obstructive pulmonary disease (COPD) or asthma of a subject comprising measuring the amount of TNF-related apoptosis-inducing ligand (TRAIL) in a blood sample derived from the subject, wherein the amount is indicative of the infectivity of the exacerbation state of COPD or asthma.

Chronic obstructive pulmonary disease (COPD) is an obstructive, inflammatory lung disease characterized by long-term poor airflow. The main symptoms include shortness of breath and cough with sputum production. COPD is a progressive disease, worsening over time.

An exacerbation of COPD is defined as an event in the natural course of the disease characterized by a change in the patient's baseline dyspnea, cough, and/or sputum that is beyond normal day-to-day variations; it is typically acute in onset; and may warrant a change in regular medication. The exacerbation may present with signs of increased work of breathing such as fast breathing, a fast heart rate, sweating, active use of muscles in the neck, a bluish tinge to the skin, and confusion or combative behavior in very severe exacerbations. Crackles may also be heard over the lungs on examination with a stethoscope.

The method of this aspect of the present invention seeks to direct preventative therapies, differentiate stable disease from exacerbation, exacerbation of COPD or asthma from other causes of symptom deterioration and discriminate between bacterial and viral etiologies of exacerbation in order to guide correct treatment. At present exacerbation is a clinical diagnosis of exclusion, leading to both under- and over-treatment of patients and therefore excess morbidity and healthcare cost.

In some embodiments of the present invention, TRAIL serum levels is associated with bacterial, viral or mixed infection in COPD patients. Thus, it can distinguish between infection-related exacerbations from other causes of symptom deterioration in COPD patients. In yet another embodiment, it can distinguish between bacterial and viral etiologies of exacerbation in COPD patients, which in turn allows for the selection of an appropriate treatment regimen (e.g. antibiotic treatment in the case of bacterial infection; or inhaled bronchodilators or corticosteroids in the case of a non-bacterial infection). In yet another embodiment, it can distinguish between mixed bacterial-viral co-infection and a pure viral infection in COPD patients.

In some embodiments of the present invention, TRAIL serum levels is associated with bacterial, viral or mixed infection in asthmatic patients. Thus, it can distinguish between infection-related exacerbations from other causes of symptom deterioration in asthmatic patients. In yet another embodiment, it can distinguish between bacterial and viral etiologies of exacerbation in asthmatic patients, which in turn allows for the selection of an appropriate treatment regimen. In yet another embodiment, it can distinguish between mixed bacterial-viral co-infection and a pure viral infection in asthmatic patients.

As mentioned, the assay of the present invention may also be carried out in conjunction with additional microbial tests such as nucleic acid amplification-based tests (NAAT) which analyze for the presence of a specific pathogen.

Testing for the presence of particular pathogens may suffer from reduced clinical utility because such tests cannot not distinguish between pathogenic strains of microorganisms and potential colonizers, which can be present as part of the natural microbiota without causing an infection. A biomarker that is able to distinguish between carriage and pathogenicity of a detected microorganism could serve as a complementary diagnostic with high clinical value. The combination of the two types of diagnostics offers the physician valuable information that can guide correct patient treatment. For example qPCR detection of specific bacteria together with biomarker-based conformation of pathogenicity empower the physician prescribing the correct antibiotic type. On the other hand, identification of specific bacteria but with biomarker-based conformation of carriage could prevent the doctor from prescribing unnecessary antibiotic treatment. Biomarkers that are based on the patient immune response to infection are not sensitive to bacterial or viral carriage (of microorganisms that are part of the body natural microbiota) as these do to evoke an immune response. Therefore, they are ideal candidates to serve as complementary diagnostic to methods that target the pathogen (NAAT based, culture etc.). Another significant limitation of diagnostic test that target the pathogen is the difficulty in identifying mixed bacterial and viral co-infections. For example, identifying a respiratory viral strain by NAAT-based methods (e.g., PCR), can lead the doctor to avoid antibiotic treatment. However, in many cases, there is a secondary bacterial infection on top of the viral infection that can result in morbidity and mortality if left untreated. Host-based biomarkers that can indicate a potential secondary bacterial infection in case of identified primary viral infection can complement the targeted diagnostics and guide the doctor to prescribe appropriate antibiotic treatment. As illustrated in the Examples section, the present inventors demonstrated that TRAIL levels go down in patients with mixed infections similar to patients with pure bacterial infections (FIG. 11). Thus, TRAIL can be used as an effective biomarker for guiding antibiotic treatment in cases of bacterial-viral co-infection as a complement to targeted diagnostics.

Thus, according to still another aspect of the present invention there is provided a method of classifying an infection type of a subject comprising:

(a) analyzing for the presence of specific pathogen in a sample of the subject; and (b) measuring the amount of TRAIL in a sample of the subject, wherein the presence of the specific pathogen and the amount of TRAIL is indicative of the infection type.

Methods for analyzing for a specific pathogen may comprise the use polynucleotide base assays (e.g. PCR based assays) that are capable of detecting a gene product that is specific to that pathogen type. Other methods include culture assays as known in the art.

According to this aspect of the present invention the TRAIL may be measured at the RNA level or the protein level, as further described herein.

In particular embodiments, determining the amount of TRAIL is effected following a positive result for the presence of the specific pathogen. In this set up, the level of TRAIL may be used to distinguish between carriage and pathogenicity of an identified microorganism (bacteria or virus).

In other embodiments, TRAIL is used to distinguish between mixed bacterial-viral co-infection and a pure viral infection following identification of a viral strain in a patient sample.

In some embodiments, measuring the RNA or protein levels of TRAIL can be performed simultaneously on the same apparatus as the targeted diagnosis.

In other embodiments, measuring TRAIL levels can be used to prompt additional targeted diagnosis such as pathogen specific PCRs. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

For all the aspects described herein, methods of measuring the levels of polypeptides are well known in the art and include, e.g., immunoassays based on antibodies to proteins, aptamers or molecular imprints.

The polypeptide determinants can be detected in any suitable manner, but are typically detected by contacting a sample from the subject with an antibody, which binds the determinant and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological sample as described above, and may be the same sample of biological sample used to conduct the method described above.

In one embodiment, the antibody which specifically binds the determinant is attached (either directly or indirectly) to a signal producing label, including but not limited to a radioactive label, an enzymatic label, a hapten, a reporter dye or a fluorescent label.

Immunoassays carried out in accordance with some embodiments of the present invention may be homogeneous assays or heterogeneous assays. In a homogeneous assay the immunological reaction usually involves the specific antibody (e.g., anti-determinant antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels, which may be employed, include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays are oligonucleotides, immunoblotting, immunofluorescence methods, immunoprecipitation, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al., titled "Methods for Modulating Ligand-Receptor Interactions and their Application," U.S. Pat. No. 4,659,678 to Forrest et al., titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogenous Specific Binding Assay Employing a Coenzyme as Label." The determinant can also be detected with antibodies using flow cytometry. Those skilled in the art will be familiar with flow cytometric techniques which may be useful in carrying out the methods disclosed herein (Shapiro 2005). These include, without limitation, Cytokine Bead Array (Becton Dickinson) and Luminex technology.

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., $^{35}$S, $^{125}$I, $^{131}$I) enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of determinant proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth U. and Muller D. 2002).

For determinant-proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant $K_M$ using known algorithms, such as the Hill plot, Michaelis-Menten equation, linear regression plots such as Lineweaver-Burk analysis, and Scatchard plot.

In particular embodiments, the antibodies of the present invention are monoclonal antibodies.

Suitable sources for antibodies for the detection of determinants include commercially available sources such as, for example, Abazyme, Abnova, AssayPro, Affinity Biologicals, AntibodyShop, Aviva bioscience, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, against any of the polypeptide determinants described herein.

The presence of a label can be detected by inspection, or a detector which monitors a particular probe or probe combination is used to detect the detection reagent label. Typical detectors include spectrophotometers, phototubes and photodiodes, microscopes, scintillation counters, cameras, film and the like, as well as combinations thereof. Those skilled in the art will be familiar with numerous suitable detectors that widely available from a variety of commercial sources and may be useful for carrying out the method disclosed herein. Commonly, an optical image of a substrate comprising bound labeling moieties is digitized for subsequent computer analysis. See generally The Immunoassay Handbook [The Immunoassay Handbook. Third Edition. 2005].

Traditional laboratory risk factors and additional clinical parameters may also be measured together with the above-described polypeptides to further increase the accuracy of the signatures.

"Traditional laboratory risk factors" encompass biomarkers isolated or derived from subject samples and which are currently evaluated in the clinical laboratory and used in traditional global risk assessment algorithms, such as absolute neutrophil count (abbreviated ANC), absolute lymphocyte count (abbreviated ALC), white blood count (abbreviated WBC), neutrophil % (defined as the fraction of white blood cells that are neutrophils and abbreviated Neu (%)), lymphocyte % (defined as the fraction of white blood cells that are lymphocytes and abbreviated Lym (%)), monocyte % (defined as the fraction of white blood cells that are monocytes and abbreviated Mon (%)), Sodium (abbreviated Na), Potassium (abbreviated K), Bilirubin (abbreviated Bili).

"Clinical parameters" encompass all non-sample or non-analyte biomarkers of subject health status or other characteristics, such as, without limitation, age (Age), ethnicity (RACE), gender (Sex), core body temperature (abbreviated "temperature"), maximal core body temperature since initial appearance of symptoms (abbreviated "maximal temperature"), time from initial appearance of symptoms (abbreviated "time from symptoms") or family history (abbreviated FamHX).

The patient medical background conditions such as chronic lung diseases and diabetes may affect its immune response to infection that is reflected by changes in diagnostic accuracy of immune-based diagnostics (see Example 1, herein below). Thus, information regarding the patient background clinical conditions could potentially be integrated with protein biomarker classifiers predicted outcome in order to improve patient diagnosis.

Kits

Some aspects of the invention also include a determinant-detection reagent such as antibodies packaged together in the form of a kit. The kit may contain in separate containers antibodies (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. The detectable label may be attached to a secondary antibody which binds to the Fc portion of the antibody which recognizes the determinant. Instructions (e.g., written, tape, VCR, CD-ROM, etc.) for carrying out the assay may be included in the kit.

The kits of this aspect of the present invention may comprise additional components that aid in the detection of the determinants such as enzymes, salts, buffers etc. necessary to carry out the detection reactions.

For example, determinant detection reagents (e.g. antibodies) can be immobilized on a solid matrix such as a porous strip or an array to form at least one determinant detection site. The measurement or detection region of the porous strip may include a plurality of sites. A test strip may also contain sites for negative and/or positive controls. Alternatively, control sites can be located on a separate strip from the test strip. Optionally, the different detection sites may contain different amounts of immobilized detection reagents, e.g., a higher amount in the first detection site and lesser amounts in subsequent sites. Upon the addition of test sample, the number of sites displaying a detectable signal provides a quantitative indication of the amount of determinants present in the sample. The detection sites may be configured in any suitably detectable shape and are typically in the shape of a bar or dot spanning the width of a test strip.

Examples of "Monoclonal antibodies for measuring TRAIL", include without limitation: Mouse, Monoclonal (55B709-3) IgG; Mouse, Monoclonal (2E5) IgG1; Mouse, Monoclonal (2E05) IgG1; Mouse, Monoclonal (M912292) IgG1 kappa; Mouse, Monoclonal (IIIF6) IgG2b; Mouse, Monoclonal (2E1-1B9) IgG1; Mouse, Monoclonal (RIK-2) IgG1, kappa; Mouse, Monoclonal M181 IgG1; Mouse, Monoclonal VI10E IgG2b; Mouse, Monoclonal MAB375 IgG1; Mouse, Monoclonal MAB687 IgG1; Mouse, Monoclonal HS501 IgG1; Mouse, Monoclonal clone 75411.11 Mouse IgG1; Mouse, Monoclonal T8175-50 IgG; Mouse, Monoclonal 2B2.108 IgG1; Mouse, Monoclonal B-T24 IgG1; Mouse, Monoclonal 55B709.3 IgG1; Mouse, Monoclonal D3 IgG1; Goat, Monoclonal C19 IgG; Rabbit, Monoclonal H257 IgG; Mouse, Monoclonal 500-M49 IgG; Mouse, Monoclonal 05-607 IgG; Mouse, Monoclonal B-T24 IgG1; Rat, Monoclonal (N2B2), IgG2a, kappa; Mouse, Monoclonal (1A7-2B7), IgG1; Mouse, Monoclonal (55B709.3), IgG and Mouse, Monoclonal B-S23*IgG1.

Soluble TRAIL and membrane TRAIL can be distinguished by using different measuring techniques and samples. For example, Soluble TRAL can be measured without limitation in cell free samples such as serum or plasma, using without limitation lateral flow immunoassay (LFIA), as further described herein below. Membrane TRAIL can be measured in samples that contain cells using cell based assays including without limitation flow cytometry, ELISA, and other immunoassays.

Lateral Flow Immunoassays (LFIA):

This is a technology which allows rapid measurement of analytes at the point of care (POC) and its underlying principles are described below. According to one embodiment, LFIA is used in the context of a hand-held device.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex.

After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones the fluid enters the final porous material, the wick, that simply acts as a waste container. Lateral Flow Tests can operate as either competitive or sandwich assays.

Different formats may be adopted in LFIA. Strips used for LFIA contain four main components. A brief description of each is given before describing format types.

Sample Application Pad:

It is made of cellulose and/or glass fiber and sample is applied on this pad to start assay. Its function is to transport the sample to other components of lateral flow test strip (LFTS). Sample pad should be capable of transportation of the sample in a smooth, continuous and homogenous manner. Sample application pads are sometimes designed to pretreat the sample before its transportation. This pretreatment may include separation of sample components, removal of interferences, adjustment of pH, etc.

Conjugate Pad:

It is the place where labeled biorecognition molecules are dispensed. Material of conjugate pad should immediately release labeled conjugate upon contact with moving liquid sample. Labeled conjugate should stay stable over entire life span of lateral flow strip. Any variations in dispensing, drying or release of conjugate can change results of assay significantly. Poor preparation of labeled conjugate can adversely affect sensitivity of assay. Glass fiber, cellulose, polyesters and some other materials are used to make conjugate pad for LFIA. Nature of conjugate pad material has an effect on release of labeled conjugate and sensitivity of assay.

Nitrocellulose Membrane:

It is highly critical in determining sensitivity of LFIA. Nitrocellulose membranes are available in different grades. Test and control lines are drawn over this piece of membrane. So an ideal membrane should provide support and good binding to capture probes (antibodies, aptamers etc.). Nonspecific adsorption over test and control lines may affect results of assay significantly, thus a good membrane will be characterized by lesser non-specific adsorption in the regions of test and control lines. Wicking rate of nitrocellulose membrane can influence assay sensitivity. These membranes are easy to use, inexpensive, and offer high affinity for proteins and other biomolecules. Proper dispensing of bioreagents, drying and blocking play a role in improving sensitivity of assay.

Adsorbent Pad:

It works as sink at the end of the strip. It also helps in maintaining flow rate of the liquid over the membrane and stops back flow of the sample. Adsorbent capacity to hold liquid can play an important role in results of assay.

All these components are fixed or mounted over a backing card. Materials for backing card are highly flexible because they have nothing to do with LFIA except providing a platform for proper assembling of all the components. Thus backing card serves as a support and it makes easy to handle the strip.

Major steps in LFIA are (i) preparation of antibody against target analyte (ii) preparation of label (iii) labeling of biorecognition molecules (iv) assembling of all components onto a backing card after dispensing of reagents at their proper pads (v) application of sample and obtaining results.

Sandwich Format:

In a typical format, label (Enzymes or nanoparticles or fluorescence dyes) coated antibody or aptamer is immobilized at conjugate pad. This is a temporary adsorption which can be flushed away by flow of any buffer solution. A primary antibody or aptamer against target analyte is immobilized over test line. A secondary antibody or probe against labeled conjugate antibody/aptamer is immobilized at control zone.

Sample containing the analyte is applied to the sample application pad and it subsequently migrates to the other parts of strip. At conjugate pad, target analyte is captured by the immobilized labeled antibody or aptamer conjugate and results in the formation of labeled antibody conjugate/analyte complex. This complex now reaches at nitrocellulose membrane and moves under capillary action. At test line, label antibody conjugate/analyte complex is captured by another antibody which is primary to the analyte. Analyte becomes sandwiched between labeled and primary antibodies forming labeled antibody conjugate/analyte/primary antibody complex. Excess labeled antibody conjugate will be captured at control zone by secondary antibody. Buffer or excess solution goes to absorption pad. Intensity of color at test line corresponds to the amount of target analyte and is measured with an optical strip reader or visually inspected. Appearance of color at control line ensures that a strip is functioning properly.

Competitive Format:

Such a format suits best for low molecular weight compounds which cannot bind two antibodies simultaneously. Absence of color at test line is an indication for the presence of analyte while appearance of color both at test and control lines indicates a negative result. Competitive format has two layouts. In the first layout, solution containing target analyte is applied onto the sample application pad and prefixed labeled biomolecule (antibody/aptamer) conjugate gets hydrated and starts flowing with moving liquid. Test line contains pre-immobilized antigen (same analyte to be detected) which binds specifically to label conjugate. Control line contains pre-immobilized secondary antibody which has the ability to bind with labeled antibody conjugate. When liquid sample reaches at the test line, pre-immobilized antigen will bind to the labeled conjugate in case target analyte in sample solution is absent or present in such a low quantity that some sites of labeled antibody conjugate were vacant. Antigen in the sample solution and the one which is immobilized at test line of strip compete to bind with labeled conjugate. In another layout, labeled analyte conjugate is dispensed at conjugate pad while a primary antibody to analyte is dispensed at test line. After application of analyte solution a competition takes place between analyte and labeled analyte to bind with primary antibody at test line.

Multiplex Detection Format:

Multiplex detection format is used for detection of more than one target species and assay is performed over the strip containing test lines equal to number of target species to be analyzed. It is highly desirable to analyze multiple analytes simultaneously under same set of conditions. Multiplex detection format is very useful in clinical diagnosis where multiple analytes which are inter-dependent in deciding about the stage of a disease are to be detected. Lateral flow strips for this purpose can be built in various ways i.e. by increasing length and test lines on conventional strip, making other structures like stars or T-shapes. Shape of strip for LFIA will be dictated by number of target analytes. Miniaturized versions of LFIA based on microarrays for multiplex detection of DNA sequences have been reported to have several advantages such as less consumption of test reagents, requirement of lesser sample volume and better sensitivity.

Labels:

Any material that is used as a label should be detectable at very low concentrations and it should retain its properties upon conjugation with biorecognition molecules. This conjugation is also expected not to change features of biorecognition probes. Ease in conjugation with biomolecules and stability over longer period of time are desirable features for a good label. Concentrations of labels down to $10^{-9}$ M are optically detectable. After the completion of assay, some labels generate direct signal (as color from gold colloidal) while others require additional steps to produce analytical signal (as enzymes produce detectable product upon reaction with suitable substrate). Hence the labels which give direct signal are preferable in LFA because of less time consumption and reduced procedure.

Gold Nanoparticles:

Colloidal gold nanoparticles are the most commonly used labels in LFA. Colloidal gold is inert and gives very perfect spherical particles. These particles have very high affinity toward biomolecules and can be easily functionalized. Optical properties of gold nanoparticles are dependent on size and shape. Size of particles can be tuned by use of suitable chemical additives. Their unique features include environment friendly preparation, high affinity toward proteins and biomolecules, enhanced stability, exceptionally higher values for charge transfer and good optical signaling. Optical signal of gold nanoparticles in colorimetric LFA can be amplified by deposition of silver, gold nanoparticles and enzymes.

Magnetic Particles and Aggregates:

Colored magnetic particles produce color at the test line which is measured by an optical strip reader but magnetic signals coming from magnetic particles can also be used as detection signals and recorded by a magnetic assay reader. Magnetic signals are stable for longer time compared to optical signals and they enhance sensitivity of LFA by 10 to 1000 folds.

Fluorescent and Luminescent Materials:

Fluorescent molecules are widely used in LFA as labels and the amount of fluorescence is used to quantitate the concentration of analyte in the sample. Detection of proteins is accomplished by using organic fluorophores such as rhodamine as labels in LFA.

Current developments in nanomaterial have headed to manufacture of quantum dots which display very unique electrical and optical properties. These semiconducting particles are not only water soluble but can also be easily combined with biomolecules because of closeness in dimensions. Owing to their unique optical properties, quantum dots have come up as a substitute to organic fluorescent dyes. Like gold nanoparticles QDs show size dependent optical properties and a broad spectrum of wavelengths can be monitored. Single light source is sufficient to excite quantum dots of all different sizes. QDs have high photo stability and absorption coefficients.

Upconverting phosphors (UCP) are characterized by their excitation in infra-red region and emission in high energy visible region. Compared to other fluorescent materials, they have a unique advantage of not showing any auto fluorescence. Because of their excitation in IR regions, they do not photo degrade biomolecules. A major advantage lies in their production from easily available bulk materials. Although difference in batch to batch preparation of UCP reporters can affect sensitivity of analysis in LFA, it was observed that they can enhance sensitivity of analytical signal by 10 to 100 folds compared to gold nanoparticles or colored latex beads, when analysis is carried out under same set of biological conditions.

Enzymes:

Enzymes are also employed as labels in LFA. But they increase one step in LFA which is application of suitable substrate after complete assay. This substrate will produce color at test and control lines as a result of enzymatic reaction. In case of enzymes, selection of suitable enzyme substrate combination is one necessary requirement in order to get a colored product for strip reader or electroactive product for electrochemical detection. In other words, sensitivity of detection is dependent on enzyme substrate combination.

Colloidal Carbon:

Colloidal carbon is comparatively inexpensive label and its production can be easily scaled up. Because of their black color, carbon NPs can be easily detected with high sensitivity. Colloidal carbon can be functionalized with a large variety of biomolecules for detection of low and high molecular weight analytes.

Detection Systems:

In case of gold nanoparticles or other color producing labels, qualitative or semi-quantitative analysis can be done by visual inspection of colors at test and control lines. The major advantage of visual inspection is rapid qualitative answer in "Yes" or "NO". Such quick replies about presence of an analyte in clinical analysis have very high importance. Such tests help doctors to make an immediate decision near the patients in hospitals in situations where test results from central labs cannot be waited for because of huge time consumption. But for quantification, optical strip readers are employed for measurement of the intensity of colors produced at test and control lines of strip. This is achieved by inserting the strips into a strip reader and intensities are recorded simultaneously by imaging softwares. Optical images of the strips can also be recorded with a camera and then processed by using a suitable software. Procedure includes proper placement of strip under the camera and a controlled amount of light is thrown on the areas to be observed. Such systems use monochromatic light and wavelength of light can be adjusted to get a good contrast among test and control lines and background. In order to provide good quantitative and reproducible results, detection system should be sensitive to different intensities of colors. Optical standards can be used to calibrate an optical reader device. Automated systems have advantages over manual imaging and processing in terms of time consumption, interpretation of results and adjustment of variables.

In case of fluorescent labels, a fluorescence strip reader is used to record fluorescence intensity of test and control lines. Fluorescence brightness of test line increased with an increase in nitrated ceruloplasmin concentration in human serum when it was detected with a fluorescence strip reader. A photoelectric sensor was also used for detection in LFIA where colloidal gold is exposed to light emitting diode and resulting photoelectrons are recorded. Chemiluminescence which results from reaction of enzyme and substrate is measured as a response to amount of target analyte. Magnetic strip readers and electrochemical detectors are also reported as detection systems in LFTS but they are not very common. Selection of detector is mainly determined by the label employed in analysis.

Examples of "Monoclonal antibodies for measuring CRP", include without limitation: Mouse, Monoclonal (108-2A2); Mouse, Monoclonal (108-7G41D2); Mouse, Monoclonal (12D-2C-36), IgG1; Mouse, Monoclonal (1G1), IgG1; Mouse, Monoclonal (5A9), IgG2a kappa; Mouse, Monoclonal (63F4), IgG1; Mouse, Monoclonal (67A1), IgG1; Mouse, Monoclonal (8B-5E), IgG1; Mouse, Monoclonal (B893M), IgG2b, lambda; Mouse, Monoclonal (C1), IgG2b; Mouse, Monoclonal (C11F2), IgG; Mouse, Monoclonal (C2), IgG1; Mouse, Monoclonal (C3), IgG1; Mouse, Monoclonal (C4), IgG1; Mouse, Monoclonal (C5), IgG2a; Mouse, Monoclonal (C6), IgG2a; Mouse, Monoclonal (C7), IgG1; Mouse, Monoclonal (CRP103), IgG2b; Mouse, Monoclonal (CRP11), IgG1; Mouse, Monoclonal (CRP135), IgG1; Mouse, Monoclonal (CRP169), IgG2a; Mouse, Monoclonal (CRP30), IgG1; Mouse, Monoclonal (CRP36), IgG2a; Rabbit, Monoclonal (EPR283Y), IgG; Mouse, Monoclonal (KT39), IgG2b; Mouse, Monoclonal (N-a), IgG1; Mouse, Monoclonal (N1G1), IgG1; Monoclonal (P5A9AT); Mouse, Monoclonal (S5G1), IgG1; Mouse, Monoclonal (SB78c), IgG1; Mouse, Monoclonal (SB78d), IgG1 and Rabbit, Monoclonal (Y284), IgG.

Polyclonal antibodies for measuring determinants include without limitation antibodies that were produced from sera by active immunization of one or more of the following: Rabbit, Goat, Sheep, Chicken, Duck, Guinea Pig, Mouse, Donkey, Camel, Rat and Horse.

Examples of detection agents, include without limitation: scFv, dsFv, Fab, sVH, F(ab')$_2$, Cyclic peptides, Haptamers, A single-domain antibody, Fab fragments, Single-chain variable fragments, Affibody molecules, Affilins, Nanofitins, Anticalins, Avimers, DARPins, Kunitz domains, Fynomers and Monobody.

In particular embodiments, the kit does not comprise a number of antibodies that specifically recognize more than 50, 20 15, 10, 9, 8, 7, 6, 5 or 4 polypeptides.

In other embodiments, the array of the present invention does not comprise a number of antibodies that specifically recognize more than 50, 20 15, 10, 9, 8, 7, 6, 5 or 4 polypeptides.

Some aspects of the present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life or disability) may screen applicants in the process of determining coverage or pricing, or existing clients for possible intervention. Data collected in such population screens, particularly when tied to any clinical progression to conditions like infection, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein.

A machine-readable storage medium can comprise a data storage material encoded with machine-readable data or data arrays which, when using a machine programmed with instructions for using the data, is capable of use for a variety of purposes. Measurements of effective amounts of the biomarkers of the invention and/or the resulting evaluation of risk from those biomarkers can be implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system used in some aspects of the invention may also be considered to be implemented as a computer-readable storage medium, configured with a computer program, where the storage medium so configured causes a computer to operate in a specific and predefined manner to perform various functions described herein.

The polypeptide determinants of the present invention, in some embodiments thereof, can be used to generate a "reference determinant profile" of those subjects who do not have an infection. The determinants disclosed herein can also be used to generate a "subject determinant profile" taken from subjects who have an infection. The subject determinant profiles can be compared to a reference determinant profile to diagnose or identify subjects with an infection. The subject determinant profile of different infection types can be compared to diagnose or identify the type of infection. The reference and subject determinant profiles of the present invention, in some embodiments thereof, can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other disease-risk algorithms and computed indices such as those described herein.

The effectiveness of a treatment regimen can be monitored by detecting a determinant in an effective amount (which may be one or more) of samples obtained from a subject over time and comparing the amount of determinants detected. For example, a first sample can be obtained prior to the subject receiving treatment and one or more subsequent samples are taken after or during treatment of the subject.

For example, the methods of the invention can be used to discriminate between bacterial, viral and mixed infections (i.e. bacterial and viral co-infections.) This will allow patients to be stratified and treated accordingly.

In a specific embodiment of the invention a treatment recommendation (i.e., selecting a treatment regimen) for a subject is provided by identifying the type infection (i.e., bacterial, viral, mixed infection or no infection) in the subject according to the method of any of the disclosed methods and recommending that the subject receive an antibiotic treatment if the subject is identified as having bacterial infection or a mixed infection; or an anti-viral treatment is if the subject is identified as having a viral infection.

In another embodiment, the methods of the invention can be used to prompt additional targeted diagnosis such as pathogen specific PCRs, chest-X-ray, cultures etc. For example, a diagnosis that indicates a viral infection according to embodiments of this invention, may prompt the usage of additional viral specific multiplex-PCRs, whereas a diagnosis that indicates a bacterial infection according to embodiments of this invention may prompt the usage of a bacterial specific multiplex-PCR. Thus, one can reduce the costs of unwarranted expensive diagnostics.

In a specific embodiment, a diagnostic test recommendation for a subject is provided by identifying the infection type (i.e., bacterial, viral, mixed infection or no infection) in the subject according to any of the disclosed methods and recommending a test to determine the source of the bacterial infection if the subject is identified as having a bacterial infection or a mixed infection; or a test to determine the source of the viral infection if the subject is identified as having a viral infection.

Performance and Accuracy Measures of the Invention.

The performance and thus absolute and relative clinical usefulness of the invention may be assessed in multiple ways as noted above. Amongst the various assessments of performance, some aspects of the invention are intended to provide accuracy in clinical diagnosis and prognosis. The accuracy of a diagnostic or prognostic test, assay, or method concerns the ability of the test, assay, or method to distinguish between subjects having an infection is based on whether the subjects have, a "significant alteration" (e.g., clinically significant and diagnostically significant) in the levels of a determinant. By "effective amount" it is meant that the measurement of an appropriate number of determinants (which may be one or more) to produce a "significant alteration" (e.g. level of expression or activity of a determinant) that is different than the predetermined cut-off point (or threshold value) for that determinant (s) and therefore indicates that the subject has an infection for which the determinant (s) is an indication. The difference in the level of determinant is preferably statistically significant. As noted below, and without any limitation of the invention, achieving statistical significance, and thus the preferred analytical, diagnostic, and clinical accuracy, may require that combinations of several determinants be used together in panels and combined with mathematical algorithms in order to achieve a statistically significant determinant index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. One way to achieve this is by using the Matthews correlation coefficient (MCC) metric, which depends upon both sensitivity and specificity. Use of statistics such as area under the ROC curve (AUC), encompassing all potential cut point values, is preferred for most categorical risk measures when using some aspects of the invention, while for continuous risk measures, statistics of goodness-of-fit and calibration to observed results or other gold standards, are preferred.

By predetermined level of predictability it is meant that the method provides an acceptable level of clinical or diagnostic accuracy. Using such statistics, an "acceptable degree of diagnostic accuracy", is herein defined as a test or assay (such as the test used in some aspects of the invention for determining the clinically significant presence of determinants, which thereby indicates the presence an infection type) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence or absence of an infection or response to therapy with at least 75% total accuracy, more preferably 80%, 85%, 90%, 95%, 97%, 98%, 99% or greater total accuracy.

Alternatively, the methods predict the presence of a bacterial infection or response to therapy with at least 75% sensitivity, more preferably 80%, 85%, 90%, 95%, 97%, 98%, 99% or greater sensitivity.

Alternatively, the methods predict the presence of a viral infection or response to viral therapy with at least 75% specificity, more preferably 80%, 85%, 90%, 95%, 97%, 98%, 99% or greater specificity.

Alternatively, the methods rule out the presence of a bacterial infection or rule in a viral infection with at least 75% NPV, more preferably 80%, 85%, 90%, 95%, 97%, 98%, 99% or greater NPV. Alternatively, the methods rule in the presence of a bacterial infection or rule out a viral infection with at least 75% PPV, more preferably 80%, 85%, 90%, 95%, 97%, 98%, 99% or greater PPV.

Alternatively, the methods predict the presence of a viral infection or response to therapy with at least 75% specificity, more preferably 80%, 85%, 90%, 95%, 97%, 98%, 99% or greater specificity. Alternatively, the methods predict the presence or absence of an infection or response to therapy with an MCC larger than 0.2, 0.3, 0.4, 0.5, 0.6, 0.7, 0.8, 0.9 or 1.0.

In general, alternative methods of determining diagnostic accuracy are commonly used for continuous measures, when a disease category has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the determinants of the invention allows for one of skill in the art to use the determinants to identify, diagnose, or prognose subjects with a pre-determined level of predictability and performance.

Furthermore, other unlisted biomarkers will be very highly correlated with the determinants (for the purpose of this application, any two variables will be considered to be "very highly correlated" when they have a Coefficient of Determination ($R^2$) of 0.5 or greater). Some aspects of the present invention encompass such functional and statistical equivalents to the aforementioned determinants. Furthermore, the statistical utility of such additional determinants is substantially dependent on the cross-correlation between multiple biomarkers and any new biomarkers will often be required to operate within a panel in order to elaborate the meaning of the underlying biology.

One or more of the listed determinants can be detected in the practice of the present invention, in some embodiments thereof. For example, two (2), three (3), four (4), five (5), ten (10), fifteen (15), twenty (20), forty (40), or more determinants can be detected.

In some aspects, all determinants listed herein can be detected. Preferred ranges from which the number of determinants can be detected include ranges bounded by any minimum selected from between one and, particularly two, three, four, five, six, seven, eight, nine ten, twenty, or forty. Particularly preferred ranges include two to five (2-5), two to ten (2-10), two to twenty (2-20), or two to forty (2-40).

Construction of Determinant Panels

Groupings of determinants can be included in "panels", also called "determinant-signatures", "determinant signatures", or "multi-determinant signatures." A "panel" within the context of the present invention means a group of biomarkers (whether they are determinants, clinical parameters, or traditional laboratory risk factors) that includes one or more determinants. A panel can also comprise additional biomarkers, e.g., clinical parameters, traditional laboratory risk factors, known to be present or associated with infection, in combination with a selected group of the determinants listed herein.

As noted above, many of the individual determinants, clinical parameters, and traditional laboratory risk factors listed, when used alone and not as a member of a multi-biomarker panel of determinants, have little or no clinical use in reliably distinguishing individual normal subjects, subjects at risk for having an infection (e.g., bacterial, viral or co-infection), and thus cannot reliably be used alone in classifying any subject between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

Despite this individual determinant performance, and the general performance of formulas combining only the traditional clinical parameters and few traditional laboratory risk factors, the present inventors have noted that certain specific combinations of two or more determinants can also be used as multi-biomarker panels comprising combinations of determinants that are known to be involved in one or more physiological or biological pathways, and that such information can be combined and made clinically useful through the use of various formulae, including statistical classification algorithms and others, combining and in many cases extending the performance characteristics of the combination beyond that of the individual determinants. These specific combinations show an acceptable level of diagnostic accuracy, and, when sufficient information from multiple determinants is combined in a trained formula, they often reliably achieve a high level of diagnostic accuracy transportable from one population to another.

The general concept of how two less specific or lower performing determinants are combined into novel and more useful combinations for the intended indications, is a key aspect of some embodiments of the invention. Multiple biomarkers can yield significant improvement in performance compared to the individual components when proper mathematical and clinical algorithms are used; this is often evident in both sensitivity and specificity, and results in a greater AUC or MCC. Significant improvement in performance could mean an increase of 1%, 2%, 3%, 4%, 5%, 8%, 10% or higher than 10% in different measures of accuracy such as total accuracy, AUC, MCC, sensitivity, specificity, PPV or NPV. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

On the other hand, it is often useful to restrict the number of measured diagnostic determinants (e.g., protein biomarkers), as this allows significant cost reduction and reduces required sample volume and assay complexity. Accordingly, even when two signatures have similar diagnostic performance (e.g., similar AUC or sensitivity), one which incorporates fewer proteins could have significant utility and ability to reduce to practice. For example, a signature that includes 5 proteins compared to 10 proteins and performs similarly has many advantages in real world clinical setting and thus is desirable. Therefore, there is value and invention in being able to reduce the number of proteins incorporated in a signature while retaining similar levels of accuracy. In this context similar levels of accuracy could mean plus or minus 1%, 2%, 3%, 4%, 5%, 8%, or 10% in different measures of accuracy such as total accuracy, AUC, MCC, sensitivity, specificity, PPV or NPV; a significant reduction in the number of genes of a signature includes reducing the number of genes by 2, 3, 4, 5, 6, 7, 8, 9, 10 or more than 10 genes.

Several statistical and modeling algorithms known in the art can be used to both assist in determinant selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the determinants can be advantageously used. Pathway informed seeding of such statistical classification techniques also may be employed, as may rational approaches based on the selection of individual determinants based on their participation across in particular pathways or physiological functions.

Ultimately, formula such as statistical classification algorithms can be directly used to both select determinants and to generate and train the optimal formula necessary to combine the results from multiple determinants into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of determinants used. The position of the individual determinant on a forward or backwards selected panel can be closely related to its provision of incremental information content for the algorithm, so the order of contribution is highly dependent on the other constituent determinants in the panel.

Construction of Clinical Algorithms

Any formula may be used to combine determinant results into indices useful in the practice of the invention. As indicated above, and without limitation, such indices may indicate, among the various other indications, the probability, likelihood, absolute or relative risk, time to or rate of conversion from one to another disease states, or make predictions of future biomarker measurements of infection.

This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from determinant results in the relevant training population. Amongst other uses, such formula may be intended to map the feature space derived from one or more determinant inputs to a set of subject classes (e.g. useful in predicting class membership of subjects as normal, having an infection), to derive an estimation of a probability function of risk using a Bayesian approach, or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual determinant measurements into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art. Of particular interest are a set of normalizations based on clinical-determinants such as time from symptoms, gender, race, or sex, where specific formula are used solely on subjects within a class or continuously combining a clinical-determinants as an input. In other cases, analyte-based biomarkers can be combined into calculated variables which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al., (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al., 2004 on the limitations of odds ratios; Cook, N. R., 2007 relating to ROC curves. Finally, the numeric result of a classifier formula itself may be transformed post-processing by its reference to an actual clinical population and study results and observed endpoints, in order to calibrate to absolute risk and provide confidence intervals for varying numeric results of the classifier or risk formula.

There are various ways (and formulations) to combine two biomarkers into one predictive score. For example, using dual cutoffs—one for each biomarker, generates a quadrary separation pattern that can separate between bacterial, viral and mixed (bacterial-viral co-infection) patients. For some biomarkers, adding another cutoff also enables the identification of healthy patients by generating a separation pattern composed of six units. Alternatively, the separation between bacterial and viral patients could be based on the ratio between the two biomarkers. Using a defined cutoff for the ratio between the two biomarkers generates a line that separates between bacterial and viral zones.

Another way to combine two biomarkers is using statistical classification algorithms that can generate various unique separation hyperplanes that distinguish between two groups of patients with high levels of accuracy in a cutoff independent manner. Importantly, cutoff independent models (generated for example using statistical classification algorithms) can provide a likelihood score (e.g., 90% chance for bacterial infection) compared to a binary result (bacterial or viral result only) obtained using defined cutoffs and a quadrary/six units separation patterns. Thus, it can provide additional clinical information that can guide correct patient management. Examples for statistical classification algorithms include Artificial Neural Networks (ANN), Support Vector Machines (SVM), Bayesian Networks (BN), K-Nearest Neighbor (KNN) and Logistic Regression.

Thus, certain embodiments of this invention include combining two polypeptides, the first being TRAIL and the second being selected from the list of polypeptides that includes for example CRP, PCT, IL-6, IP-10, MX1, IL1RA for early ruling in of bacterial infections.

In another embodiment, the separation is based on the ratio between the two biomarkers using a defined cutoff.

In yet another embodiment, the combination of the two biomarkers is performed in a cutoff independent manner using statistical classification algorithms.

Some determinants may exhibit trends that depends on the patient age (e.g. the population baseline may rise or fall as a function of age). One can use an 'Age dependent normalization or stratification' scheme to adjust for age related differences. Performing age dependent normalization, stratification or distinct mathematical formulas can be used to improve the accuracy of determinants for differentiating between different types of infections. For example, one skilled in the art can generate a function that fits the population mean levels of each determinant as function of age and use it to normalize the determinant of individual subjects levels across different ages. Another example is to stratify subjects according to their age and determine age specific thresholds or index values for each age group independently.

In the context of the present invention the following statistical terms may be used:

"TP" is true positive, means positive test result that accurately reflects the tested-for activity. For example in the context of the present invention a TP, is for example but not limited to, truly classifying a bacterial infection as such.

"TN" is true negative, means negative test result that accurately reflects the tested-for activity. For example in the context of the present invention a TN, is for example but not limited to, truly classifying a viral infection as such.

"FN" is false negative, means a result that appears negative but fails to reveal a situation. For example in the context of the present invention a FN, is for example but not limited to, falsely classifying a bacterial infection as a viral infection.

"FP" is false positive, means test result that is erroneously classified in a positive category. For example in the context of the present invention a FP, is for example but not limited to, falsely classifying a viral infection as a bacterial infection.

"Sensitivity" is calculated by TP/(TP+FN) or the true positive fraction of disease subjects.

"Specificity" is calculated by TN/(TN+FP) or the true negative fraction of non-disease or normal subjects.

"Total accuracy" is calculated by (TN+TP)/(TN+FP+TP+FN).

"Positive predictive value" or "PPV" is calculated by TP/(TP+FP) or the true positive fraction of all positive test results. It is inherently impacted by the prevalence of the disease and pre-test probability of the population intended to be tested.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test.

"MCC" (Mathwes Correlation coefficient) is calculated as follows: MCC=(TP*TN−FP*FN)/{(TP+FN)*(TP+FP)*(TN+FP)*(TN+FN)}^0.5 where TP, FP, TN, FN are true-positives, false-positives, true-negatives, and false-negatives, respectively. Note that MCC values range between −1 to +1, indicating completely wrong and perfect classification, respectively. An MCC of 0 indicates random classification. MCC has been shown to be a useful for combining sensitivity and specificity into a single metric (Baldi, Brunak et al. 2000). It is also useful for measuring and optimizing classification accuracy in cases of unbalanced class sizes (Baldi, Brunak et al. 2000).

Often, for binary disease state classification approaches using a continuous diagnostic test measurement, the sensitivity and specificity is summarized by a Receiver Operating Characteristics (ROC) curve according to Pepe et al., "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4$^{th}$ edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), Matheus correlation coefficient (MCC), or as a likelihood, odds ratio, Receiver Operating Characteristic (ROC) curve, Area Under the Curve (AUC) among other measures.

A "formula," "algorithm," or "model" is any mathematical equation, algorithmic, analytical or programmed process, or statistical technique that takes one or more continuous or categorical inputs (herein called "parameters") and calculates an output value, sometimes referred to as an "index" or "index value". Non-limiting examples of "formulas" include sums, ratios, and regression operators, such as coefficients or exponents, biomarker value transformations and normalizations (including, without limitation, those normalization schemes based on clinical-determinants, such as gender, age, or ethnicity), rules and guidelines, statistical classification models, and neural networks trained on historical populations. Of particular use in combining determinants are linear and non-linear equations and statistical classification analyses to determine the relationship between levels of determinants detected in a subject sample and the subject's probability of having an infection or a certain type of infection. In panel and combination construction, of particular interest are structural and syntactic statistical classification algorithms, and methods of index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shrunken Centroids (SC), StepAIC, Kth-Nearest Neighbor, Boosting, Decision Trees, Neural Networks, Bayesian Networks, and Hidden Markov Models, among others. Other techniques may be used in survival and time to event hazard analysis, including Cox, Weibull, Kaplan-Meier and Greenwood models well known to those of skill in the art. Many of these techniques are useful either combined with a determinant selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Bootstrap, Leave-One-Out (LOO) and 10-Fold cross-validation (10-Fold CV). At various steps, false discovery rates may be estimated by value permutation according to techniques known in the art. A "health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (a.k.a., zero predicted subject outcome misclassifications or FP and FN), which all performance measures will favor over imperfection, but to differing degrees.

"Analytical accuracy" refers to the reproducibility and predictability of the measurement process itself, and may be summarized in such measurements as coefficients of variation (CV), Pearson correlation, and tests of concordance and calibration of the same samples or controls with different times, users, equipment and/or reagents. These and other considerations in evaluating new biomarkers are also summarized in Vasan, 2006.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test, and may be measured by appropriate "performance metrics," such as AUC and MCC, time to result, shelf life, etc. as relevant.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

In the context of the present invention the following abbreviations may be used: Antibiotics (Abx), Adverse Event (AE), Arbitrary Units (A.U.), Complete Blood Count (CBC), Case Report Form (CRF), Chest X-Ray (CXR), Electronic Case Report Form (eCRF), Food and Drug Administration (FDA), Good Clinical Practice (GCP), Gastrointestinal (GI), Gastroenteritis (GE), International Conference on Harmonization (ICH), Infectious Disease (ID), In vitro diagnostics (IVD), Lower Respiratory Tract Infection (LRTI), Myocardial infarction (MI), Polymerase chain reaction (PCR), Per-oss (P.O), Per-rectum (P.R), Standard of Care (SoC), Standard Operating Procedure (SOP), Urinary Tract Infection (UTI), Upper Respiratory Tract Infection (URTI).

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Methods

Study Population:

1002 patients with suspected acute infectious disease and non-infectious controls were prospectively recruited between August 2009 and November 2013 from Hillel-Yaffe and Bnai-Zion Medical Centers, Israel (NCT01917461). The study was approved by the Hillel-Yaffe Medical Center Institutional Review Board, and the Bnai-Zion Medical Center Institutional Review Board. The study was conducted according to the guidelines and recommendations of Good Clinical Practice and the Declaration of Helsinki. Written informed consent was obtained from each participant or legal guardian, as applicable.

Pediatric patients (≤18 years) were recruited from pediatric emergency departments (PED), pediatric wards and surgical departments, and adults (>18 years) from emergency departments (ED), internal medicine departments and surgical departments. Informed consent was obtained from each participant or legal guardian, as applicable. Inclusion criteria for the infectious disease cohort included: clinical suspicion of an acute infectious disease, peak fever >37.5° C. since symptoms onset, and duration of symptoms ≤12 days. Inclusion criteria for the control group included: clinical impression of a non-infectious disease (e.g. trauma, stroke and myocardial infarction), or healthy subjects. Exclusion criteria included: evidence of any episode of acute infectious disease in the two weeks preceding enrollment; diagnosed congenital immune deficiency; current treatment with immunosuppressive or immunomodulatory therapy; active malignancy, proven or suspected human immunodeficiency virus (HIV)-1, hepatitis B virus (HBV), or hepatitis C virus (HCV) infection. Importantly, in order to enable broad generalization, antibiotic treatment at enrollment did not cause exclusion from the study.

Enrollment Process and Data Collection:

For each patient, the following baseline variables were recorded: demographics, physical examination, medical history (e.g. main complaints, underlying diseases, chronically-administered medications, comorbidities, time of symptom onset, and peak temperature), complete blood count (CBC) obtained at enrollment, and chemistry panel (e.g. creatinine, urea, electrolytes, and liver enzymes). A nasal swab was obtained from each patient for further microbiological investigation, and a blood sample was obtained for protein screening and validation. Additional samples were obtained as deemed appropriate by the physician (e.g. urine and stool samples in cases of suspected urinary tract infection [UTI], and gastroenteritis [GI] respectively). Radiological tests were obtained at the discretion of the physician (e.g. chest X-ray for suspected lower respiratory tract infection [LRTI]). Thirty days after enrollment, disease course and response to treatment were recorded. All information was recorded in a custom electronic case report form (eCRF).

Microbiological Investigation:

Patients underwent two multiplex-PCR diagnostic assays from nasal swab samples: (i) Seeplex® RV15 (n=713), for detection of parainfluenza virus 1, 2, 3, and 4, coronavirus 229E/NL63, adenovirus A/B/C/D/E, bocavirus 1/2/3/4, influenza virus A and B, metapneumovirus, coronavirus OC43, rhinovirus A/B/C, respiratory syncytial virus A and B, and Enterovirus, and (ii) Seeplex® PB6 (n=633) for detection of Streptococcus pneumoniae, Haemophilus influenzae, Chlamydophila pneumoniae, Legionella pneumophila, Bordetella pertussis, and Mycoplasma pneumoniae. Multiplex-PCR assays were performed by a certified service laboratory. Patients were also tested for additional pathogens according to their suspected clinical syndrome, including: blood culture (n=420), urine culture (n=188) and stool culture for Shigella spp., Campylobacter spp. and Salmonella spp. (n=66); serological testing (IgM and/or IgG) for cytomegalovirus (CMV), Epstein-Barr virus (EBV), Mycoplasma Pneumonia, and Coxiella burnetii (Q-Fever) (n=167, n=130, n=206 and n=41 respectively).

Establishing the Reference Standard:

A rigorous composite reference standard was created following recommendations of the Standards for Reporting of Diagnostic Accuracy (STARD; FIG. 1).[1] First, a thorough clinical and microbiological investigation was performed for each patient as described above. Then, all the data collected throughout the disease course was reviewed by a panel of three physicians. For adult patients (>18 years) the panel included the attending physician and two infectious disease specialists, while for children and adolescents (≤18 years) it included the attending pediatrician, an infectious disease expert and a senior attending pediatrician. Each panel member assigned one of the following diagnostic labels to each patient: (i) bacterial; (ii) viral; (iii) no apparent infectious disease or healthy (controls); and (iv) mixed infections (bacteria plus virus). Importantly, the panel members were blinded to the labeling of their peers and to the results of the signature.

Samples, Procedures and Protein Measurements:

Venous blood samples were stored at 4° C. for up to 5 hours on site and subsequently fractionated into plasma, serum and total leukocytes and stored at −80° C. Nasal swabs and stool samples were stored at 4° C. for up to 72 hours and subsequently transported to a certified service laboratory for multiplex PCR-based assay. TRAIL protein was measured using commercial ELISA kits (MeMed Diagnostics).

Statistical Analysis:

The primary analysis was based on area under the receiver operating characteristics curve (AUC), Sensitivity (TP/P), Specificity (TN/N), Positive predictive value (PPV=TP/[TP+FP]), Negative predictive value (NPV=TN/[TN+FN]), where P, N, TP and TN correspond to positives (bacterial patients), negatives (viral patients), true positives (correctly diagnosed bacterial patients), and true negatives (correctly diagnosed viral patients), respectively. Statistical analysis was performed with MATLAB.

Results

Patient Characteristics:

Three physicians independently assigned a label to each patient (either bacterial, viral, controls, or indeterminate). 98 patients were labeled as indeterminate, because the physicians could not establish disease etiology or there was no majority labeling. A detailed characterization of the analyzed cohort is depicted in FIGS. 2-7. Briefly, the cohort was balanced with respect to gender (47% females, 53% males) and included 56% pediatric patients (≤18 years) and 44% adults (>18 years). Patients presented with a wide range of clinical syndromes (e.g. RTI, UTI, and systemic infections), maximal temperatures (36-41.5° C.), and time from symptoms onset (0-12 days). Altogether, 56 pathogen species were detected that are responsible for the vast majority of acute infectious diseases in the Western world.

TRAIL as a Diagnostic Marker for Diagnosing Bacterial Infections

TRAIL is a valuable biomarker for distinguishing between bacterial and viral infections as unlike known biomarkers, the serum levels of TRAIL decrease in response to bacterial infections and increase in response to viral infections (FIG. 8). The accuracy levels of TRAIL in distinguishing between bacterial and viral infections depend on the cutoff that is used. Table 4 presents the measures of accuracy in two exemplary TRAIL cutoffs (70 and 85 pg/ml).

TABLE 4

Measures of accuracy of TRAIL in distinguishing between patients with bacterial (n = 319) and viral (n = 334) infections, using different cutoffs as indicated.

| Cutoff | Sensitivity | Specificity | PPV | NPV |
|---|---|---|---|---|
| TRAIL < 70 pg/ml | 0.83 | 0.78 | 0.78 | 0.79 |
| TRAIL < 85 pg/ml | 0.9 | 0.66 | 0.82 | 0.80 |

Sub-Group Analysis

The present inventors further evaluated the ability of TRAIL to distinguish between bacterial and viral infections in various patient sub-groups. Patients were stratified according to several categories (i.e., clinical syndrome;

specific pathogen; and age), and measures of accuracy were calculated for TRAIL using exemplary cutoffs.

Examples of Specific Pathogens

TRAIL presented superior performances in disguising between *E. coli*, Group A Strep, or *Enterococcus faecalis* and viruses affecting the same physiological system in the exemplary TRAIL cutoffs that were evaluated (Tables 5 and 6).

TABLE 5

Measures of accuracy of TRAIL in distinguishing between patients with viral and different bacterial infections as indicated (TRAIL cutoffs 70 pg/ml). Bacteria was compared to virus affecting the same physiological system as indicated.

| Bacteria | Sensitivity | Specificity | Physiological system |
|---|---|---|---|
| *E. coli* | 0.89 | 0.83 | Urinary, systemic |
| Group A Strep | 0.93 | 0.79 | Respiratory, systemic, skin |
| *Enterococcus faecalis* | 1.00 | 0.83 | Urinary, systemic |

TABLE 6

Measures of accuracy of TRAIL in distinguishing between patients with viral and different bacterial infections as indicated (TRAIL cutoff 85 pg/ml). Bacteria was compared to virus affecting the same physiological system as indicated.

| Bacteria | Sensitivity | Specificity | Physiological system |
|---|---|---|---|
| *E. coli* | 0.95 | 0.74 | Urinary, systemic |
| Group A Strep | 1.00 | 0.67 | Respiratory, systemic, skin |
| *Enterococcus faecalis* | 1.00 | 0.74 | Urinary, systemic |

Examples of Clinical Syndromes

TRAIL presented superior performances in disguising between bacterial and viral infections in patients with various clinical syndromes including serious bacterial infection (SBI), upper respiratory tract infection (UTRI), lower respiratory tract infection (LRTI), and fever without source (FWS; Table 7).

TABLE 7

Measures of accuracy of TRAIL (cutoff 85 pg/ml) in distinguishing between viral and bacterial infections in patients presented with different clinical syndromes as indicated (SBI—serious bacterial infection; UTRI—upper respiratory tract infection; LRTI—lower respiratory tract infection; FWS—fever without source).

| Clinical syndrome | Sensitivity | Specificity |
|---|---|---|
| SBI | 0.90 | 0.47 |
| URTI | 0.97 | 0.66 |
| LRTI | 0.85 | 0.53 |
| FWS | 0.92 | 0.72 |

Age

TRAIL accuracy measures exhibit some level of difference. For example, sensitivity of TRAIL was higher in the adults group (>18 years old), while the specificity was higher in the pediatric group (<18 years old; Table 8; TRAIL cutoff 70 pg/ml).

TABLE 8

Measures of accuracy of TRAIL (cutoff 70 pg/ml) in distinguishing between viral and bacterial infections in adult (n = 251) and pediatric (n = 402) patients as indicated.

| Age group | Sensitivity | Specificity |
|---|---|---|
| Adult (>18) | 0.84 | 0.71 |
| Children (<18) | 0.81 | 0.79 |

TRAIL is Particularly Useful for Early Diagnosis of Bacterial Infections

Delayed or no antibiotic treatment in cases of bacterial disease is very common (24%-40% of all bacterial infections)[4-7], and can lead to disease-related complications resulting in increased rates of morbidity and mortality[8-10]. Thus, timely identification of patients with bacterial infection is of great importance to guide correct patient management. The present inventors therefore, evaluated the performance of TRAIL in different stages of disease progression. Interestingly, it was found that TRAIL levels are already significantly different in patients with bacterial and viral infection at the first days from symptoms onset (FIG. 10). Moreover, the accuracy levels of TRAIL in distinguishing between patients with bacterial and viral infections were higher in the first days following symptoms onset using different TRAIL cutoffs (Tables 9 and 10).

TABLE 9

Measures of accuracy of TRAIL (cutoff 85 pg/ml) in distinguishing between viral and bacterial infections in different days from symptoms onset as indicated.

| | Days 0-1 | Days >1 | Days 0-2 | Days >2 |
|---|---|---|---|---|
| Sensitivity | 0.93 | 0.89 | 0.92 | 0.89 |
| Specificity | 0.67 | 0.66 | 0.69 | 0.64 |

TABLE 10

Measures of accuracy of TRAIL (cutoff 70 pg/ml) in distinguishing between viral and bacterial infections in different days from symptoms onset as indicated.

| | Days 0-1 | Days >1 | Days 0-2 | Days >2 |
|---|---|---|---|---|
| Sensitivity | 0.87 | 0.82 | 0.85 | 0.81 |
| Specificity | 0.78 | 0.78 | 0.81 | 0.75 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Bossuyt, P. M. et al. The STARD Statement for Reporting Studies of Diagnostic Accuracy: Explanation and Elaboration. *Ann Intern Med* 138, W1-W12 (2003).
2. Kunze, W., Beier, D. & Groeger, K. Adenovirus Respiratory Infections In Children. Do They Mimic Bacterial Infections? (2010).
3. Oved, K. et al. A Novel Host-Proteome Signature for Distinguishing between Acute Bacterial and Viral Infections. *PLoS ONE* 10, e0120012 (2015).
4. Craig, J. C. et al. The accuracy of clinical symptoms and signs for the diagnosis of serious bacterial infection in young febrile children: prospective cohort study of 15 781 febrile illnesses. *BMJ* 340, (2010).
5. Dedier, J., Singer, D. E., Chang, Y., Moore, M. & Atlas, S. J. Processes of care, illness severity, and outcomes in the management of community-acquired pneumonia at academic hospitals. *Arch. Intern. Med.* 161, 2099-2104 (2001).
6. Caterino, J. M., Hiestand, B. C. & Martin, D. R. Quality of care in elder emergency department patients with pneumonia: a prospective cohort study. *BMC Emerg Med* 8, 6 (2008).
7. Houck, P. M. Timing of antibiotic administration and outcomes for medicare patients hospitalized with community-acquired pneumonia. *Arch Intern Med* 164, 637-644 (2004).
8. Zwart, S. et al. Penicillin for acute sore throat: randomised double blind trial of seven days versus three days treatment or placebo in adults. *BMJ* 320, 150-154 (2000).
9. Little, P. Delayed prescribing of antibiotics for upper respiratory tract infection. *BMJ* 331, 301-302 (2005).
10. Spiro, D. M. et al. Wait-and-see prescription for the treatment of acute otitis media: a randomized controlled trial. *JAMA* 296, 1235-1241 (2006).
11. Fauci A S & Marston H D. The perpetual challenge of antimicrobial resistance. *JAMA* (2014). doi:10.1001/jama.2014.2465.
12. CDC—Get Smart: Fast Facts About Antibiotic Resistance. (2011). Available at: www(dot)cdc(dot)gov/getsmart/antibiotic-use/fast-facts(dot)html. (Accessed: 21 Nov. 2011).
13. CDC—About Antimicrobial Resistance. (2011). Available at: www(dot)cdc(dot)gov/drugresistance/about(dot) html. (Accessed: 21 Nov. 2011).
14. Niemz, A., Ferguson, T. M. & Boyle, D. S. Point-of-care nucleic acid testing for infectious diseases. *Trends Biotechnol.* 29, 240-250 (2011).
15. Craw, P. & Balachandran, W. Isothermal nucleic acid amplification technologies for point-of-care diagnostics: a critical review. *Lab Chip* 12, 2469-2486 (2012).
16. Kim, K. H., Shin, J. H. & Kim, S. Y. The Clinical Significance of Nasopharyngeal Carriages in Immunocompromised Children as Assessed. *The Korean Journal of Hematology* 44, 220 (2009).
17. Shin, J. H., Han, H. Y. & Kim, S. Y. Detection of nasopharyngeal carriages in children by multiplex reverse transcriptase-polymerase chain reaction. *Korean Journal of Pediatrics* 52, 1358 (2009).
18. Jung, C. L., Lee, M. A. & Chung, W. S. Clinical Evaluation of the Multiplex PCR Assay for the Detection of Bacterial Pathogens in Respiratory Specimens from Patients with Pneumonia. *Korean Journal of Clinical Microbiology* 13, 40 (2010).
19. Rhedin, S. et al. Clinical Utility of PCR for Common Viruses in Acute Respiratory Illness. *Pediatrics peds.* 2013-3042 (2014). doi:10.1542/peds.2013-3042.
20. Bogaert, D., De Groot, R. & Hermans, P. W. M. *Streptococcus pneumoniae* colonisation: the key to pneumococcal disease. *Lancet Infect Dis* 4, 144-154 (2004).
21. Spuesens, E. B. M. et al. Carriage of *Mycoplasma pneumoniae* in the Upper Respiratory Tract of Symptomatic and Asymptomatic Children: An Observational Study. *PLoS Med* 10, e1001444 (2013).
22. Salvi, S. The silent epidemic of COPD in Africa. *Lancet Glob Health* 3, e6-7 (2015).
23. GOLD—the Global initiative for chronic Obstructive Lung Disease. Available at: www(dot)goldcopd(dot)org/ guidelines-global-strategy-for-diagnosis-management (dot)html. (Accessed: 15 Apr. 2015).
24. WHO|The top 10 causes of death. WHO Available at: www(dot)who(dot)int/mediacentre/factsheets/fs310/en/. (Accessed: 17 Mar. 2015).
25. Global Problems, Smart Solutions. Cambridge University Press Available at: www (dot)cambridge(dot)org/il/ academic/subjects/economic s/public-economics-and-public-policy/global-problems-smart-solutions-costs-and-benefits. (Accessed: 15 Apr. 2015).
26. Hoogendoorn, M. Economic impact of COPD: Empirical and model-based studies on the cost-effectiveness of treatment options. *Journal of Neurophysiology—J NEUROPHYSIOL* (2011).
27. Hurst, J. R. et al. Susceptibility to exacerbation in chronic obstructive pulmonary disease. *N. Engl. J. Med.* 363, 1128-1138 (2010).
28. Kim, V. et al. Airway wall thickness is increased in COPD patients with bronchodilator responsiveness. *Respir. Res.* 15, 84 (2014).
29. Bhowmik, A., Seemungal, T. A., Sapsford, R. J. & Wedzicha, J. A. Relation of sputum inflammatory markers to symptoms and lung function changes in COPD exacerbations. *Thorax* 55, 114-120 (2000).
30. Molyneaux, P. L. et al. Outgrowth of the bacterial airway microbiome after rhinovirus exacerbation of chronic obstructive pulmonary disease. *Am. J. Respir. Crit. Care Med.* 188, 1224-1231 (2013).
31. Taylor, A. E. et al. Defective macrophage phagocytosis of bacteria in COPD. *Eur. Respir. J.* 35, 1039-1047 (2010).
32. Sethi, S., Evans, N., Grant, B. J. B. & Murphy, T. F. New strains of bacteria and exacerbations of chronic obstructive pulmonary disease. *N. Engl. J. Med.* 347, 465-471 (2002).
33. Lin, C.-L. et al. MAnnose-binding lectin gene polymorphism contributes to recurrence of infective exacerbation in patients with copd. *Chest* 139, 43-51 (2011).

What is claimed is:

1. A method of treating a human subject showing symptoms of a pathogenic infection comprising:
   (a) receiving an identification that the subject has a level of TNF-related apoptosis-inducing ligand (TRAIL) below 70 pg/ml in a blood sample, said blood sample being isolated from the subject no more than two days following symptom onset; and
   (b) administering to the subject an antibiotic agent.

2. The method of claim 1, wherein said symptoms of a pathogenic infection comprise fever.

3. The method of claim 1, wherein the sample is isolated from the subject no more than one day following symptom onset.

4. The method of claim 1, wherein the sample is whole blood or a fraction thereof.

5. The method of claim 1, further comprising analyzing a level of C-reactive protein (CRP) and/or Interferon gamma-induced protein 10 (IP10).

6. The method of claim 1, further comprising analyzing a level of a polypeptide selected from the group consisting of Interferon gamma-induced protein 10 (IP10), Interleukin 6 (IL-6), and Interleukin 1 receptor, type I (IL1RA).

7. The method of claim 1, further comprising analyzing a level of a polypeptide selected from the group consisting of Interferon gamma-induced protein 10 (IP10), Interleukin 6 (IL-6), Interleukin 1 receptor, type I (IL1RA), C-reactive protein (CRP) and procalcitonin (PCT).

8. The method of claim 1, wherein said TRAIL is measured using a lateral flow immunoassay.

9. The method of claim 8, wherein said TRAIL is measured using an antibody which binds specifically to TRAIL.

10. The method of claim 9, wherein said antibody is a monoclonal antibody.

* * * * *

SEQUENCE LISTING

<160> NUMBER OF SEQ ID NOS: 24

<210> SEQ ID NO 1
<211> LENGTH: 224
<212> TYPE: PRT
<213> ORGANISM: homo sapiens

<400> SEQUENCE: 1

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
            20                  25                  30

Ser Asp Thr Ser Tyr Val Ser Leu Lys Ala Pro Leu Thr Lys Pro Leu
        35                  40                  45

Lys Ala Phe Thr Val Cys Leu His Phe Tyr Thr Glu Leu Ser Ser Thr
    50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140

Val Gly Ala Glu Ala Ser Ile Ile Leu Gly Gln Glu Gln Asp Ser Phe
145                 150                 155                 160

Gly Gly Asn Phe Glu Gly Ser Gln Ser Leu Val Gly Asp Ile Gly Asn
                165                 170                 175

Val Asn Met Trp Asp Phe Val Leu Ser Pro Asp Glu Ile Asn Thr Ile
            180                 185                 190

Tyr Leu Gly Gly Pro Phe Ser Pro Asn Val Leu Asn Trp Arg Ala Leu
        195                 200                 205

Lys Tyr Glu Val Gln Gly Glu Val Phe Thr Lys Pro Gln Leu Trp Pro
    210                 215                 220

<210> SEQ ID NO 2
<211> LENGTH: 1805
<212> TYPE: DNA
<213> ORGANISM: homo sapiens

<400> SEQUENCE: 2
acagaaccca gaaaacaac tcattcgctt tcatttcctc actgactata aagaataga         60 gaaggaaggg cttcagtgac cggctgcctg gctgacttac agcagtcaga ctctgacagg      120
atcatggcta tgatggaggt ccagggggga cccagcctgg acagacctg cgtgctgatc       180 gtgatcttca cagtgctcct gcagtctctc tgtgtggctg taacttacgt gtactttacc     240
aacgagctga agcagatgca ggacaagtac tccaaaagtg gcattgcttg tttcttaaaa     300
gaagatgaca gttattggga ccccaatgac gaagagagta tgaacagccc ctgctggcaa     360
gtcaagtggc aactccgtca gctcgttaga aagactccaa gaatgaaaag gctctgggcc     420
gcaaaataaa ctcctgggaa tcatcaagga gtgggcattc attcctgagc aacttgcact     480
tgaggaatgg tgaactggtc atccatgaaa aagggttta ctacatctat tcccaaacat     540
actttcgatt tcaggaggaa ataaagaaa acacaaagaa cgacaaacaa atggtccaat     600

```
atatttacaa atacacaagt tatcctgacc ctatattgtt gatgaaaagt gctagaaata      660
gttgttggtc taaagatgca gaatatggac tctattccat ctatcaaggg ggaatatttg      720
agcttaagga aaatgacaga attttttgttt ctgtaacaaa tgagcacttg atagacatgg     780
accatgaagc cagttttttt ggggcctttt tagttggcta actgacctgg aaagaaaaag      840
caataacctc aaagtgacta ttcagttttc aggatgatac actatgaaga tgtttcaaaa      900
aatctgacca aaacaaacaa acagaaaaca gaaaacaaaa aaacctctat gcaatctgag      960
tagagcagcc acaaccaaaa aattctacaa cacacactgt tctgaaagtg actcacttat     1020
cccaagagaa tgaaattgct gaaagatctt tcaggactct acctcatatc agtttgctag     1080
cagaaatcta aagactgtc agcttccaaa cattaatgca atggttaaca tcttctgtct      1140
ttataatcta ctccttgtaa agactgtaga agaaagagca caatccatc tctcaagtag      1200 tgtatcacag tagtagcctc caggtttcct taagggacaa catccttaag tcaaaagaga     1260
gaagaggcac cactaaaaga tcgcagtttg cctggtgcag tggctcacac ctgtaatccc     1320
aacattttgg gaacccaagg tgggtagatc acgagatcaa gagatcaaga ccatagtgac     1380
caacatagtg aaaccccatc tctactgaaa gtacaaaaat tagctgggtg tgttggcaca     1440
tgcctgtagt cccagctact tgagaggctg aggcaagaga attgtttgaa cccgggaggc     1500
agaggttgca gtgtggtgag atcatgccac tacactccag cctggcgaca gagcgagact     1560
tggtttcaaa aaaaaaaaaa aaaaaaactt cagtaagtac gtgttatttt tttcaataaa     1620
attctattac agtatgtcat gtttgctgta gtgctcatat ttattgttgt ttttgtttta     1680
gtactcactt gtttcataat atcaagatta ctaaaaatgg gggaaaagac ttctaatctt     1740
tttttcataa tatctttgac acatattaca gaagaaataa atttcttact tttaattttaa    1800 tatga                                                                1805
```

<210> SEQ ID NO 3
<211> LENGTH: 1334
<212> TYPE: DNA
<213> ORGANISM: homo sapiens

<400> SEQUENCE: 3

```
atttcctcac tgactataaa agaatagaga aggaagggct tcagtgaccg gctgcctggc       60
tgacttacag cagtcagact ctgacaggat catggctatg atggaggtcc agggggggacc     120 cagcctggga cagacctgcg tgctgatcgt gatcttcaca gtgctcctgc agtctctctg      180
tgtggctgta acttacgtgt actttaccaa cgagctgaag cagtttgcag aaaatgattg      240
ccagagacta atgtctgggc agcagacagg gtcattgctg ccatcttgaa gtctaccttg      300
ctgagtctac cctgctgacc tcaagcccca tcaaggactg gttgaccctg cctagacaa      360 ccaccgtgtt tgtaacagca ccaagagcag tcaccatgga aatccacttt tcagaaccaa     420
gggcttctgg agctgaagaa caggcaccca gtgcaagagc tttcttttca gaggcacgca     480
aatgaaaata tccccacac gctaccttct gcccccaatg cccaagtgtg ttagttaga      540 gaatatagcc tcagcctatg atatgctgca ggaaactcat attttgaagt ggaaaggatg     600
ggaggaggcg ggggagacgt atcgtattaa ttatcattct tggaataacc acagcacctc     660
acgtcaaccc gccatgtgtc tagtcaccag cattggccaa gttctatagg agaaactacc     720
aaaattcatg atgcaagaaa catgtgaggg tggagagagt gactgggct tcctctctgg      780 atttctattg ttcagaaatc aatatttatg cataaaaagg tctagaaaga gaaacaccaa     840
```

-continued

```
aatgacaatg tgatctctag atggtatgat tatgggtact ttttttcctt tttattttc      900
tatattttac aaattttcta cagggaatgt tataaaaata tccatgctat ccatgtataa     960
ttttcataca gatttaaaga acacagcatt tttatatagt cttatgagaa acaaccata     1020
ctcaaaatta tgcacacaca cagtctgatc tcaccctgt aaacaagaga tatcatccaa     1080
aggttaagta ggaggtgaga atatagctgc tattagtggt tgttttgttt tgttttgtg     1140
atttacttat ttagttttg gagggttttt ttttcttt agaaaagtgt tcttacttt         1200
tccatgcttc cctgcttgcc tgtgtatcct gaatgtatcc aggctttata aactcctggg    1260
taataatgta gctacattaa cttgttaacc tcccatccac ttatacccag gaccttactc    1320
aattttccag gttc                                                      1334
```

<210> SEQ ID NO 4
<211> LENGTH: 281
<212> TYPE: PRT
<213> ORGANISM: homo sapiens

<400> SEQUENCE: 4

```
Met Ala Met Met Glu Val Gln Gly Gly Pro Ser Leu Gly Gln Thr Cys
1               5                   10                  15
Val Leu Ile Val Ile Phe Thr Val Leu Leu Gln Ser Leu Cys Val Ala
            20                  25                  30
Val Thr Tyr Val Tyr Phe Thr Asn Glu Leu Lys Gln Met Gln Asp Lys
        35                  40                  45
Tyr Ser Lys Ser Gly Ile Ala Cys Phe Leu Lys Glu Asp Asp Ser Tyr
    50                  55                  60
Trp Asp Pro Asn Asp Glu Glu Ser Met Asn Ser Pro Cys Trp Gln Val
65                  70                  75                  80
Lys Trp Gln Leu Arg Gln Leu Val Arg Lys Met Ile Leu Arg Thr Ser
                85                  90                  95
Glu Glu Thr Ile Ser Thr Val Gln Glu Lys Gln Gln Asn Ile Ser Pro
            100                 105                 110
Leu Val Arg Glu Arg Gly Pro Gln Arg Val Ala Ala His Ile Thr Gly
        115                 120                 125
Thr Arg Gly Arg Ser Asn Thr Leu Ser Ser Pro Asn Ser Lys Asn Glu
    130                 135                 140
Lys Ala Leu Gly Arg Lys Ile Asn Ser Trp Glu Ser Ser Arg Ser Gly
145                 150                 155                 160
His Ser Phe Leu Ser Asn Leu His Leu Arg Asn Gly Glu Leu Val Ile
                165                 170                 175
His Glu Lys Gly Phe Tyr Tyr Ile Tyr Ser Gln Thr Tyr Phe Arg Phe
            180                 185                 190
Gln Glu Glu Ile Lys Glu Asn Thr Lys Asn Asp Lys Gln Met Val Gln
        195                 200                 205
Tyr Ile Tyr Lys Tyr Thr Ser Tyr Pro Asp Pro Ile Leu Leu Met Lys
    210                 215                 220
Ser Ala Arg Asn Ser Cys Trp Ser Lys Asp Ala Glu Tyr Gly Leu Tyr
225                 230                 235                 240
Ser Ile Tyr Gln Gly Gly Ile Phe Glu Leu Lys Glu Asn Asp Arg Ile
                245                 250                 255
Phe Val Ser Val Thr Asn Glu His Leu Ile Asp Met Asp His Glu Ala
            260                 265                 270
Ser Phe Phe Gly Ala Phe Leu Val Gly
        275                 280
```

<210> SEQ ID NO 5
<211> LENGTH: 101
<212> TYPE: PRT
<213> ORGANISM: homo sapiens

<400> SEQUENCE: 5

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Thr Pro Arg Met Lys Arg
                85                  90                  95

Leu Trp Ala Ala Lys
            100

<210> SEQ ID NO 6
<211> LENGTH: 65
<212> TYPE: PRT
<213> ORGANISM: homo sapiens

<400> SEQUENCE: 6

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Phe Ala Glu Asn
        35                  40                  45

Asp Cys Gln Arg Leu Met Ser Gly Gln Thr Gly Ser Leu Leu Pro
    50                  55                  60

Ser
65

<210> SEQ ID NO 7
<211> LENGTH: 223
<212> TYPE: PRT
<213> ORGANISM: homo sapiens

<400> SEQUENCE: 7

Gln Asp His Gly Tyr Asp Gly Pro Gly Gly Thr Gln Pro Gly Thr
1               5                   10                  15

Asp Leu Arg Ala Asp Arg Asp Leu His Ser Ala Pro Ala Val Ser Leu
            20                  25                  30

Cys Gly Cys Asn Leu Arg Val Leu Tyr Gln Arg Ala Glu Ala Glu Lys
        35                  40                  45

Gln Gln Asn Ile Ser Pro Leu Val Arg Glu Arg Gly Pro Gln Arg Val
    50                  55                  60

Ala Ala His Ile Thr Gly Thr Arg Gly Arg Ser Asn Thr Leu Ser Ser
65                  70                  75                  80

Pro Asn Ser Lys Asn Glu Lys Ala Leu Gly Arg Lys Ile Asn Ser Trp
                85                  90                  95

```
Glu Ser Ser Arg Ser Gly His Ser Phe Leu Ser Asn Leu His Leu Arg
                100                 105                 110

Asn Gly Glu Leu Val Ile His Glu Lys Gly Phe Tyr Tyr Ile Tyr Ser
            115                 120                 125

Gln Thr Tyr Phe Arg Phe Gln Glu Glu Ile Lys Glu Asn Thr Lys Asn
        130                 135                 140

Asp Lys Gln Met Val Gln Tyr Ile Tyr Lys Tyr Thr Ser Tyr Pro Asp
145                 150                 155                 160

Pro Ile Leu Leu Met Lys Ser Ala Arg Asn Ser Cys Trp Ser Lys Asp
                165                 170                 175

Ala Glu Tyr Gly Leu Tyr Ser Ile Tyr Gln Gly Gly Ile Phe Glu Leu
            180                 185                 190

Lys Glu Asn Asp Arg Ile Phe Val Ser Val Thr Asn Glu His Leu Ile
        195                 200                 205

Asp Met Asp His Glu Ala Ser Phe Phe Gly Ala Phe Leu Val Gly
    210                 215                 220

<210> SEQ ID NO 8
<211> LENGTH: 178
<212> TYPE: PRT
<213> ORGANISM: homo sapiens

<400> SEQUENCE: 8

Lys Glu Lys Gln Gln Asn Ile Ser Pro Leu Val Arg Glu Arg Gly Pro
1               5                   10                  15

Gln Arg Val Ala Ala His Ile Thr Gly Thr Arg Gly Arg Ser Asn Thr
            20                  25                  30

Leu Ser Ser Pro Asn Ser Lys Asn Glu Lys Ala Leu Gly Arg Lys Ile
        35                  40                  45

Asn Ser Trp Glu Ser Ser Arg Ser Gly His Ser Phe Leu Ser Asn Leu
    50                  55                  60

His Leu Arg Asn Gly Glu Leu Val Ile His Glu Lys Gly Phe Tyr Tyr
65                  70                  75                  80

Ile Tyr Ser Gln Thr Tyr Phe Arg Phe Gln Glu Glu Ile Lys Glu Asn
                85                  90                  95

Thr Lys Asn Asp Lys Gln Met Val Gln Tyr Ile Tyr Lys Tyr Thr Ser
            100                 105                 110

Tyr Pro Asp Pro Ile Leu Leu Met Lys Ser Ala Arg Asn Ser Cys Trp
        115                 120                 125

Ser Lys Asp Ala Glu Tyr Gly Leu Tyr Ser Ile Tyr Gln Gly Gly Ile
    130                 135                 140

Phe Glu Leu Lys Glu Asn Asp Arg Ile Phe Val Ser Val Thr Asn Glu
145                 150                 155                 160

His Leu Ile Asp Met Asp His Glu Ala Ser Phe Phe Gly Ala Phe Leu
                165                 170                 175

Val Gly

<210> SEQ ID NO 9
<211> LENGTH: 2301
<212> TYPE: DNA
<213> ORGANISM: homo sapiens

<400> SEQUENCE: 9
aaggcaagag atctaggact tctagcccct gaactttcag ccgaatacat ctttccaaa      60 ggagtgaatt caggcccttg tatcactggc agcaggacgt gaccatggag aagctgttgt    120
```

| | | |
|---|---|---|
| gtttcttggt cttgaccagc ctctctcatg cttttggcca gacaggtaag ggccacccca | 180 | |
| ggctatggga gagatttgat ctgaggtatg ggggtgggt ctaagactgc atgaacagtc | 240 | |
| tcaaaaaaaa aaaaaaaaga ctgtatgaac agaacagtgg agcatccttc atggtgtgtg | 300 | |
| tgtgtgtgtg tgtgtgtgtg tgtgtgtgtg tggtgtgtaa ctggagaagg ggtcagtctg | 360 | |
| tttctcaatc ttaaattcta tacgtaagtg aggggataga tctgtgtgat ctgagaaacc | 420 | |
| tctcacattt gcttgttttt ctggctcaca gacatgtcga ggaaggcttt tgtgtttccc | 480 | |
| aaagagtcgg atacttccta tgtatccctc aaagcaccgt taacgaagcc tctcaaagcc | 540 | |
| ttcactgtgt gcctccactt ctacacggaa ctgtcctcga cccgtgggta cagtattttc | 600 | |
| tcgtatgcca ccaagagaca agacaatgag attctcatat tttggtctaa ggatatagga | 660 | |
| tacagttta cagtgggtgg gtctgaaata ttattcgagg ttcctgaagt cacagtagct | 720 | |
| ccagtacaca tttgtacaag ctgggagtcc gcctcaggga tcgtggagtt ctgggtagat | 780 | |
| ggaagccca gggtgaggaa gagtctgaag aagggataca ctgtggggc agaagcaagc | 840 | |
| atcatcttgg ggcaggagca ggattccttc ggtgggaact ttgaaggaag ccagtccctg | 900 | |
| gtgggagaca ttggaaatgt gaacatgtgg gactttgtgc tgtcaccaga tgagattaac | 960 | |
| accatctatc ttggcgggcc cttcagtcct aatgtcctga actggcgggc actgaagtat | 1020 | |
| gaagtgcaag gcgaagtgtt caccaaaccc cagctgtggc cctgaggccc agctgtgggt | 1080 | |
| cctgaaggta cctcccggtt ttttacaccg catgggcccc acgtctctgt ctctggtacc | 1140 | |
| tcccgctttt ttacactgca tggttcccac gtctctgtct ctgggccttt gttcccctat | 1200 | |
| atgcattgca ggcctgctcc accctcctca gcgcctgaga atggaggtaa agtgtctggt | 1260 | |
| ctgggagctc gttaactatg ctgggaaacg gtccaaaaga atcagaattt gaggtgtttt | 1320 | |
| gttttcattt ttatttcaag ttggacagat cttggagata atttcttacc tcacatagat | 1380 | |
| gagaaaacta acacccagaa aggagaaatg atgttataaa aaactcataa ggcaagagct | 1440 | |
| gagaaggaag cgctgatctt ctatttaatt ccccacccat gacccccaga aagcaggagg | 1500 | |
| gcattgccca cattcacagg gctcttcagt ctcagaatca ggacactggc caggtgtctg | 1560 | |
| gtttgggtcc agagtgctca tcatcatgtc atagaactgc tgggcccagg tctcctgaaa | 1620 | |
| tgggaagccc agcaatacca cgcagtccct ccactttctc aaagcacact ggaaaggcca | 1680 | |
| ttagaattgc cccagcagag cagatctgct ttttttccag agcaaaatga agcactaggt | 1740 | |
| ataaatatgt tgttactgcc aagaacttaa atgactggtt tttgtttgct tgcagtgctt | 1800 | |
| tcttaatttt atggctcttc tgggaaactc ctccccttt ccacacgaac cttgtggggc | 1860 | |
| tgtgaattct ttcttcatcc ccgcattccc aatatacca ggccacaaga gtggacgtga | 1920 | |
| accacagggt gtcctgtcag aggagcccat ctcccatctc cccagctccc tatctggagg | 1980 | |
| atagttggat agttacgtgt tcctagcagg accaactaca gtcttcccaa ggattgagtt | 2040 | |
| atggactttg ggagtgagac atcttcttgc tgctggattt ccaagctgag aggacgtgaa | 2100 | |
| cctgggacca ccagtagcca tcttgtttgc cacatggaga gagactgtga ggacagaagc | 2160 | |
| caaactggaa gtggaggagc caagggattg acaaacaaca gagccttgac cacgtggagt | 2220 | |
| ctctgaatca gccttgtctg gaaccagatc tacacctgga ctgcccaggt ctataagcca | 2280 | |
| ataaagcccc tgtttacttg a | 2301 | |

<210> SEQ ID NO 10
<211> LENGTH: 2301
<212> TYPE: DNA
<213> ORGANISM: homo sapiens

<400> SEQUENCE: 10

```
aggaattgaa ctcagctctg ccccaagcgg acctaataga catctacaga actctccacc      60
ccaaatcaac agaatataca tttttttcag caccacacca cacctattcc aaaattgatc     120
acatagttgg cagtaaagct ctcctcagca aatgtaaagg aacagaaatt ataacaaact     180
atctctcaga ccacagtgca atcaaattag aactcagaat taagaatctc actcaaaacc     240
gcacaactac atggaaactg aacaacctgc ttctgaatga ctactgggta cataatgaaa     300
tgaaggcaga aataaagatg ttctttgaaa tgaacaagaa caaacacaca ataccaga      360
atctctggga cgcattcaaa gcagtgtgta gagggaaatt tatagcacta aatgcccaca     420
agagaaagca ggaaacatcc aaaattgaca tcctaacatc acagttaaaa gaactagaaa     480
agcaagagca aacacattca aaagctagca gaaggcaaga gataactaaa atcagagcag     540
aactgaagga aatagagaca caaaaaccct tcaaaaaatt aatgaatcca ggagctggtt     600
ttttgaaagg atcaacaaaa tagatagacc actagcaaga ctaataaaga aaaaagaga     660
gaagaatcaa atagacacaa taaaaaaatg ataaggggga tatcaccacc gatcccacgg     720
aaatacaaac taccatcaga gaatactaca acacctcta cgcaaataaa ctagaaaatc     780
aagaagaaat ggataaattc ctcgacacat acactctccc aagactaaac caggaagaag     840
ttgaatctct gaatagacca ataacaggat atgaaattgt ggcaataatc aataccttac     900
caacaaaaaa gagtccagga ccagatggat tcacagccga attctaccag aggtacaagg     960
aggaactggt accattcctt ctgaaactat tccaatcaat agaaaaagag ggaatcctcc    1020
ctaactcatt ttatgaggcc agcatcattc tgataccaaa gccgggcaga gacacaacca    1080
aaaaagagaa ttttagacca atcaatatcc ttgatgaaca ttgatgcaaa aatcctcaat    1140
aaaatactgc aaaccaaat ccagcagcac atcaaaaagc ttatccacca tgatcaagtg    1200
ggcttcatcc ctgggatgca aggctggttc aatatacgca aatcaataaa tgtaatccag    1260
catataaaca gagccaaaga caaaaaccac atgattatct caatagatgc agaaaagacc    1320
tttgacaaaa ttcaacaacc cttcatgctc aaaactctca ataaattagg tattgatggg    1380
acgtatttca aaataataag agctatctat gacaaaccca cagccaatat catactgaat    1440
gggcaaaaac tggaagtatt cactttgaaa actggcacaa gacagggatg ccctctctca    1500
ccactcctat tcaacatagt gttggaagtt ctggccaggg caattaggca ggagaaggaa    1560
ataaagggta ttcaattagg aaaagaggaa gtcaaattgt ccctgtttgc agacgacatg    1620
attgtatatc tagaaaaccc cattgtctca gcccaaaatc tccttaagca gataagcaac    1680
ttcagcaaaa tctcaggata caaaatcaat gtacaaaaat cacaagcatt cttatacacc    1740
aacaacagac aaacagagag ccaaatcatg agtgaaatcc cattcacaat tgctttaaag    1800
agaataaaat acctaggaat ccaacttaca agggatgtga aggacctctt caaggagaac    1860
tacaaaccac tgctcaatga aataaaagag gataaaaaca aatggaagaa cattccatgc    1920
tcatgggtag gaagaatcaa tatcatgaaa atggccatac tgcccaaggt aatttacaga    1980
ttcaatgcca tccccatcaa gctaccaatg cctttcttca cagaattgga aaaaactatt    2040
tttagttcat atggaaccaa aaaagagccc gcattgccaa gtcaatccta agccaaaaga    2100
acaaagctgg aggcatcaca ctacctgact tcaaactata ctacaaggct acagtaacca    2160
aaacagcatg gtactggaac caaaacagag atatagatca atggaacaga acagagccct    2220
caaaattaat gccacatatc tacaactatc tgatctttga caaacctgag aaaaaccagc    2280
```
aatggggaaa ggattcccca t                                                   2301

<210> SEQ ID NO 11
<211> LENGTH: 2024
<212> TYPE: DNA
<213> ORGANISM: homo sapiens

<400> SEQUENCE: 11

```
aaggcaagag atctaggact tctagcccct gaactttcag ccgaatacat ctttccaaa       60
ggagtgaatt caggcccttg tatcactggc agcaggacgt gaccatggag aagctgttgt      120
gtttcttggt cttgaccagc ctctctcatg cttttggcca gacagacatg tcgaggaagg      180
cttttgtgtt tcccaaagag tcggatactt cctatgtatc cctcaaagca ccgttaacga      240
agcctctcaa agccttcact gtgtgcctcc acttctacac ggaactgtcc tcgacccgtg      300
ggtacagtat tttctcgtat gccaccaaga gacaagacaa tgagattctc atattttggt      360
ctaaggatat aggatacagt tttacagtgg gtgggtctga aatattattc gaggttcctg      420
aagtcacagt agctccagta cacatttgta caagctggga gtccgcctca gggatcgtgg      480
agttctgggt agatgggaag cccagggtga ggaagagtct gaagaaggga tacactgtgg      540
gggcagaagc aagcatcatc ttggggcagg agcaggattc cttcggtggg aactttgaag      600
gaagccagtc cctggtggga gacattgaaa atgtgaacat gtgggacttt gtgctgtcac      660
cagatgagat taacaccatc tatcttggcg ggcccttcag tcctaatgtc ctgaactggc      720
gggcactgaa gtatgaagtg caaggcgaag tgttcaccaa accccagctg tggccctgag      780
gcccagctgt gggtcctgaa ggtacctccc ggttttttac accgcatggg ccccacgtct      840
ctgtctctgg tacctcccgc ttttttacac tgcatggttc ccacgtctct gtctctgggc      900
cttttgttccc ctatatgcat tgcaggcctg ctccaccctc ctcagcgcct gagaatggag      960
gtaaagtgtc tggtctggga gctcgttaac tatgctggga acggtccaa aagaatcaga      1020
atttgaggtg ttttgttttc atttttattt caagttggac agatcttgga gataatttct      1080
tacctcacat agatgagaaa actaacaccc agaaaggaga aatgatgtta taaaaaactc      1140
ataaggcaag agctgagaag gaagcgctga tcttctatt aattccccac ccatgaccc      1200
cagaaagcag gagggcattg cccacattca cagggctctt cagtctcaga atcaggacac      1260
tggccaggt tctggtttgg gtccagagtg ctcatcatca tgtcatagaa ctgctgggcc      1320
caggtctcct gaaatgggaa gcccagcaat accacgcagt ccctccactt tctcaaagca      1380
cactggaaag gccattagaa ttgccccagc agagcagatc tgcttttttt ccagagcaaa      1440
atgaagcact aggtatataa atgttgttac tgccaagaac ttaaatgact ggttttgtt      1500
tgcttgcagt gctttcttaa ttttatggct cttctgggaa actcctcccc ttttccacac      1560
gaaccttgtg gggctgtgaa ttctttcttc atccccgcat tcccaatata cccaggccac      1620
aagagtggac gtgaaccaca gggtgtcctg tcagaggagc ccatctccca tctccccagc      1680
tccctatctg gaggatagtt ggatagttac gtgttcctag caggaccaac tacagtcttc      1740
ccaaggattg agttatggac tttgggagtg agacatcttc ttgctgctgg atttccaagc      1800
tgagaggacg tgaacctggg accaccagta gccatcttgt ttgccacatg gagagagact      1860
gtgaggacag aagccaaact ggaagtggag gagccaaggg attgacaaac aacagagcct      1920
tgaccacgtg gagtctctga atcagccttg tctggaacca gatctacacc tggactgccc      1980
aggtctataa gccaataaag cccctgttta cttgaaaaaa aaaa                      2024
```

<210> SEQ ID NO 12
<211> LENGTH: 2421
<212> TYPE: DNA
<213> ORGANISM: homo sapiens

<400> SEQUENCE: 12

| | | | | | |
|---|---|---|---|---|---|
| caccctcatg | agcccgggt | acgtttaact | attgagggcc | aggaaattgc | cttcctcctg | 60 |
| gacactggcg | cagccttctc | agggttaatc | tcctgtcctg | gatgactgtc | ttcaaggtcc | 120 |
| gttaccaccc | gaggaatcct | gggacagcct | ataaccaggt | atttctccca | catcctcagt | 180 |
| tgtaattgag | agactttaat | cttttcacat | gccttttttg | ttattcctga | aagtcccaca | 240 |
| cccttattaa | ggagggatat | attagccaag | gctggagcta | ttatctacat | gaatatgggg | 300 |
| aaaaagttac | ccatttgctg | tcccctactt | gaggagggaa | tcaaccctga | agtctgggca | 360 |
| ttggaaggac | aatttggaag | ggcaaaaaat | gcctgcccag | tccaaatcag | gttaaaagat | 420 |
| cccaccactt | ttccgtatca | aaggcaatat | cccttaaggc | ctgaagctca | taaggatta | 480 |
| tagaatattg | ttaaacattt | aaaagctcaa | ggcttagtga | ggaaatgcag | cagtccctgc | 540 |
| aacacccag | ttctaggagt | acaaaaacca | aacagtcagt | ggagactagt | gcaagatctt | 600 |
| agactcatta | atgaggcagt | aattcctcta | tatccagttg | tacccaaccc | ctataccctg | 660 |
| ctctctcaaa | taccagggga | agcagaatgg | ttcacggttc | tggacctcaa | ggatgccttc | 720 |
| ttctttattc | ccctgcactc | tgactcccag | tttctctttg | cttttgagga | tcccacagac | 780 |
| cacacgtccc | aacttacaca | gatggtcttg | ccccaagggt | ttagggatag | ccctcatctg | 840 |
| tttggtcagg | cactggccca | agatctatag | gccacttctc | aagtccaggc | actctggtcc | 900 |
| ttcaatatgt | ggatgattta | cttttggcta | ccagtttgga | agcctcgtgc | cagcaggcta | 960 |
| ctctggatct | cttgaacttt | ctggctaatc | aagggtacaa | ggtgtctagg | tcgaaggccc | 1020 |
| agctttgcct | acagcaggtt | aaatatctaa | gcctaatctt | agccaaaggg | accagggccc | 1080 |
| tcagcaagga | atgaatacag | cctatactgg | cttatcctca | ccctaagaca | ttaaaacagt | 1140 |
| tgcggggatt | ccttggaatt | actggctttt | gctgactatg | gatctccaga | tacagcgaga | 1200 |
| cagccaggcc | cctctatact | ctaatcaagg | aaacccagag | ggcaaatact | catctagtcg | 1260 |
| aaagggaacc | agaggcagaa | acagccttca | aaagcttaaa | gcaggctcta | gtacaagctc | 1320 |
| cagctttaag | ccttcccaca | ggacagaact | tctctttata | catcacagag | agagccaaga | 1380 |
| tagctcttgg | agtccttaga | ctcgtgggac | aaccccacaa | ccagtggcat | acctaagtaa | 1440 |
| ggaaattgat | gtagtagcaa | aaggctggcc | tcactgttta | agggtagttg | cagcagcggc | 1500 |
| cgtcttagcg | tcagaggcta | tcagaataat | acaaggaaag | gatctcactg | tctgactac | 1560 |
| tcatgatgta | aatggcatac | taggtgccaa | aggaagttta | tggctatcag | acaaccgcct | 1620 |
| cttagatgcc | aggcactact | ccttgaggga | ctggtgctta | aaatatgcac | gtgcgtggcc | 1680 |
| ctcaaccctg | ccacttttct | cccagaggat | ggggaaccaa | ttgagcatga | ctgccaacaa | 1740 |
| attatagtcc | agacttatgc | cgcccgagat | gatctcttag | aagtcccctt | aactaatcct | 1800 |
| gaccttaacc | tatataccga | cggaagttca | tttgtggaga | atgggatacg | aagggcaggt | 1860 |
| tacgccatag | tgatgtaacc | acacttgaaa | gcaagcctct | tccccagggg | accagtgccc | 1920 |
| agttagcaga | actagtggca | cttacccgag | ccttagaact | gggaaaggga | aaagaataa | 1980 |
| atgtgtatac | agataacaag | tatgcttatc | taatcctaca | tgcccatgct | gcaatatgga | 2040 |
| aagaatggga | gttcctaacc | tctgggaacc | ccgctggat | gccacaggga | agttatggag | 2100 |
| ttattgcaca | tggtgcagga | acccaaagag | gtgggagtct | tacactacca | aggccatcaa | 2160 |

```
aatgggaagg agagggggaga acagcagcat aagcggctgg cagaggtagg gaaagaccag   2220
caagaaggaa agagagaaag agaaagtcag agaaagagac agagagagga agagacagag   2280
agacagaacg ttaaagaggg tgtcagaaac agagacaaac aaaaggagtc agaaagaagg   2340
acagacacag aaagtcaaag agagagttaa aagagagga agagacaaag aagtcgaaga    2400
gagaaagaga gagatggaag t                                             2421
```

<210> SEQ ID NO 13
<211> LENGTH: 2421
<212> TYPE: DNA
<213> ORGANISM: homo sapiens

<400> SEQUENCE: 13

```
ctttgcagat aaatatggca cactagcccc acgttttctg agacattcct caattgctta     60
gacatattct gagcctacag cagaggaacc tccagtctca gcaccatgaa tcaaactgcc    120
attctgattt gctgccttat cttttctgact ctaagtggca ttcaaggtaa ggaacatcaa   180
aggatactta atttgtaaaa tgagaaatag gaataggtat aaattctaaa aatacagaaa   240
taatgtattt gtaaaagttt cactgcatgc ttataaataa gagggaaata aatagagatt   300
ccctcagatc ataaaactta tatgaattga agtgagagaa acaaatagaa taagagaaag   360
agaaggaaaa agggaaggag gacagaagag atggggaaga gggaggatag agagagaaaa   420
tgtgagggaa tgcggacaga gatgagatac agatacttcc ttacctaact aagctcaatg   480
aaccacatga actgtgctta agggtttgac tttataatca acaagctgca attcttttct   540
tccagataat caactcttta atcatttaca gttgtgttat gatgtgatcc attcctcctc   600
agattaagtg actatttgct gatatgggga tataggttct gctaaatacc accagtctac   660
attaaatgcc taaatgaac actgtgctaa ccttctctgc tgttcctctt ttcctacagg     720
agtacctctc tctagaactg tacgctgtac ctgcatcagc attagtaatc aacctgttaa   780
tccaaggtct ttagaaaaac ttgaaattat tcctgcaagc caattttgtc cacgtgttga   840
gatcatgtga gtgaaatccc atctgattat cacttccctg gttgtaatta tatactgtat   900
taaatatgta atgataataa aaaaagatca gtaaagggtt tgtgatgatt ctaaaactaa   960
tgtacagcaa acaaaaacat gcagagtgaa acttaaatgt ctgacttcag aactgcgtat  1020
gccatctgtt ttattgaccc aacacagttt taaatatttt catccctatt tatttctaca  1080
gtgctacaat gaaaaagaag ggtgagaaga gatgtctgaa tccagaatcg aaggccatca  1140
agaatttact gaaagcagtt agcaaggaaa ggtaggtttg ctgttgcctg cagaagaatt  1200
gctctttagg aaacggcaat cttgggagtc agaaatactt gcattgtggt ttgctgtgca  1260
atcgctggtt taaagtatg ttaccaccac gccctcccct acctccattt atttaaatgc   1320
tgaggcacca tcttgtgtga taagtatcag aagttaccct gattaccagt caaccttgaa  1380
gtacagctat aactatctaa gcaaaactga caacattttc cccaagtctt tcatggttga  1440
aaaaagcaac ccctataatc cataatgaat gcatagcagc aggaaagctc agttatctat  1500
tctatgaact cggtactttc caaacacaac ccaatctgaa gccagagtca gactatcaca  1560
cttttatatc cccttctct tcttacaggt ctaaagatc tccttaaaac cagagggag    1620 caaaatcgat gcagtgcttc caaggatgga ccacacagag gctgcctctc ccatcacttc  1680
cctacatgga gtatatgtca agccataatt gttcttagtt tgcagttaca ctaaaaggtg  1740
accaatgatg gtcaccaaat cagctgctac tactcctgta ggaaggttaa tgttcatcat  1800
cctaagctat tcagtaataa ctctaccctg gcactataat gtaagctcta ctgaggtgct  1860
```

```
atgttcttag tggatgttct gaccctgctt caaatatttc cctcaccttt cccatcttcc    1920
aagggtacta aggaatcttt ctgctttggg gtttatcaga attctcagaa tctcaaataa    1980
ctaaaaggta tgcaatcaaa tctgcttttt aaagaatgct ctttacttca tggacttcca    2040
ctgccatcct cccaaggggc ccaaattctt tcagtggcta cctacataca attccaaaca    2100
catacaggaa ggtagaaata tctgaaaatg tatgtgtaag tattcttatt taatgaaaga    2160
ctgtacaaag tagaagtctt agatgtatat atttcctata ttgttttcag tgtacatgga    2220
ataacatgta attaagtact atgtatcaat gagtaacagg aaaattttaa aaatacagat    2280
agatatatgc tctgcatgtt acataagata aatgtgctga atggttttca aaataaaaat    2340
gaggtactct cctggaaata ttaagaaaga ctatctaaat gttgaaagat caaaaggtta    2400
ataaagtaat tataactaag a                                              2421
```

<210> SEQ ID NO 14
<211> LENGTH: 2421
<212> TYPE: DNA
<213> ORGANISM: homo sapiens

<400> SEQUENCE: 14

```
agatgacttt tttctattta tatttaataa gatgatgaac ccttcttgca ttcccgaaat      60
aaacctcaac tgttacagtg ttttattctt ttaatatgta cgaagtacat gttaagcaag     120
ttatttccta agcagcccca caaactgggc actactacca tcctgctctg cccctccctc     180
actctacttc agccacttca gccacaatgg cctctcctca ctgcccctct gatgcaccaa     240
gcttgttctc acctcaggaa tgtgcaacac ctgccagact gctgttccc cggagcctcc      300 atccccagat atcctcatat atcatcctcc tcttcatttg tgtctctgct tacatatgac     360
ctatttacag aagcctttcc tgtctacccc ccatgaaata gaaatcgcat tccaatcttg     420
tctctacccc aatgctgttt cattttgtct gtagcaattg tcatcatctc atatatattc     480
acatgtggaa aatacacaaa atgtttaact tcttttaatt tacattccat ttccccatga     540
attgaagctc catgacagcg gagattttc tctgctttcc ctgttgctca cttcccagca     600
ccaagagcag gcctggcaca tgggaagtac ttactattta ttgaatggat gaatgaacaa     660
atgaatgaat ggatacttat tttacacata agaaaactga agcttataga aattaagtaa     720
ctaaaatcac acagaagcac agctgaaact aaaacctacg tctaactttc aattcctgac     780
ccttaaccat taaaacaaat gacaggtgac tttaggccac tgaaaatgct catataatct     840
tatgaattct aaagcacaag ttaatcacac cattgattga aagtctgagg aatactgtat     900
agacaagccc ctgtacaagg taagcaaaag aatcagagga tggcctccaa agaattccct     960
ggacattatg ggaattacat tgttagcctt cctactgata cccataagcc tcacagcaag    1020
catcatgaag ctgtgacctt catctgcaca tgcccttgta tacccaaaag ataaaactgg    1080
atgcttcagg gccgaatggc caataaacac gtgtttatta ctggcatggg cagacacaca    1140
tactgaaagt accatttccc agcggactag ccatattatg atcagtacag acactaaaga    1200
tttagctttg aaaaaactat ttgctcttcc aaagctgaag atcttctgt gatttcaaca    1260 ggcaagttac agtcaggtat tcttaatgtt cttttcctcc tctctcactg ggatactttc    1320
tttccttcag acaacgtcaa gcgaaaaaca aaatttcaca atctccatt tctgacacta    1380 aacagtacag tatcttttatt tttttttataa tttaatcaaa ccctgtattt tagaactgtg    1440
gggctgatcc aacattgcaa tgtgtcacat ttaattccat caatgtaaag cataatgagc    1500
```

```
aaagattaag gtagtgaggc ataactaaat gttttgaacc tgtgaatttc aaaagcaagg    1560
cccatttgtg ttattttcta aatagtaaat aaaatcattt tccaacattt cactatcaaa    1620
ttacagtaat ttttccacca gtacacactt gaggaaagcc acaaaaagac ttttccaaca    1680
gttcattctg ttattgctca taaccttcta aatacttctc ctcattggct tctattcaaa    1740
ggtaaatgga aagcagtaaa atttatggaa aatatattca actgcttaaa atacatcaac    1800
caaaaaaaag attttagagc tgtattatga gttgtgaaat tgcattgcct tcacttacct    1860
ttcagtttca ctggtaggta acaaaactga cagactggtc aagttccaaa acatccccta    1920
tatagagcct gactcttcca tctcaaattc tcaccttggt caaggccaga gtaaacacct    1980
gtccttcaca tttttacaca acatcacttt gtatgctaca aatataagct ttcataccag    2040
ggaggaagca aattccagga cactggaaac atttctgctc tcttaaacca gtctgttgat    2100
tgttcccttg actttctcag ctgtcaggat agtgaaagga ggaaaactgc aaaactgtaa    2160
agtataacct gataagtttg ccctttaagc ttttcacaca gagagaggta aaataaaact    2220
caagtctaag gtttaaaatt gagctatgaa tattatattc tagcactaga caaaaatgtt    2280
gcaagatttt aataaaataa gattattaaa atcaattttt acatttcatg ggccaaggag    2340
agacatcaaa gaatgtttaa ctaacatttt aaagatacta tactttataa agttaagaag    2400
aaaaatgaca actgcaccag t                                              2421
```

<210> SEQ ID NO 15
<211> LENGTH: 1227
<212> TYPE: DNA
<213> ORGANISM: homo sapiens

<400> SEQUENCE: 15

```
ctttgcagat aaatatggca cactagcccc acgttttctg agacattcct caattgctta     60
gacatattct gagcctacag cagaggaacc tccagtctca gcaccatgaa tcaaactgcc    120
attctgattt gctgccttat ctttctgact ctaagtggca ttcaaggagt acctctctct    180
agaactgtac gctgtacctg catcagcatt agtaatcaac ctgttaatcc aaggtcttta    240
gaaaaacttg aaattattcc tgcaagccaa ttttgtccac gtgttgagat cattgctaca    300
atgaaaaaga agggtgagaa gagatgtctg aatccagaat cgaaggccat caagaattta    360
ctgaaagcag ttagcaagga aaggtctaaa agatctcctt aaaaccagag gggagcaaaa    420
tcgatgcagt gcttccaagg atggaccaca cagaggctgc ctctcccatc acttccctac    480
atggagtata tgtcaagcca taattgttct tagtttgcag ttacactaaa aggtgaccaa    540
tgatggtcac caaatcagct gctactactc ctgtaggaag gttaatgttc atcatcctaa    600
gctattcagt aataactcta ccctggcact ataatgtaag ctctactgag gtgctatgtt    660
cttagtggat gttctgaccc tgcttcaaat atttccctca cctttcccat cttccaaggg    720
tactaaggaa tcttttctgct ttggggttta tcagaattct cagaatctca ataactaaa    780 aggtatgcaa tcaaatctgc ttttttaaaga atgctcttta cttcatggac ttccactgcc    840
atcctcccaa ggggcccaaa ttctttcagt ggctacctac atacaattcc aaacacatac    900
aggaaggtag aaatatctga aatgtatgt gtaagtattc ttatttaatg aaagactgta    960
caaagtagaa gtcttagatg tatatatttc ctatattgtt ttcagtgtac atggaataac   1020
atgtaattaa gtactatgta tcaatgagta acaggaaaat tttaaaaata cagatagata   1080
tatgctctgc atgttacata agataaatgt gctgaatggt tttcaaaata aaaatgaggt   1140
actctcctgg aaatattaag aaagactatc taaatgttga aagatcaaaa ggttaataaa   1200
```

```
<210> SEQ ID NO 16
<211> LENGTH: 98
<212> TYPE: PRT
<213> ORGANISM: homo sapiens

<400> SEQUENCE: 16

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 17
<211> LENGTH: 5687
<212> TYPE: DNA
<213> ORGANISM: homo sapiens

<400> SEQUENCE: 17
```

| | |
|---|---:|
| ctctctggtt gcccttaaca ttttttcctt catttcaact ttggtgggtc tgatgattat | 60 |
| gtgtcttggg gttgctcttc tcgaggagta tcttagtagt attctctgta tttcctgaat | 120 |
| ttgaatgttg gcctgtcttt ctaggttggg aagttctcc tggataatat cctgaagagt | 180 |
| atttttcaac ttggttctat tctccttgtt actttcaggt acaccaatca aacgtagatt | 240 |
| tggtcttgtc acatagtccc atatttcttg gaggttttat tcgttccttt ttattctttt | 300 |
| ttctctagtt ttgtcttctc gctttatttc actaagttga tcttcaatct ctgatatcct | 360 |
| tgcttctgct tgattgattc agctatcccc cgctcgatat tacaaaccat gtcacgaggc | 420 |
| gtggacaccc ccatgatat ggggagtatt atcacccccc tcttcccca ctggatatta | 480 |
| caaaccatgt catagggagg tggacatccc ccacaatatg aggagtaata tcacacccct | 540 |
| ttccccgcag tggatattat gaaccatgtc acaggcggtt aaacacccc aacgatatgg | 600 |
| ggagtaatat cacactcctc tccccctgg atattacgaa ccatgtcatg gggggtggac | 660 |
| acccttgca atatggggag taaaatcacc ccctctccc caactggat attatgaacc | 720 |
| atgtcacagt gggggaaaaa tcctctgtga tatgcagagt aatatcaccc cactctcacc | 780 |
| acctggatat tacgaaccat gtcacagggg ggtggacacc ccaagatg ggggagtaat | 840 |
| atcacctcac tctctgccac cagatattac aaactgtgtc acagggggt gaacaaccc | 900 |
| cacaatatgg ggagcactat caccccctc ccccagggta ttatgatcca tgtcacaggg | 960 |
| gggtggatac cacccactat atgggagta atatcacctt tctctcccgc ctggtttttt | 1020 |
| atgaaccgtg tcacaggggg gtggacaccc cttgcgatat ggggagtaat atcacccccc | 1080 |
| tctccaccat ctggatatta cgaaccatgt cacagggggg tggacacccc tgcgatatgg | 1140 |
| ggaggaatat gcccctctcc ccacctggat attacaaatc atgtcacggg ggacggacat | 1200 |

```
cccccacaat atggggagta atatcaccac actctcccct gctggatatt acgaaccata   1260
tcacaggcgg ctggagacac aaggcattaa caatatttcg agtaatatta tctttccctt   1320
tgaacattat gaacaatatg acagagggt gtacacctcc tgcgatattg ggagtaatgt    1380
catcccctcc cccactggat attaggaacc atattactgg gggatgtatt ccccttcta    1440 gattgggagg aagatcatac ttgccctccc tgaatatttg aaacaatatc atagggtttt  1500
gtacactttt acgatattgg gagtaatatc atcctttctc ccctggaaa ttaggaacaa    1560 tatcacaggg gtggtgtaca cccctgcaat atttagggta atattattgt cttctcccct   1620
cgatattagg aacaatatta caaggacggt gtaaagtacc tgccaaattg ggaaaaatac   1680
tatcctctcc ctcttgtata ttagaaacaa taacacaggg ggaatgtaca cccactgcca   1740
tattgggagt aatatcatac tcgccccatc ccccagatat taggaacaat atcacagcag   1800
gggtgtacac ttttacgata ttgggagtaa tatcatactc tctcccctg gaaattagga    1860 ataatatcac agagatggtg tagaccctct gcaatactta ggataatatt atcatctccc   1920
ccctcgatat taggaacaat attacgggga gtgtaaatta cctgccaaat tggaggtaat   1980
cctctcctct ctctcccctgt attttagaaa atataacaca caggaaatgt acaacactgc  2040
gatattcgga gtaatatctt cttctcccca cctggatatt aggaacaata acacggacgg   2100
ggcgtacacc cctcgcgata ttgaatgtaa tgtcatcctc tccctccctt tatattacga   2160
acaatatcac agggggtgt acaacccctg caatattgga agtagtatca tccattctcc    2220
catgaatatt aggaacaata tcacagggt agagtacacc ctctgcaatt tcgggagtaa    2280
catcatcctc tcgttccctg gatattataa acaacaccac ggggggtgg gggtgtacac   2340 acccttcgat attgggagta atataatcct ttccctccct atatattaga agcaatatca   2400
caggggttgg tgtaaacttc ttgcgatatg gggattaata tcaccccct ctcctgccct    2460 ggatattatg aaccatatca cagggaggtg gacacactt gcgatatggg gagtaatatc    2520
acgcccctct ccccccgat attacgaacc atatcacaag ggagtggacc ccccccacga   2580 tatgggagt aatatcaccc ccctctcccg ccctggatat tacgaaccat atcacagggg   2640
gatggacacc ccccgcgatg cggggagtaa tgtcaccccc ttctgcccc taggatatta   2700 cgaaccatat catggacacc ctccacgata ttggaaataa tatcatcctc tcccccttgg   2760
atattaggaa caatatcaca ggggttgta cacctcctat gatattggaa gtaatatcat   2820
cctctccctc ctggatatta gcaacaatat cacagggagt gtgtacaacc ccagcgatat  2880
ttggagtaat atcaccctct caccccatgg atatgagaaa caatatcaca ggggaggtgt   2940
acatcccacg tgatattgtg tgtaatatca ttcttcccca accctgcaa tattgtggtg    3000 taatataatt ctctcccttc ctggacatta tgaacaatat cactactagg tgatacatta   3060
ggagtaatgt atccatagga tattatgagg aatatcacag ggtgtacacc cactgtgata   3120
ttagaggtaa tatctcccta aaatattaag aagaatatct tacacccact gtgactttag   3180
aagtaatatc tccctaaaac gttacaaata acatcgcagg gtgtacactc acagtgatat   3240
taggagtaat atctccctag aatattacaa atacacatgg tgtaaaccca ctgtgacttt   3300
agaagaacta tctccctaaa ataatacaaa atatcgcag tgtataccat aatatcccct   3360
agaatatcat aaataatatc acagggtgta cacccactgt gataatagga ataataccac   3420
cccaggatat tatgaataat gtcacaggct gtacacccac tatgacatta ggagtaatat   3480
ctccctagga cactatgaat aacatcacag atttacacc catggtgtgc acccactatg   3540
atattaggag taatatctgc acaggatata acaaataata gtacagggtg tacacatatg   3600
```

```
atatacaccc actgtgatat taggagaaat atatccctag gatattatga ataacctctc   3660
agagtacaca cacatggtat acaccctctg tggcattagg aacaataact ttctaaaaca   3720
ttacgaataa catcacagaa tgtacacaca tggtttacac ccactgtgac aggtgcaata   3780
tctcccttgg atattatgaa taacaacaaa ctatcactgt catattagga gtaatttctc   3840
cctagaatat tacaaataac atcacagggt gttcatttat ggtgcacacc cactgtgata   3900
ttaggagtaa tatctcccta ggatattact tttcatataa agtgtgtac atccactgtg    3960
atattgggaa aaatatttct ctaggatatt atgaataata tcacagagcg tacacccact   4020
gtgatattag gagtaataat tccctgggtt attatgaata atatcacagg atgtacaacc   4080
actgtgatat taggagcaat atcttcctag gatattacaa ataatatcac agggtgtaca   4140
cccactgtga tattaaagta atttttaggt tattgtgaat aatatcacca agtgtacaaa   4200
catggtgtac actcactgtg atatcaggag taatatctca gtaaaatatt atgaataata   4260
tcacagggta tacacccact gtgatattag cagtagtatc tttgtaggat attacaaata   4320
atatcacagg gtgtatgccc actatgacat tagaagcaat atctccctag gatatcaaaa   4380
ataatatcac agggtgtaca acttctacat cccaggttct aagggattct cctgcttcag   4440
cctcctgagt ggctgggatt acagatgccc accaccacac ctggctaatt tcgtattttc   4500
agtagagatg gggtatcacc atgctggtca ggctggtctg gaacttctga cctcaggtga   4560
tccaccagcc tcggccttcc aaagtgctgg gaatacaggt gtgagccaac gtgcttggca   4620
gagagttata tattaaataa atctggaaac atagctccca tgtttgagtg tgcatttact   4680
tttatgaaga aattatgtca gaaaacctaa ggatgataat aaatatgaaa agtaactggc   4740
atgtaaaaag gtcttttgat taagaactat aaggttcgat ttcattttta gataacgtga   4800
tcctagctct tgtatagtgc ttataaatat tctacatcaa aggaatttgt tgcacagtgt   4860
cagaataaaa taaagtgtat ttcactgctt cttaattttt aaattagact gagtttgttt   4920
tcctagagag agaagaacat tttttatttt ttctgaaaag agtaggccat attttactga   4980
gatcttagat ttgttatata ttaggttttg gtcttctaac attctccagt ggattttctc   5040
taaagtaggt atgcacagaa agagttgaat agcaaaaaag taaatcatgt aataattctg   5100
agattttttgg gtttgtcaca actgagaaat attgctgagg gtgtatggtc ctcaagtgtg   5160
aaaatgttcc ttgtgaattg cttgtatccg aaatatacac acaacattaa gtcctggttt   5220
ttatctttta ttttttccaa tcctttttttc ttctcaaggt gtccaagtca cacagagcca   5280
cagaatctca caggtgtctc agaattcctc ctcctgggac tctcagagga tccagaactg   5340
cagccactcc ttgctgggct gttcctatcc atgtgcctgg tcacgatgct ggggaacctg   5400
ctcatcatcc tggccgtcag ccctgactcc cacctccaca tccccatgta cttcttcctc   5460
tccaacctgt ccttgcctga cattggtttc accttggcca cggtccccaa gatgattgta   5520
gacatgcaat cacatagcag agtcatctcc catgcaggct gtctgacaca gatacctttc   5580
tttgtccttt ttgtatgtat agatgacatg ctcctgactg tgatggccta tgactgattt   5640
gtggccatct gtcaccccct gcactaccca gtcatcatga atcctca            5687
```

<210> SEQ ID NO 18
<211> LENGTH: 5687
<212> TYPE: DNA
<213> ORGANISM: homo sapiens

<400> SEQUENCE: 18

```
attgaattttt atctcagagc ccacatgaag caggatcaaa gtcagtacac atgaaaacta      60
gagcccaaag actataaagc atgaaataag gatttaagct aaccctatct tgtaagggdt     120
ttgtaaagcc cagcttgcat ctgagctaca ctagcaccag gacagccact cagtaatggg     180
gtttctcaag gttattgctt ttcattcagt tgaaatgaga gtcatttctt acccttatgc     240
cctgtgagat ttcactggag gttgttcact gaaacatttt catatcattg catcaaccct     300
cttgaactca ctgtgcctgc ccccagttca gtctgtgact cacaagtacc ctgcagcaaa     360
agaaatccaa tagagggcaa atccctcacc ttaccttcct ttctaagacc tttgatgttc     420
tcatgtgtca tttcataatt gggattgtca attagtcgcc tcatctctgg tcctcacttt     480
cctctctccc agccaaactc aaccttcagc ccacacaatg gaattcaaca aaatgaggta     540
acagttttct gtgtgagtca ctctgggcaa ctctgttcac agagcactgt gaggtgagca     600
gccagaaccc aggcaagtgt ttcagccatc caagaactgg caggcagccc aagagacact     660
ctcacctgat gacagactag caggatgagt cctggaggaa atggttccca acagctgcag     720
aaggagtctc ttggctcatg cacagcaatg ctcttctcaa ttaaaaacgt tgtcattatt     780
gacactgcag tgtaaaatcc ttttacactg tgctcacatt tctacaggcc ttcacctgct     840
ctgcccatta aagacaagac ccttccatga atgatgaca tctctaagtt actgttccac       900
ccaaacagtc ctatataatg aagagaaaaa ttttgctggc cctcaaaagg caaacacaag     960
gagaaagatt tccacaagct gtttctcttt gctgagcact tagaggaaaa ctgtaagtgg    1020
ttggaagaag gctttgtttt ctacaagact tttagttatt cctcagaaat tttcctgctt    1080
attcccagag gaggtcatct cttagatgct gtcagtcaga tagggattgg cagccaagca    1140
gaggtgctca gagaggtttc caactaatgt ggccagcgga aaactgccaa gaagcaggg     1200
atccttagga caaataaact ggaagatatt tggggataa aataaatcc ttttgaaat      1260
gaaagatgga gagatgctgt atatacaaat tgccctgttc tgaacaatgt tgtcactagg    1320
actggccctg gagaccaatg atacaaacca aaatgttctc agacatgctt tgatggtctt    1380
tttctccaaa gttatctatt ctgtttccat ttcattctca caggacttgc catggggttc    1440
tcataagatt tcacattggt cataatccag gtggccctgg actgcaacct ctgagttggc    1500
aacatcagaa taggaattac gaaaaaccaa tttaagtta aatacagaca caggcaaaag     1560
agagatgggt tgtcgaagct agtgcctagg tggacactgc ctcacatttt taattccaga    1620
agccatcagt actgagtgtc agatctcatt agtcaaacac agtgatcagg aatcctgttt    1680
tcctggagga tttccttgag ggagggacca ctcaagagtc tgaaatattt cacgtcatag    1740
agtatggatc tcacccccaac acccaatcag aaaatagggd gaactggaaa ccaaaattcc    1800
ccctcccgct gtgaaggat gaaaccaga gtgttggagt tctgtcctga taatggagca     1860
gacagctagg cagcaatcaa tgagggccag tacaggaatt cagtgctaag tattgggtca    1920
taacagaagt agggaaggta ttaatccagt gctatatgag gatcctggga cactggctcc    1980
tagtaatcta gttataacta ttagcaaaaa agaaaaaaaa aatcagtgat gtgaagagat    2040
ggcctaaagg agctccagca atatagctaa gcagctggca agtggtctga ggagcattgc    2100
aattccaggc ctcctaaggt ggcagtacgg gcactggtaa gacattctgc tgtggtgaaa    2160
ctagtttacc atagaggatt cacaattaaa ataggcaaac aggaaatgca agacagaggc    2220
taacaagggg tttttttttt ggtgggggggg agttgtttgt ttgtttgttt gttttctgag    2280
acggagtctt cctctgttgc ccaggctgga atgcagtggc acgatctcag ctcactacaa    2340
cctctgcctc ccaggttcaa gcagttcttc tgcctcagcc tcccaggttc aagcagttct    2400
```

```
tctgcctcag cctcccaagt acctgggact atagctgtgt gccaccacat tgactaattt    2460
ttgtactttt agtacagact gggtttcacc atgttggcca ggctggtgtc gaactcctga    2520
cctcaagtaa tccccccgcc ttggcctccc aaagtgctgg aattacaggc atgagccacc    2580
acacctggcc agttttggt aattcttaaa gaactcaatg agcaacactc aaacaaccat     2640
aaagactata gagctcatgg ttgaattta gatagctaaa cagacaggag tttttgtaag     2700
ttttgtaagt cttgctcatc cttccctctt ccatcctcta tctcaactat tctgtctacc    2760
attaaagcac cttagacctt gagtttggca atgcaacaag tgtgtgctca acacgaaata    2820
ggtaattcaa tagcaaagcc ctaaaacagc ctggcttgat tatttctcag ggcatgcagt    2880
tcctttgaag caggatcatt ttaataataa taataataga aataataata gaaattgaag    2940
acaattattt cacaatttcc atacacctaa gagctataca tatgaatgat aatgcataat    3000
tgtaaagcat gcatattaca ggtaataaat atgttagcta attataaaca atgcccattt    3060
tcatatagtt tatccttgcc aaataaaact gtaaaaaaaa gacacctttc aaatgctgct    3120
aaggagtaat acctgaatga ggttgattta atggagtctt agttcctgca tgtgttctaa    3180
ttgaatagac tatgtagtaa ttcccttaca tacccatcca tgtccaagaa cagtgaagat    3240
ctttatttaa tatgaattat tgcagatgat tagcacagtc tagccaaacc attccagtaa    3300
ttgtttttac ttgttatatt aatatataaa ttctcaaagg atataacagt gatgttgggt    3360
gaatttcact gaatgatagc tcaaacacct gaaatattga ctaagaaaac taatttatca    3420
atactgataa tcaattttaa tatgttaatt gattgtaata caggattctg tggttcaaaa    3480
aaaaagaaca agcaaaaaaa ctttcttcca tttccaaata ccaattaata gatctctact    3540
tccccttgga tttcttctta ccacctacca cctccaatct tcattctttc ctcacaaact    3600
aaacataaaa gttacctaca aagcatagaa tctgtgttaa aggatattct tgcttgtttt    3660
aagtccaaaa ttaaacagct ctgaattatt aaaaagcaca tgaattcaaa tgtcctattc    3720
taataagaaa atggtttaca tttctctatg ttcaaggaaa aaaatagtca agggtgtaca    3780
agtggggtaa aaattatttc cagtaggtta tgtgatttaa gttatagaaa cgaaccaggc    3840
aattcaatta aatgtcatgg aaagtaggtt ttttctttc ctcttttttt ctaatatgta    3900
cactttgtga aagataaat ccatagtgtg ataatttgtc cactgggtcc atcagacact     3960
ggagacagct tcctaagaat tataaggctt ctaaaggctt ctaaagccta aattgcctag    4020
agcattttgt gtgccaggca ctttgctagg tgccctaggg atgcaagaag tataaatgtt    4080
ttatgagaat acaggctgga aatgtattct tgattattcc tgtggaattt ctaggcagaa    4140
aagagtctaa tggggtatag gtatattttc tcaacacaat tttctgagcc tttaccagat    4200
gcagttctat ggtttgaatg tgtccctcag agtttgtgtg ttggaaactt aatccccaat    4260
gcaataatgt tggtgaggcc taatgaaagc ctaataatgt aggtgaggcc taatgagagc    4320
tgtttagacc atgaaggctc ttccctcatg atggattaa tgctgttatg gtgggaatgg     4380
gttcattatt actggggtgg gttcataata aaaagatgag tttggcctgc tattctctct    4440
ctttctcatc ctctcttcca ccatgggatg acacagcaag aaggccctg caagatgccc      4500 tccccctcagt attggacttc acagcctcca ggaccataag ccaataaatt tttgttcatt    4560
ataaatttcc cagtctgtgg tattctgtta tagcaacact caatttatgc attacttcca    4620
gattcttatg gctataccta cttctcacag tttgtattca cccctccttc aaccaagtac    4680
ccttaacaca gttcccatag tcacaaagcc aggtcactga agctgccctc tctccaacca    4740
```

| | | |
|---|---|---|
| cacacatata gatcaaatga ccccagacat agagctgatt gagaaggagg gaccagtacg | 4800 |
| agctctgctt ccccagcagc ttcctggaaa gaagaggcaa tacaacccaa cccaaaagtg | 4860 |
| caagagaagt aacacctcat gggatgagct taattaatca atgggagagg acactagaag | 4920 |
| acactagagg atctcccttc ctcccttict ttcccacttc acccctcca gtctctgaac | 4980 |
| catgagctat ttcaaaggtg cagtaatgct atatttggct tctctgaaga tatcctatga | 5040 |
| ggccaagtca tcagctttgt tcattatcta agagtggtgg ccagctcacc agcacttccc | 5100 |
| atcatgtttg ccctccctct ttccttgtg ttacttccca ttttcccta cttctgcttt | 5160 |
| cttggcatta aattctactc tgcaatgtta ggatataagt ttttgcctca gattctgttt | 5220 |
| tctaggaaac ccatgctaag acaacactgg cagtggccct ggaaaagtaa acctcatgat | 5280 |
| ggatttggag ttggattgtt cactgatctg aaggacagag gactccactt aagtggtaag | 5340 |
| cagtgtagct atgaactctg ccacgcaggc ctcacaatta ctgaggcttc ttttacctgt | 5400 |
| ggttaactgg gacacagaac agcaggaaat tgagtgtaga ggttatcaag tagctgcttc | 5460 |
| acttaattgg tataatttta tggagttaac ctggtttaga gtccagagaa cattccacat | 5520 |
| agcctagaaa gggtagttat ttgtccttac cataatcaag tcatactttg aatatgagtt | 5580 |
| ttccttccct gttcagcacc acttctctta gacttaagaa tgcctgatct gttgatatta | 5640 |
| tgtcccatgt aacattgcct gagacaaaga tatccatgta ccttaaa | 5687 |

<210> SEQ ID NO 19
<211> LENGTH: 140
<212> TYPE: PRT
<213> ORGANISM: homo sapiens

<400> SEQUENCE: 19

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
        35                  40                  45

Leu Leu Leu Ala Ala Leu Val Gln Asp Tyr Val Gln Met Lys Ala Ser
    50                  55                  60

Glu Leu Glu Gln Glu Gln Glu Arg Glu Gly Ser Ser Leu Asp Ser Pro
65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
            100                 105                 110

Val Gly Ala Pro Gly Lys Lys Arg Asp Met Ser Ser Asp Leu Glu Arg
        115                 120                 125

Asp His Arg Pro His Val Ser Met Pro Gln Asn Ala
    130                 135                 140
```

<210> SEQ ID NO 20
<211> LENGTH: 128
<212> TYPE: PRT
<213> ORGANISM: homo sapiens

<400> SEQUENCE: 20

```
Met Gly Phe Gln Lys Phe Ser Pro Phe Leu Ala Leu Ser Ile Leu Val
1               5                   10                  15

Leu Leu Gln Ala Gly Ser Leu His Ala Ala Pro Phe Arg Ser Ala Leu
```

```
            20                  25                  30
Glu Ser Ser Pro Ala Asp Pro Ala Thr Leu Ser Glu Asp Glu Ala Arg
            35                  40                  45

Leu Leu Leu Ala Ala Leu Val Gln Asp Tyr Val Gln Met Lys Ala Ser
 50                  55                  60

Glu Leu Glu Gln Glu Gln Glu Arg Glu Gly Ser Arg Ile Ile Ala Gln
 65                  70                  75                  80

Lys Arg Ala Cys Asp Thr Ala Thr Cys Val Thr His Arg Leu Ala Gly
                85                  90                  95

Leu Leu Ser Arg Ser Gly Gly Val Val Lys Asn Asn Phe Val Pro Thr
                100                 105                 110

Asn Val Gly Ser Lys Ala Phe Gly Arg Arg Arg Arg Asp Leu Gln Ala
                115                 120                 125
```

<210> SEQ ID NO 21
<211> LENGTH: 141
<212> TYPE: PRT
<213> ORGANISM: homo sapiens

<400> SEQUENCE: 21

```
Met Gly Phe Gln Lys Phe Ser Pro Phe Leu Ala Leu Ser Ile Leu Val
 1                   5                  10                  15

Leu Leu Gln Ala Gly Ser Leu His Ala Ala Pro Phe Arg Ser Ala Leu
            20                  25                  30

Glu Ser Ser Pro Ala Asp Pro Ala Thr Leu Ser Glu Asp Glu Ala Arg
            35                  40                  45

Leu Leu Leu Ala Ala Leu Val Gln Asp Tyr Val Gln Met Lys Ala Ser
 50                  55                  60

Glu Leu Glu Gln Glu Gln Glu Arg Glu Gly Ser Ser Leu Asp Ser Pro
 65                  70                  75                  80

Arg Ser Lys Arg Cys Gly Asn Leu Ser Thr Cys Met Leu Gly Thr Tyr
                85                  90                  95

Thr Gln Asp Phe Asn Lys Phe His Thr Phe Pro Gln Thr Ala Ile Gly
                100                 105                 110

Val Gly Ala Pro Gly Lys Lys Arg Asp Met Ser Ser Leu Glu Arg
                115                 120                 125

Asp His Arg Pro His Val Ser Met Pro Gln Asn Ala Asn
                130                 135                 140
```

<210> SEQ ID NO 22
<211> LENGTH: 116
<212> TYPE: PRT
<213> ORGANISM: homo sapiens

<400> SEQUENCE: 22

```
Ala Pro Phe Arg Ser Ala Leu Glu Ser Ser Pro Ala Asp Pro Ala Thr
 1                   5                  10                  15

Leu Ser Glu Asp Glu Ala Arg Leu Leu Leu Ala Ala Leu Val Gln Asp
            20                  25                  30

Tyr Val Gln Met Lys Ala Ser Glu Leu Glu Gln Glu Gln Glu Arg Glu
            35                  40                  45

Gly Ser Ser Leu Asp Ser Pro Arg Ser Lys Arg Cys Gly Asn Leu Ser
            50                  55                  60

Thr Cys Met Leu Gly Thr Tyr Thr Gln Asp Phe Asn Lys Phe His Thr
 65                  70                  75                  80

Phe Pro Gln Thr Ala Ile Gly Val Gly Ala Pro Gly Lys Lys Arg Asp
```

```
                    85                  90                  95
Met Ser Ser Asp Leu Glu Arg Asp His Arg Pro His Val Ser Met Pro
                100                 105                 110

Gln Asn Ala Asn
        115

<210> SEQ ID NO 23
<211> LENGTH: 212
<212> TYPE: PRT
<213> ORGANISM: homo sapiens

<400> SEQUENCE: 23

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
                20                  25                  30

Gly Glu Asp Ser Lys Asp Val Ala Ala Pro His Arg Gln Pro Leu Thr
            35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
            195                 200                 205

Leu Arg Gln Met
    210

<210> SEQ ID NO 24
<211> LENGTH: 136
<212> TYPE: PRT
<213> ORGANISM: homo sapiens

<400> SEQUENCE: 24

Met Cys Glu Ser Ser Lys Glu Ala Leu Ala Glu Asn Asn Leu Asn Leu
1               5                   10                  15

Pro Lys Met Ala Glu Lys Asp Gly Cys Phe Gln Ser Gly Phe Asn Glu
                20                  25                  30

Glu Thr Cys Leu Val Lys Ile Ile Thr Gly Leu Leu Glu Phe Glu Val
            35                  40                  45

Tyr Leu Glu Tyr Leu Gln Asn Arg Phe Glu Ser Ser Glu Glu Gln Ala
    50                  55                  60

Arg Ala Val Gln Met Ser Thr Lys Val Leu Ile Gln Phe Leu Gln Lys
```

```
65                  70                  75                  80

Lys Ala Lys Asn Leu Asp Ala Ile Thr Thr Pro Asp Pro Thr Thr Asn
                85                  90                  95

Ala Ser Leu Leu Thr Lys Leu Gln Ala Gln Asn Gln Trp Leu Gln Asp
            100                 105                 110

Met Thr Thr His Leu Ile Leu Arg Ser Phe Lys Glu Phe Leu Gln Ser
        115                 120                 125

Ser Leu Arg Ala Leu Arg Gln Met
        130             135
```